(12) United States Patent
Fournier et al.

(10) Patent No.: US 9,952,237 B2
(45) Date of Patent: Apr. 24, 2018

(54) SYSTEMS, DEVICES, AND METHODS FOR ULTRA-SENSITIVE DETECTION OF MOLECULES OR PARTICLES

(75) Inventors: David Fournier, Northborough, MA (US); Todd Campbell, Holliston, MA (US); Cheuk Kan, Boston, MA (US); John Lawson, Petersham, MA (US); Andrew Rivnak, Somerville, MA (US); Michael Kagan, Sebec, ME (US); David C. Duffy, Arlington, MA (US)

(73) Assignee: Quanterix Corporation, Lexington, MA (US)

( * ) Notice: Subject to any disclaimer, the term of this patent is extended or adjusted under 35 U.S.C. 154(b) by 1490 days.

(21) Appl. No.: 13/035,472

(22) Filed: Feb. 25, 2011

(65) Prior Publication Data

US 2012/0196774 A1    Aug. 2, 2012

Related U.S. Application Data

(60) Provisional application No. 61/437,553, filed on Jan. 28, 2011.

(51) Int. Cl.
*C12Q 1/68* (2006.01)
*G01N 35/00* (2006.01)
(Continued)

(52) U.S. Cl.
CPC ...... *G01N 35/00029* (2013.01); *B01L 3/5085* (2013.01); *B01L 3/502761* (2013.01);
(Continued)

(58) Field of Classification Search
CPC ................. G01N 21/6452; G01N 35/0043
(Continued)

(56) References Cited

U.S. PATENT DOCUMENTS 3,212,986 A   10/1965 Pennington
3,712,986 A    1/1973 Collings
(Continued)

FOREIGN PATENT DOCUMENTS

AU    199956253 B2    3/2000
CN      1635146 A     7/2005
(Continued)

OTHER PUBLICATIONS

Notice of Allowance for U.S. Appl. No. 13/527,210, filed Jun. 19, 2012, which Notice of Allowance is dated May 27, 2014, and claims as pending for U.S. Appl. No. 13/527,210 as of Nov. 20, 2013.
(Continued)

*Primary Examiner* — Jyoti Nagpaul
(74) *Attorney, Agent, or Firm* — Wolf, Greenfield & Sacks, P.C.

(57) ABSTRACT

Described are systems, devices, and methods which related to various aspects of assays for detecting and/or determining a measure of the concentration of analyte molecules or particles in a sample fluid. In some cases, the systems employ an assay consumable comprising a plurality of assay sites. The systems, devices, and/or methods, in some cases, are automated. In some cases, the systems, devices, and/or methods relate to inserting a plurality of beads into assay sites, sealing assay sites, imaging assay sites, or the like.

25 Claims, 53 Drawing Sheets

(51) Int. Cl.
*B01L 3/00* (2006.01)
*G01N 35/10* (2006.01)

(52) U.S. Cl.
CPC .. *G01N 35/1065* (2013.01); *B01L 2200/0668* (2013.01); *B01L 2200/0689* (2013.01); *B01L 2300/0803* (2013.01); *B01L 2400/043* (2013.01); *B01L 2400/086* (2013.01); *G01N 35/0098* (2013.01); *G01N 2035/00287* (2013.01)

(58) Field of Classification Search
USPC .................................................. 422/50, 500
See application file for complete search history.

(56) References Cited

U.S. PATENT DOCUMENTS

| | | | |
|---|---|---|---|
| 4,200,110 A | 4/1980 | Peterson et al. | |
| 4,232,119 A | 11/1980 | Carlsson et al. | |
| 4,284,602 A * | 8/1981 | Kelton | G01N 21/07 356/246 |
| 4,631,211 A | 12/1986 | Houghten | |
| 4,780,421 A | 10/1988 | Kameda et al. | |
| 4,883,642 A | 11/1989 | Bisconte | |
| 4,907,037 A | 3/1990 | Boisde et al. | |
| 4,924,870 A | 5/1990 | Wlodarczyk et al. | |
| 4,962,037 A | 10/1990 | Jett et al. | |
| 5,026,159 A | 6/1991 | Allen et al. | |
| 5,028,535 A | 7/1991 | Buechler et al. | |
| 5,089,391 A | 2/1992 | Buechler et al. | |
| 5,091,300 A | 2/1992 | Hurni et al. | |
| 5,108,961 A | 4/1992 | Zhong et al. | |
| 5,152,816 A | 10/1992 | Berkey | |
| 5,168,766 A | 12/1992 | Stoffel | |
| 5,190,857 A | 3/1993 | Allen et al. | |
| 5,196,306 A | 3/1993 | Bobrow et al. | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,298,741 A | 3/1994 | Walt et al. | |
| 5,315,375 A | 5/1994 | Allen | |
| 5,320,814 A | 6/1994 | Walt et al. | |
| 5,329,461 A | 7/1994 | Allen et al. | |
| 5,374,395 A | 12/1994 | Robinson et al. | |
| 5,405,783 A | 4/1995 | Pirrung et al. | |
| 5,411,858 A * | 5/1995 | McGeehan | B01L 3/5023 422/947 |
| 5,445,934 A | 8/1995 | Fodor et al. | |
| 5,468,846 A | 11/1995 | Ichikawa et al. | |
| 5,488,567 A | 1/1996 | Allen et al. | |
| 5,512,490 A | 4/1996 | Walt et al. | |
| 5,532,138 A | 7/1996 | Singh et al. | |
| 5,532,379 A | 7/1996 | Fujimoto | |
| 5,545,531 A | 8/1996 | Rava et al. | |
| 5,583,001 A | 12/1996 | Bobrow et al. | |
| 5,620,850 A | 4/1997 | Bamdad et al. | |
| 5,633,972 A | 5/1997 | Walt et al. | |
| 5,690,894 A | 11/1997 | Pinkel et al. | |
| 5,700,637 A | 12/1997 | Southern | |
| 5,731,158 A | 3/1998 | Bobrow et al. | |
| 5,770,455 A | 6/1998 | Cargill et al. | |
| 5,807,522 A | 9/1998 | Brown et al. | |
| 5,814,524 A | 9/1998 | Walt et al. | |
| 5,885,529 A | 3/1999 | Babson et al. | |
| 5,900,481 A | 5/1999 | Lough et al. | |
| 5,981,180 A | 11/1999 | Chandler et al. | |
| 6,001,564 A | 12/1999 | Bergeron et al. | |
| 6,007,690 A | 12/1999 | Nelson et al. | |
| 6,013,445 A | 1/2000 | Albrecht et al. | |
| 6,023,540 A | 2/2000 | Walt et al. | |
| 6,133,436 A | 10/2000 | Koster et al. | |
| 6,143,496 A | 11/2000 | Brown et al. | |
| 6,156,270 A | 12/2000 | Buechler | |
| 6,174,695 B1 | 1/2001 | Hammock et al. | |
| 6,207,031 B1 * | 3/2001 | Adourian | B01L 3/0275 204/450 |
| 6,210,910 B1 | 4/2001 | Walt et al. | |
| 6,266,459 B1 | 7/2001 | Walt et al. | |
| 6,285,807 B1 | 9/2001 | Walt et al. | |
| 6,327,410 B1 | 12/2001 | Walt et al. | |
| 6,329,139 B1 | 12/2001 | Nova et al. | |
| 6,368,874 B1 | 4/2002 | Gallop et al. | |
| 6,377,721 B1 | 4/2002 | Walt et al. | |
| 6,388,746 B1 | 5/2002 | Eriksson et al. | |
| 6,396,995 B1 | 5/2002 | Stuelpnagel et al. | |
| 6,406,845 B1 | 6/2002 | Walt et al. | |
| 6,432,630 B1 | 8/2002 | Blankenstein | |
| 6,482,593 B2 | 11/2002 | Walt et al. | |
| 6,582,908 B2 | 6/2003 | Fodor et al. | |
| 6,602,702 B1 | 8/2003 | McDevitt et al. | |
| 6,620,584 B1 | 9/2003 | Chee et al. | |
| 6,635,452 B1 | 10/2003 | Monforte et al. | |
| 6,667,159 B1 | 12/2003 | Walt et al. | |
| 6,713,309 B1 | 3/2004 | Anderson et al. | |
| 6,714,303 B2 | 3/2004 | Ivarsson | |
| 6,821,449 B2 | 11/2004 | Caplen et al. | |
| 6,838,051 B2 | 1/2005 | Marquiss et al. | |
| 6,858,394 B1 | 2/2005 | Chee et al. | |
| 6,859,570 B2 | 2/2005 | Walt | |
| 6,878,345 B1 | 4/2005 | Astle | |
| 6,887,431 B1 | 5/2005 | Vann et al. | |
| 6,929,924 B2 | 8/2005 | Bouanani et al. | |
| 6,942,968 B1 | 9/2005 | Dickinson et al. | |
| 6,943,034 B1 | 9/2005 | Winkler et al. | |
| 6,991,939 B2 | 1/2006 | Walt et al. | |
| 6,999,657 B2 | 2/2006 | Walt | |
| 7,056,746 B2 | 6/2006 | Seul et al. | |
| 7,060,431 B2 | 6/2006 | Chee et al. | |
| 7,115,884 B1 | 10/2006 | Walt et al. | |
| 7,211,390 B2 | 5/2007 | Rothberg et al. | |
| 7,244,559 B2 | 7/2007 | Rothberg et al. | |
| 7,250,267 B2 | 7/2007 | Walt et al. | |
| 7,264,929 B2 | 9/2007 | Rothberg et al. | |
| 7,348,181 B2 | 3/2008 | Walt et al. | |
| 7,407,630 B2 * | 8/2008 | Reed | G01N 35/028 422/552 |
| 7,480,433 B2 | 1/2009 | Walt et al. | |
| 7,572,581 B2 | 8/2009 | Gelfand et al. | |
| 7,651,841 B2 | 1/2010 | Song et al. | |
| 7,759,062 B2 | 7/2010 | Allawi et al. | |
| 7,776,553 B2 | 8/2010 | Love et al. | |
| 7,838,250 B1 | 11/2010 | Goix et al. | |
| 8,222,047 B2 | 7/2012 | Duffy et al. | |
| 8,236,574 B2 | 8/2012 | Duffy et al. | |
| 8,415,171 B2 | 4/2013 | Rissin et al. | |
| 8,460,878 B2 | 6/2013 | Walt et al. | |
| 8,460,879 B2 | 6/2013 | Walt et al. | |
| 8,492,098 B2 | 7/2013 | Walt et al. | |
| 8,846,415 B2 | 9/2014 | Duffy et al. | |
| 9,110,025 B2 | 8/2015 | Rissin et al. | |
| 9,310,360 B2 | 4/2016 | Duffy et al. | |
| 9,395,359 B2 | 7/2016 | Walt et al. | |
| 9,482,662 B2 | 11/2016 | Duffy et al. | |
| 9,551,663 B2 | 1/2017 | Rissin et al. | |
| 9,678,068 B2 | 6/2017 | Duffy et al. | |
| 2002/0009391 A1 | 1/2002 | Marquiss et al. | |
| 2002/0090650 A1 | 6/2002 | Empedocles et al. | |
| 2002/0122612 A1 | 9/2002 | Walt et al. | |
| 2003/0027126 A1 | 2/2003 | Walt et al. | |
| 2003/0082516 A1 | 5/2003 | Straus | |
| 2003/0091475 A1 | 5/2003 | Yu et al. | |
| 2003/0096243 A1 | 5/2003 | Busa | |
| 2003/0104361 A1 | 6/2003 | Weininger et al. | |
| 2003/0143580 A1 | 7/2003 | Straus et al. | |
| 2003/0198573 A1 | 10/2003 | Forood et al. | |
| 2003/0198948 A1 | 10/2003 | Stahler et al. | |
| 2004/0043502 A1 | 3/2004 | Song et al. | |
| 2004/0053322 A1 | 3/2004 | McDevitt et al. | |
| 2004/0071599 A1 | 4/2004 | Rusch et al. | |
| 2004/0072278 A1 | 4/2004 | Chou et al. | |
| 2004/0086426 A1 | 5/2004 | Vann et al. | |
| 2004/0101918 A1 | 5/2004 | Cauci | |
| 2004/0142386 A1 | 7/2004 | Rigler et al. | |

(56) References Cited

U.S. PATENT DOCUMENTS

| | | |
|---|---|---|
| 2004/0038426 A1 | 10/2004 | Manalis |
| 2004/0219074 A1* | 11/2004 | Childers ............... B01L 3/5085 422/534 |
| 2004/0248325 A1 | 12/2004 | Bukusoglu |
| 2004/0253624 A1 | 12/2004 | Smith et al. |
| 2004/0259237 A1 | 12/2004 | Kellogg et al. |
| 2005/0112634 A1 | 5/2005 | Woudenberg et al. |
| 2005/0112655 A1 | 5/2005 | Banerjee et al. |
| 2005/0129581 A1 | 6/2005 | McBride et al. |
| 2005/0130173 A1 | 6/2005 | Leamon et al. |
| 2005/0130188 A1 | 6/2005 | Walt et al. |
| 2005/0131650 A1 | 6/2005 | Andersson et al. |
| 2005/0164289 A1 | 7/2005 | Quate et al. |
| 2005/0220675 A1 | 10/2005 | Reed et al. |
| 2005/0221281 A1 | 10/2005 | Ho |
| 2005/0226780 A1 | 10/2005 | Sandell et al. |
| 2005/0244308 A1 | 11/2005 | Tanaami et al. |
| 2005/0266433 A1 | 12/2005 | Kapur et al. |
| 2006/0006067 A1 | 1/2006 | Unger |
| 2006/0013543 A1 | 1/2006 | Walt et al. |
| 2006/0040297 A1 | 2/2006 | Leamon et al. |
| 2006/0068409 A1 | 3/2006 | Phan et al. |
| 2006/0078998 A1 | 4/2006 | Puskas et al. |
| 2006/0084183 A1 | 4/2006 | Henricksen |
| 2006/0139635 A1 | 6/2006 | Kersey et al. |
| 2007/0040095 A1 | 2/2007 | Walt et al. |
| 2007/0059754 A1 | 3/2007 | Kordunsky et al. |
| 2007/0074972 A1 | 4/2007 | Nassef et al. |
| 2007/0116607 A1 | 5/2007 | Wang et al. |
| 2007/0259381 A1 | 11/2007 | Walt et al. |
| 2007/0259385 A1 | 11/2007 | Walt et al. |
| 2007/0259448 A1 | 11/2007 | Walt et al. |
| 2008/0032324 A1 | 2/2008 | Walt et al. |
| 2008/0064113 A1 | 3/2008 | Goix |
| 2008/0269069 A1 | 10/2008 | Bacher et al. |
| 2009/0036324 A1 | 2/2009 | Fan et al. |
| 2009/0087860 A1 | 4/2009 | Todd et al. |
| 2009/0142755 A1 | 6/2009 | Albitar |
| 2009/0149341 A1 | 6/2009 | Walt et al. |
| 2009/0156425 A1 | 6/2009 | Walt et al. |
| 2009/0170728 A1 | 7/2009 | Walt et al. |
| 2009/0239308 A1 | 9/2009 | Dube et al. |
| 2009/0254180 A1 | 10/2009 | Pazanowski |
| 2009/0289834 A1 | 11/2009 | Devensky |
| 2009/0307772 A1 | 12/2009 | Markham |
| 2010/0028985 A1 | 2/2010 | Hanafusa et al. |
| 2010/0075355 A1 | 3/2010 | Duffy et al. |
| 2010/0075407 A1 | 3/2010 | Duffy et al. |
| 2010/0075439 A1 | 3/2010 | Duffy et al. |
| 2010/0075862 A1 | 3/2010 | Duffy et al. |
| 2010/0140289 A1 | 6/2010 | Knobel et al. |
| 2010/0189338 A1 | 7/2010 | Lin et al. |
| 2010/0192573 A1 | 8/2010 | Hamilton et al. |
| 2010/0204335 A1 | 8/2010 | Beddingfield et al. |
| 2010/0225913 A1 | 9/2010 | Trainer |
| 2010/0227379 A1 | 9/2010 | Wo et al. |
| 2010/0329929 A1 | 12/2010 | Goix et al. |
| 2011/0037463 A1 | 2/2011 | Bertacco et al. |
| 2011/0183330 A1 | 7/2011 | Lo et al. |
| 2011/0195852 A1 | 8/2011 | Walt et al. |
| 2011/0212462 A1 | 9/2011 | Duffy et al. |
| 2011/0212537 A1* | 9/2011 | Rissin ............... G01N 21/6452 436/164 |
| 2011/0212848 A1* | 9/2011 | Duffy ............... G01N 33/54313 506/9 |
| 2011/0245097 A1 | 10/2011 | Rissin et al. |
| 2012/0183967 A1 | 7/2012 | Dressman et al. |
| 2012/0214160 A1 | 8/2012 | Deng et al. |
| 2012/0277114 A1 | 11/2012 | Duffy et al. |
| 2012/0289428 A1 | 11/2012 | Duffy et al. |
| 2013/0165342 A1 | 6/2013 | Rissin et al. |
| 2013/0345078 A1 | 12/2013 | Walt et al. |
| 2014/0094386 A1 | 4/2014 | Wilson et al. |
| 2014/0227720 A1 | 8/2014 | Wilson et al. |
| 2014/0302532 A1 | 10/2014 | Wilson et al. |
| 2015/0233905 A1 | 8/2015 | Walt et al. |
| 2015/0353997 A1 | 12/2015 | Duffy et al. |
| 2015/0355182 A1 | 12/2015 | Rissin et al. |
| 2016/0123969 A1 | 5/2016 | Rissin et al. |
| 2016/0258959 A1 | 9/2016 | Wilson et al. |
| 2017/0038390 A1 | 2/2017 | Walt et al. |
| 2017/0160292 A1 | 6/2017 | Wilson et al. |

FOREIGN PATENT DOCUMENTS

| | | |
|---|---|---|
| CN | 1950520 A | 4/2007 |
| CN | 101149376 A | 3/2008 |
| CN | 101151370 A | 3/2008 |
| CN | 101351564 A | 1/2009 |
| CN | 101529227 A | 9/2009 |
| CN | 101541974 A | 9/2009 |
| DE | 19540098 A1 | 4/1997 |
| EP | 0 510 686 A2 | 10/1992 |
| EP | 0 805 215 A2 | 11/1997 |
| EP | 1 180 679 A1 | 2/2002 |
| EP | 1 259 810 B1 | 11/2006 |
| EP | 1 721 657 A1 | 11/2006 |
| EP | 2 267 451 A2 | 12/2010 |
| JP | H05-302930 A | 11/1993 |
| JP | H09-099932 A | 4/1997 |
| JP | 2001-269196 A | 10/2001 |
| JP | 2002-506200 A | 2/2002 |
| JP | 2002-525587 | 8/2002 |
| JP | 2002-525587 A | 8/2002 |
| JP | 2002-526743 A | 8/2002 |
| JP | 2003-513257 A | 4/2003 |
| JP | 2003-517581 A | 5/2003 |
| JP | 2004-354164 A | 12/2004 |
| JP | 2005-518553 | 6/2005 |
| JP | 2005-518553 A | 6/2005 |
| JP | 2006-081416 A | 3/2006 |
| JP | 2006-511792 A | 4/2006 |
| JP | 2007-532877 A | 11/2007 |
| JP | 2009-072774 A | 4/2009 |
| JP | 2009-080106 A | 4/2009 |
| JP | 2010-510777 A | 4/2010 |
| WO | WO 88/05533 A1 | 7/1988 |
| WO | WO 93/06121 A1 | 4/1993 |
| WO | WO 93/24517 A2 | 12/1993 |
| WO | WO 95/25116 A1 | 9/1995 |
| WO | WO 95/32425 A1 | 11/1995 |
| WO | WO 95/35506 A2 | 12/1995 |
| WO | WO 97/27326 A1 | 7/1997 |
| WO | WO 98/50782 A2 | 11/1998 |
| WO | WO 99/45357 A2 | 9/1999 |
| WO | WO 99/58948 A2 | 11/1999 |
| WO | WO 00/04372 A1 | 1/2000 |
| WO | WO 00/47996 A2 | 8/2000 |
| WO | WO 01/57520 A2 | 8/2001 |
| WO | WO 03/054142 A2 | 7/2003 |
| WO | WO 03/073817 A1 | 9/2003 |
| WO | WO 2004/065000 A1 | 8/2004 |
| WO | WO 2004/083443 A1 | 9/2004 |
| WO | WO 2005/019419 A2 | 3/2005 |
| WO | WO 2005/023414 A1 | 3/2005 |
| WO | WO 2005/033283 A2 | 4/2005 |
| WO | WO 2005/054431 A2 | 6/2005 |
| WO | WO 2006/007726 A1 | 1/2006 |
| WO | WO 2006/055739 A2 | 5/2006 |
| WO | WO 2006/078289 A2 | 7/2006 |
| WO | WO 2006/102297 A1 | 9/2006 |
| WO | WO 2006/104213 A1 | 10/2006 |
| WO | WO 2006/108180 A2 | 10/2006 |
| WO | WO 2007/044091 A2 | 4/2007 |
| WO | WO 2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/084192 A2 | 7/2007 |
| WO | WO 2007/098148 A2 | 8/2007 |
| WO | WO 2007/114947 A2 | 10/2007 |
| WO | WO 2008/048371 A2 | 4/2008 |
| WO | WO 2009/029073 A1 | 3/2009 |
| WO | WO 2010/039180 A2 | 4/2010 |

(56) References Cited

FOREIGN PATENT DOCUMENTS

| WO | WO 2010/115154 A1 | 10/2010 |
|---|---|---|
| WO | WO 2011/109364 A2 | 9/2011 |
| WO | WO 2011/109372 A1 | 9/2011 |
| WO | WO 2016/115256 A1 | 7/2016 |
| WO | WO 2016/130923 A1 | 8/2016 |

OTHER PUBLICATIONS

Extended European Search Report for European Application No. 15168213.5 as of Feb. 15, 2016.
Office Communication for U.S. Appl. No. 13/530,979, filed Jun. 22, 2012, which Office Communication is dated Jun. 19, 2015, and claims as pending for U.S. Appl. No. 13/530,979 as of Apr. 5, 2013.
Office Communication for U.S. Appl. No. 13/530,979, filed Jun. 22, 2012, which Office Communication is dated Jan. 22, 2016, and claims as pending for U.S. Appl. No. 13/530,979 as of Dec. 9, 2015.
Office Communication for U.S. Appl. No. 13/530,979, filed Jun. 22, 2012, which Office Communication is dated Jan. 28, 2016, and claims as pending for U.S. Appl. No. 13/530,979 as of Dec. 9, 2015.
Office Communication for U.S. Appl. No. 13/531,061, filed Jun. 22, 2012, which Office Communication is dated Aug. 21, 2015, and claims as pending for U.S. Appl. No. 13/531,061 as of Apr. 5, 2015.
Office Communication for U.S. Appl. No. 12/731,135, filed Mar. 24, 2010, which Office Communication is dated Apr. 3, 2015, and claims as pending for U.S. Appl. No. 12/731,135 as of Nov. 22, 2013.
Office Communication for U.S. Appl. No. 13/768,843, filed Feb. 15, 2013, which Office Communication is dated Jan. 29, 2016, and claims as pending for U.S. Appl. No. 13/768,843 as of Dec. 9, 2015.
Office Communication for CN Application No. 201280012055.3, filed Jan. 27, 2012, which Office Communication is dated Feb. 17, 2015, and claims as pending for CN Application No. 201280012055.3 as of Oct. 20, 2014.
Office Communication for CN Application No. 201280012055.3, filed Jan. 27, 2012, which Office Communication is dated Oct. 21, 2015, and claims as pending for CN Application No. 201280012055.3 as of Jul. 2, 2015.
Office Communication for JP Application No. 2013-551376, filed Jan. 27, 2012, which Office Communication is dated Dec. 11, 2015, and claims as pending for JP Application No. 2013-551376 as of Jan. 27, 2015.
Office Communication for U.S. Appl. No. 13/037,987, filed Mar. 1, 2011, which Office Communication is dated Oct. 20, 2014, and claims as pending for U.S. Appl. No. 13/037,987 as of Jul. 2, 2014.
[No Author Listed], bioMérieux and Quanterix Sign Strategic Partnership in Ultrasensitive and Multiplex Immunoassays. Quanterix Press Release. Nov. 15, 2012. 2 pages.
[No Author Listed], Does Brain Hypoxia Help Kick Off Alzheimer's Pathology? Alzheimer Research Forum. Dec. 16, 2011. http://www.alzforum.org/new/detailprint.asp?id=3002 [last accessed Jan. 30, 2012]. 4 pages.
[No Author Listed], Pittcon Announces 2010 Technical Program: Webcast of Selected Symposia. Press Release. Oct. 15, 2009. http://archive.constantcontact.com/fs033/1102032821298/archive/1102745632000.html [last accessed Jan. 31, 2012]. 2 pages.
[No Author Listed], Quanterix and STRATEC Announce Strategic Partnership. Quanterix Press Release. Aug. 16, 2011. 2 pages.
[No Author Listed], Quanterix Announces Commercial Availability of its Simoa Single Molecule Array Technology. Quanterix Press Release. Jul. 30, 2013. 2 pages.
[No Author Listed], Quanterix Digital ELISA Measures Low Abundance Biomarkers of Inflammation in Crohn's Disease. Quanterix Press Release. Aug. 19, 2011. Last accessed at http://www.quanterix.com/events-news/press-releases/item/142-quanterix-digital-elisa-measures-low-abundance-biomarkers-of-inflammation-in-crohn's-disease on Sep. 20, 2012.
[No Author Listed], Quanterix Launches Multiplexed Single Molecule Immunoassay Technology to Improve Diagnosis and Potential Treatment of Complex Diseases. Quanterix Press Release. Sep. 17, 2013. 2 pages.
[No Author Listed], Quanterix to Present Poster Session on Blood-based Brain Biomarker Measurements of Sports Related Brain Injury at Neuroscience. Quanterix Press Release. Nov. 4, 2013. 1 page.
[No Author Listed], Quanterix's Simoa technology to detect blood biomarker for concussion in hockey players. Quanterix Press Release. Mar. 14, 2014. 1 page.
[No Author Listed], Quanterix's Ultrasensitive Simoa™ Technology Forges New Ground with Direct Detection of Genomic DNA in Human Blood and River Water. Quanterix Press Release. Jan. 22, 2013. 2 pages.
[No Author Listed], Quanterix's Ultrasensitive Simoa™ Technology Demonstrates Equivalence with NAT and 3,000x Improvement in Sensitivity over Conventional Immunoassays for HIV Detection. Quanterix Press Release. Oct. 11, 2012. 1 page.
[No Author Listed], Scientific Principle of Simoa™ (Single Molecule Array) Technology. Whitepaper 1.0. Jul. 19, 2013. 2 pages.
[No Author Listed], Sony DADC Develops Smart Consumables for Quanterix Simoa HD-1 Analyzer. Quanterix Press Release. Aug. 7, 2013. 2 pages.
Chang et al., Digital ELISA of HIV P24 capsid protein with sensitivity of nucleic acid amplification tests. 2012 AACC Meeting. Los Angeles, CA. Abstract Poster. 2012. 2 pages.
Chang et al., Prototype digital immunoassay for troponin I with sub-femtomolar sensitivity. 2013 AACC Meeting. Houston, TX. Abstract and Poster. 2013. 2 pages.
Chang et al., Simple diffusion-constrained immunoassay for p24 protein with the sensitivity of nucleic acid amplification for detecting acute HIV infection. J Virol Methods. Mar. 2013;188(1-2):153-60. doi: 10.1016/j.jviromet.2012.08.017. Epub Oct. 2, 2012.
Chang et al., Single molecule enzyme-linked immunosorbent assays: theoretical considerations. J Immunol Methods. Apr. 30, 2012;378(1-2):102-15. doi: 10.1016/j.jim.2012.02.011. Epub Apr. 30, 2013. 28 pages.
Duffy et al., Detection of prostate specific antigen (PSA) in the serum of radical prostatectomy patients at femtogram per milliliter levels using digital ELISA (AccuPSATM) based on single molecule arrays (SiMoA). AACC Meeting Poster. 2010. 1 page.
Duffy, Immunoassays with Broad Dynamic Ranges based on Combining Digital and Digitally Enhanced Analog Detecion of Enzyme Labels. Oak Ridge Conference. Presentation. Apr. 15, 2011. 16 pages.
Duffy, Ultra-sensitive protein detection using single molecule arrays (Simoa): the potential for detecting single molecules of botulinum toxin. The Botulinum J. 2012;2(2):164-7.
Joos, Quanterix Web Symposium: Immunoassays in Multiplex for Biomarker Discovery and Validation. Presentation. Feb. 27, 2013. 43 pages.
Okrongly, Single Molecule Enzyme Detection and Application to Immunoassay: Implications for Personalized Medicine. Abstract and Presentation. ISE International Conference. May 4, 2010. 24 pages.
Prabhakar et al., Simultaneous quantification of proinflammatory cytokines in human plasma using the LabMAP assay. J Immunol Methods. Feb. 1, 2002;260(1-2):207-18.
Rissin et al., Immunoassays with broad dynamic ranges based on combining digital and digitally-enhanced analog detection of enzyme labels. Oak Ridge Conference. Poster 7 and Abstract. Apr. 14-15, 2011. 2 pages.
Rissin et al., Multiplexed single molecule immunoassays. Lab Chip. Aug. 7, 2013;13(15):2902-11. doi: 10.1039/c3lc50416f.
Song et al., Direct Detection of Bacterial DNA and viral RNA at Subfemtomolar Concentrations Using Single Molecule Arrays (Simoa). 2013 Oakridge Conference. Baltimore, MD. Abstract and Poster. 2013. 2 pages.
Song et al., Direct detection of bacterial genomic DNA at sub-femtomolar concentrations using single molecule arrays. Anal Chem. Feb. 5, 2013;85(3):1932-9. doi: 10.1021/ac303426b. Epub Jan. 18, 2013.

(56) References Cited

OTHER PUBLICATIONS

Song et al., Single molecule measurements of tumor necrosis factor α and interleukin-6 in the plasma of patients with Crohn's disease. J Immunol Methods Sep. 30, 2011;372(1-2):177-86. Epub Jul. 27, 2011.
Tanen et al., Development of an Ultrasensitive Digital Immunoassay on the Single Molecule Array (SimoaTM) Platform. 2014 AAPS Annual Meeting. San Diego, CA. Abstract and Poster. Nov. 2-6, 2014. 2 pages.
Walt, Optical methods for single molecule detection and analysis. Anal Chem. Feb. 5, 2013;85(3):1258-63. doi: 10.1021/ac3027178. Epub Dec. 19, 2012.
Wilson et al., Development of AccuPSA™, a novel digital immunoassay for sub-femtomolar measurement of PSA in post radical prostatectomy patients. AACR Molecular diagnostics in Cancer Therapeutic Development Poster. 2011. 1 page.
Wilson et al., Fifth-generation digital immunoassay for prostate-specific antigen by single molecule array technology. Clin Chem. Dec. 2011;57(12):1712-21. Epub Oct. 13, 2011.
Wilson et al., Simoa™ HD-1: a fully automated digital immunoassay analyzer capable of single molecule counting, sub-femtomolar sensitivity, and multiplexing. 2014 AACC Meeting. Chicago, IL. Abstract and Poster. 2014. 2 pages.
Wilson, Serum Measurement of Hypoxia-Induced Amyloid Beta 1-42 Following Resuscitation from Cardiac Arrest. Abstract and Poster. American Academy of Neurology Annual Meeting. Apr. 9, 2011. 2 pages.
Yan et al., Analyzing polyubiquitin chains upon ubiquitin activating enzyme inhibition from cell culture & tumor lysates using the Quanterix's single molecule array (Simoa) technology. 2013 Society for the Laboratory Automation & Screening Annual Meeting. Orlando, FL. Abstract and Poster. 2013. 2 pages.
International Search Report and Written Opinion for International Application No. PCT/US2009/005250, dated Mar. 22, 2010.
International Preliminary Report on Patentability, Chapter 1, for International Application No. PCT/US2009/005250, dated Apr. 7, 2011.
International Search Report and Written Opinion for International Application No. PCT/US2009/005248, dated Mar. 1, 2010.
International Preliminary Report on Patentability, Chapter 1, for International Application No. PCT/US2009/005248, dated Apr. 7, 2011.
International Search Report and Written Opinion for International Application No. PCT/US2011/026645, dated Nov. 24, 2011.
International Preliminary Report on Patentability for PCT/US2011/026645 dated Sep. 13, 2012.
International Search Report and Written Opinion for International Application No. PCT/US2011/026657, dated May 24, 2011.
International Preliminary Report on Patentability for PCT/US2011/026657 dated Sep. 13, 2012.
International Search Report and Written Opinion for International Application No. PCT/US2011/026665, dated Jul. 5, 2011.
International Preliminary Report on Patentability for PCT/US2011/026665 dated Sep. 13, 2012.
Invitation to Pay Additional Fees for PCT/US2012/022923 dated Apr. 2, 2012.
International Search Report and Written Opinion for International Application No. PCT/US2012/022923 dated Jun. 25, 2012.
International Search Report and Written Opinion for International Application No. PCT/US2007/019184, dated Jun. 19, 2008.
International Preliminary Report on Patentability, Chapter 1, for International Application No. PCT/US2007/019184, dated Mar. 11, 2010.
European Search Report for European Application No. 07751131.9, dated Sep. 8, 2009.
Extended European Search Report for European Application No. 12177276.8 dated Nov. 26, 2012.
International Search Report and Written Opinion for International Application No. PCT/US2007/004349, dated Aug. 21, 2008.
International Preliminary Report on Patentability, Chapter 1, for International Application No. PCT/US2007/004349 dated Sep. 25, 2008.
International Preliminary Report on Patentability, Chapter 2, for International Application No. PCT/US2007/004349 dated Mar. 23, 2009.
Office Action for U.S. Appl. No. 12/236,484 filed Sep. 23, 2008, published as US 2010-0075862 on Mar. 25, 2010, which Office Action is dated Sep. 9, 2010, and claims as pending for U.S. Appl. No. 12/236,484 as of Sep. 9, 2010.
Office Action for U.S. Appl. No. 12/236,484 filed Sep. 23, 2008, published as US 2010-0075862 on Mar. 25, 2010, which Office Action is dated Apr. 13, 2011, and claims as pending for U.S. Appl. No. 12/236,484 as of Apr. 13, 2011.
Office Action for U.S. Appl. No. 12/236,486 filed Sep. 23, 2008, published as US 2010-0075407 on Mar. 25, 2010, which Office Action is dated Nov. 23, 2011, and claims as pending for U.S. Appl. No. 12/236,486 as of Nov. 23, 2011.
Notice of Allowance for U.S. Appl. No. 12/236,486 filed Sep. 23, 2008, published as US-2010-0075407 on Mar. 25, 2010, which Notice of Allowance is dated Mar. 22, 2012, and claims as allowed for U.S. Appl. No. 12/236,486 as of Mar. 25, 2010.
Office Action for U.S. Appl. No. 13/527,210, filed Jun. 19, 2012, which Office Action is dated Jun. 20, 2013, and claims as pending for Office Action for U.S. Appl. No. 13/527,210 as of Jun. 20, 2013.
Office Action for U.S. Appl. No. 12/236,488 filed Sep. 23, 2008, published as US 2010-0075439 on Mar. 25, 2010, which Office Action is dated Aug. 2, 2010, and claims as pending for U.S. Appl. No. 12/236,488 as of Aug. 2, 2010.
Office Action for U.S. Appl. No. 12/731,130, filed Mar. 24, 2010, published as US 2011-0212848 on Sep. 1, 2011, which Office Action is dated Mar. 28, 2012, and claims as pending for U.S. Appl. No. 12/731,130 as of Mar. 28, 2012.
Notice of Allowance for U.S. Appl. No. 12/731,130, filed Mar. 24, 2010, published as US 2011-0212848 on Sep. 1, 2011, which Notice of Allowance is dated Jun. 1, 2012, and allowed claims for U.S. Appl. No. 12/731,130 as of Jun. 1, 2012.
Office Action for U.S. Appl. No. 12/731,135, filed Mar. 24, 2010, published as US 20110212462 on Sep. 1, 2011, which Office Action is dated May 23, 2013, and claims as pending for U.S. Appl. No. 12/731,135 as of May 23, 2013.
Office Action for U.S. Appl. No. 12/731,136 filed Mar. 24, 2010, published as 2011-0212537 on Sep. 1, 2011, which Office Action is dated Jun. 15, 2012, and claims as pending for Office Action for U.S. Appl. No. 12/731,136 as of Jun. 15, 2012.
Notice of Allowance for U.S. Appl. No. 12/731,136, filed Mar. 24, 2010, published as 2011-0212537 on Sep. 1, 2011, which Notice of Allowance is dated Nov. 15, 2012, and claims as allowed for U.S. Appl. No. 12/731,136 as of Nov. 15, 2012.
Office Action for U.S. Appl. No. 11/707,385 filed Feb. 16, 2007, published as US 2007-0259448 on Nov. 8, 2007, which Office Action is dated Jan. 26, 2010, and claims as pending for U.S. Appl. No. 11/707,385 as of Jan. 26, 2010.
Office Action for U.S. Appl. No. 11/707,385 filed Feb. 16, 2007, published as US 2007-0259448 on Nov. 8, 2007, which Office Action is dated Mar. 16, 2009, and claims as pending for U.S. Appl. No. 11/707,385 as of Mar. 16, 2009.
Office Action for U.S. Appl. No. 11/707,385, filed Feb. 16, 2007, published as US 2007-0259448 on Nov. 8, 2007, which Office Action is dated Sep. 27, 2012, and claims as pending for U.S. Appl. No. 11/707,385 as of Sep. 27, 2012.
Notice of Allowance for U.S. Appl. No. 11/707,385, filed Feb. 16, 2007, published as US-2007-0259448 on Nov. 8, 2007, which Notice of Allowance is dated Feb. 25, 2013, and claims as allowed for Office Action for U.S. Appl. No. 11/707,385 as of Feb. 25, 2013.
Office Action for U.S. Appl. No. 11/707,383 filed Feb. 16, 2007, published as US 2007-0259385 on Nov. 8, 2007, which Office Action is dated Mar. 16, 2009, and claims as pending for U.S. Appl. No. 11/707,383 as of Mar. 16, 2009.
Office Action for U.S. Appl. No. 11/707,383 filed Feb. 16, 2007, published as US 2007-0259385 on Nov. 8, 2007, which Office Action is dated Nov. 27, 2009, and claims as pending for U.S. Appl. No. 11/707,383 as of Nov. 27, 2009.

(56) References Cited

OTHER PUBLICATIONS

Office Action for U.S. Appl. No. 11/707,383, filed Feb. 16, 2007, published as US 2007-0259385 on Nov. 8, 2007, which Office Action is dated Sep. 27, 2012, and claims as pending for U.S. Appl. No. 11/707,383 as of Sep. 27, 2012.
Notice of Allowance for U.S. Appl. No. 11/707,383, filed Feb. 16, 2007, published as US 2007-0259385 on Nov. 8, 2007, which Office Action is dated Feb. 8, 2013, and claims as allowed for U.S. Appl. No. 11/707,383 as of Feb. 8, 2013.
Office Action for U.S. Appl. No. 11/707,384 filed Feb. 16, 2007, published as US 2007-0259381 on Nov. 8, 2007, which Office Action is dated Mar. 16, 2009, and claims as pending for U.S. Appl. No. 11/707,384 as of Mar. 16, 2009.
Office Action for U.S. Appl. No. 11/707,384 filed Feb. 16, 2007, published as US 2007-0259381 on Nov. 8, 2007, which Office Action is dated Dec. 2, 2009, and claims as pending for U.S. Appl. No. 11/707,384 as of Dec. 2, 2009.
Office Action for U.S. Appl. No. 11/707, 384, filed Feb. 16, 2007, published as US 2007-0259381 on Nov. 8, 2007, which Office Action is dated Sep. 27, 2012, and claims as pending for U.S. Appl. No. 11/707,384 as of Sep. 27, 2012.
Notice of Allowance for U.S. Appl. No. 11/707,384, filed Feb. 16, 2007, published as US 2007-0259381 on Nov. 8, 2007, which Office Action is dated Feb. 6, 2013, and claims as allowed for U.S. Appl. No. 11/707,384 as of Feb. 6, 2013.
[No Author Listed] Novel test following prostate surgery could detect cancer recurrence earlier. AACR Press Release. Sep. 29, 2010. Last accessed at http://www.aacr.org/home/public--media/aacr-press-releases.aspx?d=2072 on Jan. 31, 2012. 2 pages.
[No Author Listed] Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.
[No Author Listed] Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.
[No Author Listed] Single molecule arrays for digital detection in complex samples. Quanterix Corporation. IQT Technology Focus Day. Mar. 25, 2010. PowerPoint presentation. 30 pages.
Adams et al., Encoded fiber-optic microsphere arrays for probing protein-carbohydrate interactions. Angewandte Chemie. 2003; 115:5475-5478.
Agrawal et al., Nanometer-scale mapping and single-molecule detection with color-coded nanoparticle probes. Proc Natl Acad Sci U S A. Mar. 4, 2008;105(9):3298-303. Epub Feb. 27, 2008.
Agrawal et al., Single-bead immunoassays using magnetic microparticles and spectral-shifting quantum dots. J Agric Food Chem. May 16, 2007; 55(10):3778-82. Epub Apr. 25, 2007.
Ahn et al., Detection of *Salmonella* spp. Using microsphere-based, fiber-optic DNA microarrays. Anal Chem. Aug. 1, 2005; 77(15):5041-7.
Ahn et al., Fiber-optic microarray for simultaneous detection of multiple harmful algal bloom species. Appl Environ Microbiol. Sep. 2006; 72(9):5742-9.
Albert et al., Automatic decoding of sensor types within randomly ordered, high-density optical sensor arrays. Anal Bioanal Chem. Apr. 2002; 373(8):792-802. Epub Jul. 27, 2002.
Albert et al., Cross-reactive chemical sensor arrays. Chem Rev. Jul. 12, 2000; 100(7):2595-626.
Albert et al., Information coding in artificial olfaction multisensor arrays. Anal Chem. Aug. 15, 2003; 75(16):4161-7.
Albert et al., Optical multibead arrays for simple and complex odor discrimination. Anal Chem. Jun. 1, 2001; 73(11):2501-8.
Angenendt et al., Subnanoliter enzymatic assays on microarrays. Proteomics. Feb. 2005;5(2):420-5.
Arnaud, Observing single enzymes at work. Chemical & Engineering News. Oct. 2007; 85(44): 8.

Beer et al., On-chip, real-time, single-copy polymerase chain reaction in picoliter droplets. Anal Chem. Nov. 15, 2007;79(22):8471-5. Epub Oct. 11, 2007. Abstract only.
Bencic-Nagale et al., Extending the longevity of fluorescence-based sensor arrays using adaptive exposure. Anal Chem. Oct. 1, 2005; 77(19):6155-62.
Bhat et al., Single molecule detection in nanofluidic digital array enables accurate measurement of DNA copy number. Anal Bioanal Chem. May 2009;394(2):457-67. Epub Mar. 15, 2009.
Biran et al., Optical imaging fiber-based live bacterial cell array biosensor. Anal Biochem. Apr. 1, 2003; 315(1):106-13.
Biran et al., Optical imaging fiber-based single live cell arrays: a high-density cell assay platform. Anal Chem. Jul. 1, 2002; 74(13):3046-54.
Blake et al., Phenotypic consequences of promoter-mediated transcriptional noise. Mol Cell. Dec. 28, 2006; 24(6):853-65.
Blicharz et al., Detection of inflammatory cytokines using a fiber optic microsphere immunoassay array. Proc. SPIE. 2006; 6380, 638010-1-638010-6.
Blicharz et al., Fiber-optic microsphere-based antibody array for the analysis of inflammatory cytokins in saliva. Anal. Chem. 2009;81(6):2106-14.
Blicharz et al., Use of colorimetric test strips for monitoring the effect of hemodialysis on salivary nitrite and uric acid in patients with end-stage renal disease: a proof of principle. Clin Chem. Sep. 2008; 54(9):1473-80. Epub Aug. 1, 2008.
Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.
Bowden et al., Development of a microfluidic platform with an optical imaging microarray capable of attomolar target DNA detection. Anal Chem. Sep. 1, 2005; 77(17):5583-8. Epub Aug. 4, 2005.
Boyden, The chemotactic effect of mixtures of antibody and antigen on polymorphonuclear leucocytes. J Exp Med. Mar. 1, 1962;115:453-66.
Brehm-Stecher et al., Single-cell microbiology: tools, technologies, and applications. Microbiol Mol Biol Rev. Sep. 2004; 68(3):538-59.
Brogan et al., Optical fiber-based sensors: application to chemical biology. Curr Opin Chem Biol. Oct. 2005; 9(5):494-500. Epub Aug. 24, 2005.
Bronk et al., Combined imaging and chemical sensing using a single optical imaging fiber. Anal Chem. Sep. 1, 1995; 67(17):2750-7.
Bronk et al., Fabrication of patterned sensor arrays with aryl azides on a polymer-coated imaging optical fiber bundle. Anal Chem. Oct. 15, 1994; 66(20):3519-20.
Burton et al., A microfluidic chip-compatible bioassay based on single-molecule detection with high sensitivity and multiplexing. Lab Chip. Apr. 7, 2010; 10(7):843-51. Epub Jan. 14, 2010.
Campian, Colored and fluorescent solid supports. Innovation and Perspectives in Solid Phase Synthesis. Ed. R. Epton, Mayflower Worldwide Limited, Birmingham. Ch. 77. 1994:469-472.
Chen et al., Microfabricated arrays of cylinrical wells facilitate single-molecule enzymology of alpha-chymotrypsin. Biotechnol Prog. Jul.-Aug. 2009; 25(4):929-37.
Chin et al., Editor's Choice: Distinctive individualism. Science. Apr. 4, 2008;320:21.
Chon et al., Characterization of single-cell migration using a computer-aided fluorescence time-lapse videomicroscopy system. Anal Biochem. Oct. 15, 1997;252(2):246-54.
Deutsch et al., Apparatus for high-precision repetitive sequential optical measurement of living cells. Cytometry. Jul. 1, 1994; 16(3):214-26.
Dicesare et al., Individual cell migration analysis using fiber-optic bundles. Anal Bioanal Chem. May 2005;382(1):37-43, Epub Apr. 1, 2005.
Dickinson et al., A chemical-detecting system based on a cross-reactive optical sensor array. Nature. Aug. 22, 1996; 382(6593):697-700.
Dickinson et al., Convergent, self-encoded bead sensor arrays in the design of an artificial. Anal Chem. Jun. 1, 1999; 71(11):2192-8.
Dickinson et al., Current trends in 'artificial-nose' technology. Trends Biotechnol. Jun. 1998; 16(6):250-8.

(56) References Cited

OTHER PUBLICATIONS

Duffy. Single Molecule Arrays (Simoa) for Ultrasensitive Protein Detection in Companion Diagnostics. Next Generation DX Summit. Aug. 22, 2012. PowerPoint presentation.
Egner et al., Tagging in combinatorial chemistry: the use of coloured and fluorescent beads. Chem Commun. 1997; 735-736.
Eid et al., Real-time DNA sequencing from single polymerase molecules. Science. Jan. 2, 2009; 323(5910):133-8. Epub Nov. 20, 2008.
Ekins et al., Single-molecule ELISA. Clin Chem. Mar. 2011;57(3):372-5. Epub Oct. 13, 2010. Papers in press. Oct. 13, 2010. pp. 1-3.
English et al., Ever-fluctuating single enzyme molecules: Michaelis-Menten equation revisited. Nat Chem Biol. Feb. 2006; 2(2):87-94. Epub Dec. 25, 2005.
Epstein et al., Combinatorial decoding: an approach for universal DNA array fabrication. J Am Chem Soc. Nov. 12, 2003; 125(45):13753-9.
Epstein et al., Fluorescence-based nucleic acid detection and microarrays. Analytica Chimica Acta. 2002; 469:3-36.
Epstein et al., High-density fiber-optic genosensor microsphere array capable of zeptomole detection limits. Anal Chem. Apr. 15, 2002; 74(8):1836-40.
Epstein et al., High-density, microsphere-based fiber optic DNA microarrays. Biosens Bioelectron. May 2003; 18(5-6):541-6.
Epstein, et al., Fluorescence-based fibre optic arrays: a universal platform for sensing. Chem Soc Rev. Jul. 2003; 32(4):203-14.
Ferguson et al., A fiber-optic DNA biosensor microarray for the analysis of gene expression. Nat Biotechnol. Dec. 1996; 14(13):1681-4.
Ferguson et al., High-density fiber-optic DNA random microsphere array. Anal Chem. Nov. 15, 2000; 72(22):5618-24.
Ferguson et al., Simultaneous monitoring of pH, $CO_2$ and $O_2$ using an optical imaging fiber. Analytica Chimica Acta. 1997; 340(1-3):123-131.
Fister et al., Counting single chromophore molecules for ultrasensitive analysis and separations on microchip devices. Analytical Chemistry. 1998; 70:431-437.
Fulton et al., Advanced multiplexed analysis with the FlowMetrix system. Clin Chem. Sep. 1997; 43(9):1749-56.
Furka et al., General method for rapid synthesis of multicomponent peptide mixtures. Int J Pept Protein Res. Jun. 1991;37(6):487-93.
Gebel, Molecule counting made easy. Anal Chem. Sep. 1, 2009; 7130-7131.
Giaever et al., Micromotion of mammalian cells measured electrically. Proc Natl Acad Sci U S A. Sep. 1, 1991;88(17):7896-900.
Gorris et al., Analytical chemistry on the femtoliter scale. Angew Chem Int Ed. 2010; 49:2-18.
Gorris et al., Mechanistic aspects of horseradish peroxidase elucidated through single-molecule studies. J Am Chem Soc. May 6, 2009; 131(17):6277-82.
Gorris et al., Optical-fiber bundles. FEBS J. Nov. 2007; 274(21):5462-70. Epub Oct. 12, 2007.
Gorris et al., Stochastic inhibitor release and binding from single-enzyme molecules. Proc Natl Acad Sci U S A. Nov. 6, 2007; 104(45):17680-5. Epub Oct. 26, 2007.
Härma et al., Europium nanoparticles and time-resolved fluorescence for ultrasensitive detection of prostate-specific antigen. Clin Chem. Mar. 2001; 47(3):561-8.
Härma et al., Miniature single-particle immunoassay for prostate-specific antigen in serum using recombinant Fab fragments. Clin Chem. Nov. 2000; 46(11):1755-61.
Härma et al., Zeptomole detection sensitivity of prostate-specific antigen in a rapid microtitre plate assay using time-resolved fluorescence. Luminescence. Nov.-Dec. 2000;15(6):351-5.
Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. Clin Diagn Lab Immunol. Sep. 1995; 2(5):535-41.

Haugland, Handbook: A Guide to Fluorescent Probes and Labeling Technologies. Invitrogen, Eugene, OR. Molecular Probes, US. Pages 473-538.
He et al., Selective encapsulation of single cells and subcellular organelles into picoliter- and femtoliter-volume droplets. Anal Chem. Mar. 15, 2005; 77(6):1539-44.
Healey et al., Fiberoptic DNA sensor array capable of detecting point mutations. Anal Biochem. Sep. 5, 1997; 251(2):270-9.
Healey et al., Multianalyte biosensors on optical imaging bundles. Biosens Bioelectron. 1997; 12(6):521-9.
Healey et al., Photodeposition of micrometer-scale polymer patterns on optical imaging fibers. Science. Aug. 25, 1995; 269(5227):1078-80.
Hindson et al., High-throughput droplet digital PCR system for absolute quantitation of DNA copy number. Anal Chem. Nov. 15, 2011;83(22):8604-10. Epub Oct. 28, 2011.
Hirano et al., A novel method for DNA molecular counting. Nucleic Acids Symp Ser. 2000;(44):157-8.
Hirschfeld, Remote and in-situ analysis. Anal Chem. 1986; 324:618-624.
Hunsaker et al., Nucleic acid hybridization assays employing dA-tailed capture probes. II. Advanced multiple capture methods. Anal Biochem. Sep. 1989; 181(2):360-70.
Johnson et al., Identification of multiple analytes using an optical sensor array and pattern recognition neural networks. Analytical Chemistry. 1997; 69(22):4641-8.
Kiss et al., High-throughput quantitative polymerase chain reaction in picoliter droplets. Anal Chem. Dec. 1, 2008;80(23):8975-81.
Kremsky et al., Immobilization of DNA via oligonucleotides containing an aldehyde or carboxylic acid group at the 5' terminus. Nucleic Acids Res. Apr. 10, 1987; 15(7):2891-909.
Kuang et al., Living bacterial cell array for genotoxin monitoring. Anal Chem. May 15, 2004; 76(10):2902-9.
Kuang et al., Monitoring "promiscuous" drug effects on single cells of multiple cell types. Anal Biochem. Oct. 15, 2005; 345(2):320-5.
Kuang et al., Simultaneously monitoring gene expression kinetics and genetic noise in single cells by optical well arrays. Anal Chem. Nov. 1, 2004; 76(21):6282-6.
Lafratta et al., Very high density sensing arrays. Chem Rev. Feb. 2008; 108(2):614-37. Epub Jan. 30, 2008.
Lee et al., A fiber-optic microarray biosensor using aptamers as receptors. Anal Biochem. Jun. 15, 2000; 282(1):142-6.
Li et al., Detection of single-molecule DNA hybridization using enzymatic amplification in an array of femtoliter-sized reaction vessels. J Am Chem Soc. Sep. 14, 2008; 130(38):12622-3. Epub Sep. 3, 2008.
Li et al., Molecule by molecule direct and quantitative counting of antibody-protein complexes in solution. Anal Chem. Aug. 1, 2004; 76(15):4446-51.
Lu et al., Single-molecule enzymatic dynamics. Science. Dec. 4, 1998; 282(5395):1877-82.
Luo et al., Single-molecule and ensemble fluorescence assays for a functionally important conformational change in T7 DNA polymerase. Proc Natl Acad Sci U S A. Jul. 31, 2007; 104(31):12610-5. Epub Jul. 18, 2007.
Melin et al., Microfluidic large-scale integration: the evolution of design rules for biological automation. Annu Rev Biophys Biomol Struct. 2007; 36:213-31.
Michael et al., Combined imaging and chemical sensing of fertilization-induced acid release from single sea urchin eggs. Anal Biochem. Sep. 10, 1999; 273(2):168-78.
Michael et al., Randomly ordered addressable high-density optical sensor arrays. Anal Chem. Apr. 1, 1998; 70(7):1242-8.
Monk et al., Fabrication of gold microtubes and microwires in high aspect ratio capillary arrays. J Am Chem Soc. Sep. 22, 2004;126(37):11416-7.
Monk et al., Optical fiber-based biosensors. Anal Bioanal Chem. Aug. 2004; 379(7-8):931-45. Epub Jun. 23, 2004.
Monk et al., Progress toward the dermination of $Sr^{2+}$ in highly basic solutions using imagining optical fiber sensor arrays. J. Mater. Chem. 2005; 15:4361-4366.
Morrison et al., Nanoliter high throughput quantitative PCR. Nucleic Acids Res. 2006;34(18):e123. Epub Sep. 25, 2006.

(56) References Cited

OTHER PUBLICATIONS

Munkholm et al., Polymer modification of fiber optic chemical sensors as a method of enhancing fluroescence signal for pH measurement. Anal Chem. 1986; 58:1427-1430.
Nagai et al., High-throughput PCR in silicon based microchamber array. Biosens Bioelectron. Dec. 2001; 16(9-12):1015-9.
Nalefski et al., Single-molecule detection for femtomolar quantification of proteins in heterogeneous immunoassays. Clin Chem. Nov. 2006; 52(11):2172-5.
Nam et al., Nanoparticle-based bio-bar codes for the ultrasensitive detection of proteins. Science. Sep. 26, 2003;301(5641):1884-6.
Niemeyer et al., Combination of DNA-directed immobilization and immuno-PCR: very sensitive antigen detection by means of self-assembled DNA-protein conjugates. Nucleic Acids Res. Aug. 15, 2003; 31(16):e90, 7 pages.
Panova et al., In situ fluorescence imaging of localized corrosion with a pH-sensitive imaging fiber. Anal Chem. Apr. 15, 1997; 69(8):1635-41.
Pantano et al., Analytical applications of optical imaging fibers. Anal Chem. Aug. 1, 1995; 67(15):481A-487A.
Pantano et al., Ordered nanowell arrays. Chemistry of Materials. 1996;8: 2832-2835.
Pantano et al., Toward a near-field optical array. Rev. Sci. Instrum. 1997; 68(3) 1357-1359.
Peterson et al., Fiber optic pH probe for physiological use. Anal Chem. May 1980; 52(6):864-9.
Qiu et al., Fluorescence single-molecule counting assays for high-sensitivity detection of cytokines and chemokines. Clin Chem. Nov. 2007; 53(11):2010-2.
Randle et al., Integrating molecular detection and response to create self-signalling antibodies. Biochem Biophys Res Commun. Nov. 12, 2004; 324(2):504-10.
Rissin et al., Attomolar detection of proteins in serum using single molecule enzyme-linked immunosorbent assays. Quanterix Corporation. Oak Ridge Conference, San Jose, CA. Poster. 2010. 1 page.
Rissin et al., Digital concentration readout of single enzyme molecules using femtoliter arrays and Poisson statistics. Nano Lett. Mar. 2006; 6(3):520-3.
Rissin et al., Digital readout of target binding with attomole detection limits via enzyme amplification in femtoliter arrays. J Am Chem Soc. May 17, 2006; 128(19):6286-7.
Rissin et al., Distinct and long-lived activity states of single enzyme molecules. J Am Chem Soc. Apr. 16, 2008; 130(15):5349-53. Epub Mar. 5, 2008.
Rissin et al., Duplexed sandwich immunoassays on a fiber-optic microarray. Anal Chim Acta. Mar. 30, 2006; 564(1):34-9. Epub Nov. 11, 2005.
Rissin et al., Single-molecule enzyme-linked immunosorbent assay detects serum proteins at subfemtomolar concentrations. Nat Biotechnol. Jun. 2010; 28(6):595-9 and supplemental pages. Epub May 23, 2010.
Roeffaers et al., Single-molecule fluorescence spectroscopy in (bio)catalysis. Proc Natl Acad Sci U S A. Jul. 31, 2007; 104(31):12603-9. Epub Jul. 30, 2007.
Rondelez et al., Highly coupled ATP synthesis by F1-ATPase single molecules. Nature. Feb. 17, 2005; 433(7027):773-7.
Rondelez et al., Microfabricated arrays of femtoliter chambers allow single molecule enzymology. Nat Biotechnol. Mar. 2005; 23(3):361-5. Epub Feb. 20, 2005.
Rotman, Measurement of activity of single molecules of beta-D-galactosidase. Proc Natl Acad Sci U S A. Dec. 15, 1961; 47:1981-91.
Schauer et al., A cross-reactive, class-selective enzymatic array assay. J Am Chem Soc. Sep. 26, 2001; 123(38):9443-4.
Schmidinger, et al., Inhibitor and protein microarrays for activity-based recognition of lipolytic enzymes. Chembiochem. Mar. 2006; 7(3):527-34.
Schweitzer et al., Inaugural article: immunoassays with rolling circle DNA amplification: a versatile platform for ultrasensitive antigen detection. Proc Natl Acad Sci U S A. Aug. 29, 2000; 97(18):10113-9.
Seydack, Nanoparticle labels in immunosensing using optical detection methods. Biosens Bioelectron. Jun. 15, 2005; 20(12):2454-69. Epub Dec. 16, 2004.
Shen et al. High-throughput SNP genotyping on universal bead arrays. Mutat Res. Jun. 3, 2005;573(1-2):70-82.
Shephard et al., Array-based binary analysis for bacterial typing. Anal Chem. Jan. 1, 2005; 77(1):319-26.
Song et al., Detecting biological warfare agents. Emerg Infect Dis. Oct. 2005; 11(10):1629-32.
Song et al., Fiber-optic microsphere-based arrays for multiplexed biological warfare agent detection. Anal Chem. Feb. 15, 2006; 78(4):1023-33.
Soukka et al., Supersensitive time-resolved immunofluorometric assay of free prostate-specific antigen with nanoparticle label technology. Clin Chem. 2001; 47(7):1269-78.
Stamou et al., Self-assembled microarrays of attoliter molecular vessels. Angew Chem Int Ed Engl. Nov. 24, 2003; 42(45):5580-3.
Steemers et al., Multi-analyte sensing: from site-selective deposition to randomly ordered addressable optical sensors. Microchimica Acta. 1999; 131:99-105.
Steemers et al., Screening unlabeled DNA targets with randomly ordered fiber-optic gene arrays. Nat Biotechnol. Jan. 2000; 18(1):91-4.
Stitzel et al., Array-to-array transfer of an artificial nose classifier. Anal Chem. Nov. 1, 2001; 73(21):5266-71. Epub. Sep. 28, 2001.
Subbaraman, Detecting single cancer molecules. Technol Rev. Jun. 3, 2010. Last accessed at http://www.technologyreview.com/biomedicine/25462/ on Jan. 31, 2012. 1 page.
Sykes et al., Quantitation of targets for PCR by use of limiting dilution. Biotechniques. 1992;13(3):444-9.
Szunerits et al., "Aluminum Surface Corrosion and the Mechanism of Inhibitors Using pH and Metal Ion Selective Imaging Fiber Bundles," *Analytical Chemistry*, 2002, 74(4), 886-894.
Szunerits et al., "Fabrication of an Optoelectrochemical Microring Array," *Analytical Chemistry*, 2002, 74(7), 1718-1723.
Szunerits et al., Spatially resolved electrochemiluminescence on an array of electrode tips. Anal Chem. Sep. 1, 2003; 75(17):4382-8.
Szunerits et al., The use of optical fiber bundles combined with electrochemistry for chemical imaging. Chemphyschem. Feb. 17, 2003; 4(2):186-92. Epub Feb. 7, 2003.
Szurdoki et al., A duplexed microsphere-based fluorescent immunoassay. Anal Biochem. Apr. 15, 2001; 291(2):219-28.
Tam et al., An imaging fiber-based optical tweezer array for microparticle array assembly. Applied Physics Letters. 2004; 84(21):4289-4291.
Tam et al., Fabrication and optical characterization of imaging fiber-based nanoarrays. Talanta. Sep. 15, 2005; 67(3):498-502. Epub Jul. 27, 2005.
Tam et al., Parallel microparticle manipulation using an imaging fiber bundle-based optical tweezer array and a digital micromirror device. Applied Physics Letters. 2006; 89:194101/1-194101/3.
Tan et al., Monitoring the reactions of single enzyme molecules and single metal ions. Anal. Chem. 1997; 69:4242-4248.
Taylor et al., Application of high-density optical microwell arrays in a live-cell biosensing system. Anal Biochem. Feb. 15, 2000; 278(2):132-42.
Tessler et al., Protein quantification in complex mixtures by solid phase single-molecule counting. Anal Chem. Sep. 1, 2009; 81(17):7141-8.
Thaxton et al., Nanoparticle-based bio-barcode assay redefines "undetectable" PSA and biochemical recurrence after radical prostatectomy. Proc Natl Acad Sci U S A. Nov. 3, 2009;106(44):18437-42. Epub Oct. 19, 2009.
Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/ on Jan. 31, 2012. 4 pages.

(56) References Cited

OTHER PUBLICATIONS

Todd et al., Ultrasensitive flow-based immunoassays using single-molecule counting. Clin Chem. Nov. 2007; 53(11):1990-5. Epub Sep. 21, 2007.
Tromberg et al., Development of antibody-based fiber-optic sensors for detection of a benzo[a]pyrene metabolite. Anal Chem. Sep. 15, 1988; 60(18):1901-8.
Ueberfeld et al., Reversible ratiometric probe for quantitative DNA measurements. Anal Chem. Feb. 15, 2004; 76(4):947-52. Epub Jan. 20, 2004.
Vo-Dinh et al., Phase-resolved fiber-optics fluoroimmunosensor. Applied Spectroscopy. 1990; 44(1):128-132.
Vogelstein et al., Digital PCR. Proc Natl Acad Sci U S A. Aug. 3, 1999;96(16):9236-41.
Walt et al., Biosensing with live cells using a high-density optical fiber array. Radiation Research. 2001; 156(4):442.
Walt et al., Microsensor arrays for saliva diagnostics. Ann N Y Acad Sci. Mar. 2007; 1098:389-400.
Walt et al., Optical sensor arrays for odor recognition. 13(6):697-9. *Biosens Bioelectron.* Sep. 15, 1998; 13(6):697-9.
Walt et al., Ultrasensitive detection of proteins using single molecule arrays (SiMoA). Presented Mar. 1, 2010. Pittcon. Abstract and PowerPoint presentation. 32 pages.
Walt, An array of solutions, fiber arrays contribute to studies of individual cellular behavior and response. SPIE'S oemagazine. 2005; 19-21.
Walt, Fiber optic array biosensors. Biotechniques. Nov. 2006; 41(5):529, 531, 533, 535 passim.
Walt, Fiber optic imaging sensors. Accounts of Chemical Research. 1998; 31:267-278.
Walt, Imaging optical sensor arrays. *Curr Opin Chem Biol.* Oct. 2002; 6(5):689-95.
Walt, Techview: molecular biology. Bead-based fiber-optic arrays. *Science.* Jan. 21, 2000; 287(5452):451-2.
Wang et al., Quantification of protein based on single-molecule counting by total internal reflection fluorescence microscopy with adsorption equilibrium. *Anal Chim Acta.* May 2, 2007; 590(1):104-9. Epub Mar. 15, 2007.
Warren et al., Transcription factor profiling in individual hematopoietic progenitors by digital RT-PCR. Proc Natl Acad Sci U S A. Nov. 21, 2006;103(47):17807-12. Epub Nov. 10, 2006.
Whitaker et al., Fiber-based single cell analysis of reporter gene expression in yeast two-hybrid systems. *Anal Biochem.* Jan. 1, 2007; 360(1):63-74. Epub Oct. 30, 2006.
Whitaker et al., Multianalyte single-cell analysis with multiple cell lines using a fiber-optic array. *Anal Chem.* Dec. 1, 2007; 79(23):9045-53. Epub Nov. 1, 2007.
White et al., An olfactory neuronal network for vapor recognition in an artificial nose. *Biol Cybern.* Apr. 1998;78(4):245-51.
White et al., Rapid analyte recognition in a device based on optical sensors and the olfactory system. Analytical Chemistry. 1996; 68(13):2191-2202.
Wu et al., Development and preliminary clinical validation of a high sensitivity assay for cardiac troponin using a capillary flow (single molecule) fluorescence detector. *Clin Chem.* Nov. 2006; 51(11):2157-9.

Xie et al., Optical studies of single molecules at room temperature. *Annu Rev Phys Chem.* 1998; 49:441-80.
Xie et al., Single gold nanoparticles counter: an ultrasensitive detection platform for one-step homogenous immunoassays and DNA hybridization assays. J Am Chem Soc. Sep. 9, 2009;131(35):12763-70.
Xue et al., Differences in the chemical reactivity of individual molecules of an enzyme. *Nature.* Feb. 23, 1995; 373(6516):681-3.
Young et al., Integrating high-content screening and ligand-target prediction to identify mechanism of action. Nat Chem Biol. Jan. 2008; 4(1):59-68. Epub Dec. 9, 2007.
Office Communication for U.S. Appl. No. 12/731,135, filed Mar. 24, 2010, which Office Communication is dated Mar. 29, 2016, and claims as pending for U.S. Appl. No. 12/731,135 as of Sep. 3, 2015.
Office Action for U.S. Appl. No. 13/527,210, filed Feb. 6, 2014, which Office Action is dated Jun. 20, 2013, and claims as pending for Office Action for U.S. Appl. No. 13/527,210 as of Nov. 20, 2013.
Office Communication for U.S. Appl. No. 13/037,987, filed Mar. 1, 2011, which Office Communication is dated May 2, 2014, and claims as pending for U.S. Appl. No. 13/037,987.
International Preliminary Report on Patentability for PCT/US2012/022923 dated Aug. 8, 2013.
[No Author Listed] Quanterix Develops Microfluidic Consumable That Will Enable Next Generation Molecular Diagnostic Systems Based on Single Molecule Array Technology. Quanterix Press Release. Dec. 22, 2011. Last accessed at http://www.quanterix.com/events-news/press-releases/item/136-quanterix-develops-microfluidic-consumable-that-will-enable-next-generation-molecular-diagnostic-systems-based-on-single-molecule-array-technology on Sep. 20, 2012.
[No Author Listed] Quanterix and Sony DADC to Develop and Manufacture Smart Consumables for Life Science and In Vitro Diagnostic Applications. Quanterix Press Release. Jul. 20, 2011. Last accessed at http://www.quanterix.com/events-news/press-releases/item/145-quanterix-and-sony-dadc-to-develop-and-manufacture-smart-consumables-for-life-science-and-in-vitro-diagnostic-applications on Sep. 20, 2012.
Chang et al. Digital ELISA for HIV P24 capsid protein with sensitivity of nucleic acid amplification tests. Poster presented at AACC Annual Meeting. Jul. 19, 2012. 1 page.
Kan et al.. Automation of assays based on single molecule arrays: development of a flow-cell based procedure on microfabricated polymer array assemblies. Pister presented at AACC Annual Meeting. Jul. 17, 2012. 1 page.
Rissin et al., Simultaneous detection of single molecules and singulated ensembles of molecules enables immunoassays with broad dynamic range. Anal Chem. Mar. 15, 2011;83(6):2279-85. Epub Feb. 23, 2011.
Walt, Single Molecule Detection Technology in Clinical Analysis. AACC Annual Meeting. Jul. 18, 2012. PowerPoint presentation. 38 slides.
Office Communication for CN Application No. 201280012055.3, filed Jan. 27, 2012, which Office Communication dated Jun. 5, 2014, and claims as pending for Chinese Application No. 201280012055.3 as of Jan. 27, 2012.

\* cited by examiner

*Actuation via an actuation medium*

SYSTEMS, DEVICES, AND METHODS FOR ULTRA-SENSITIVE DETECTION OF MOLECULES OR PARTICLES

RELATED APPLICATIONS

This application claims the benefit of U.S. Provisional Patent Application Ser. No. 61/437,553, filed Jan. 28, 2011, entitled "Systems, Devices, and Methods for Ultra-Sensitive Detection of Molecules or Particles," by Fournier et al., herein incorporated by reference.

FIELD OF THE INVENTION

Described are systems, devices, and methods which related to various aspects of assays for detecting and/or determining a measure of the concentration of analyte molecules or particles in a sample fluid. In some cases, the systems employ an assay consumable comprising a plurality of assay sites. The systems, devices, and/or methods, in some cases, are automated.

BACKGROUND OF THE INVENTION

Methods and systems that are able to quickly and accurately detect and, in certain cases, quantify a target analyte molecule in a sample are the cornerstones of modern analytical measurements. Such systems and/or methods are employed in many areas such as academic and industrial research, environmental assessment, food safety, medical diagnosis, and detection of chemical, biological, and/or radiological warfare agents. Advantageous features of such techniques may include specificity, speed, and sensitivity.

Most current techniques for quantifying low levels of analyte molecules in a sample use amplification procedures to increase the number of reporter molecules in order to be able to provide a measurable signal. One feature of many known methods and/or systems for detecting or quantifying low concentrations of a particular analyte in solution is that they are based on ensemble responses in which many analyte molecules give rise to a measured signal. Most detection schemes require that a large number of molecules are present in the ensemble for the aggregate signal to be above the detection threshold. This requirement limits the sensitivity of most detection techniques and the dynamic range (i.e., the range of concentrations that can be detected). Many of the known methods and techniques are further plagued with problems of non-specific binding, which is the binding of analyte or non-analyte molecules or particles to be detected or reporter species non-specifically to sites other than those expected. This leads to an increase in the background signal, and therefore limits the lowest concentration that may be accurately or reproducibly detected.

While various methods and/or systems are known in the art for detection and/or determining the concentration of analyte molecules in a sample fluid, there is need for improved systems and/or methods which operated with accurate quantification of low concentrations, and systems which are automated.

Accordingly, improved methods and/or systems are needed.

SUMMARY OF THE INVENTION

In some embodiments, an apparatus for performing an assay is provided comprising an assay consumable handler configured to be operatively coupled to an assay consumable having a surface comprising a plurality of assay sites; a sealer constructed and positioned to apply a sealing component to the surface of the assay consumable; a sample loader configured to load an assay sample into at least a portion of the plurality of assay sites of the assay consumable; an imaging system configured to acquire an image of at least a portion of the assay sites of the assay consumable containing assay sample; and a computer implemented control system configured to automatically operate the sealer and receive information from the imaging system related to the image.

In some embodiments, an apparatus for sealing a plurality of assay sites is provided comprising an assay consumable handler configured to be operatively coupled to an assay consumable having a surface comprising a plurality of assay sites; a sealer constructed and positioned to apply a sealing component to the surface of the assay consumable to form a plurality of sealed assay sites, wherein the contents of each sealed assay site is substantially isolated from the contents of each of the other plurality of sealed assay sites; and a controller configured to automatically operate the sealer to apply the sealing component to the plurality of assay sites.

In some embodiments, an apparatus for inserting beads into assay sites on an assay consumable is provided comprising an assay consumable handler configured to be operatively coupled to an assay consumable having a surface comprising a plurality of assay sites; a bead loader configured to insert individual beads into individual assay sites, such that each assay site containing a bead will contain no more than one bead; and a controller configured to automatically operate the bead loader to insert individual beads into individual assay sites.

In some embodiments, an apparatus for performing an assay is provided comprising an assay consumable handler configured to be operatively coupled to an assay consumable having a surface comprising a plurality of assay sites; a sample loader configured to load an assay sample containing analyte molecules or particles having an unknown concentration to be measured into at least a portion of the plurality of assay sites, such that a plurality of assay sites into which assay sample is loaded contain either zero or a single analyte molecule or particle; a detector configured to interrogate at least a portion of the assay sites containing assay sample and determine a fraction of the plurality of assay sites interrogated that contain an analyte molecule or particle; and a computer implemented system configured receive information from the detector and from the information determine a measure of the unknown concentration of the analyte molecules or particles in the assay sample.

In some embodiments, an apparatus for inserting beads into assay sites on an assay consumable is provided comprising an assay consumable handler configured to be operatively coupled to the assay consumable, wherein the assay consumable comprises a surface comprising a plurality of the assay sites; a bead applicator configured to apply a plurality of magnetic beads to the surface of the assay consumable or place a plurality of magnetic beads in close proximity to the surface; a bead loader comprising a magnetic field generator positioned adjacent to the assay consumable and configured to create relative motion between the magnetic beads and the assay sites; and a controller configured to automatically operate the bead loader to create relative motion between the magnetic beads and the assay sites and insert beads into assay sites.

In some embodiments, an apparatus for removing excess beads from an assay consumable having a surface comprising a plurality of assay sites is provided comprising a assay consumable handler operatively coupled to the assay consumable, wherein the assay consumable comprises a plurality of beads, wherein a first portion of the beads are contained in the assay sites and a second portion of the beads are positioned on the surface of the assay consumable, but not contained within an assay site; a wiper configured to remove substantially all of the second portion of beads from the surface; and a controller configured to automatically operate the wiper to remove the second portion of the beads.

In some embodiments, an assay consumable is provided comprising a surface comprising a plurality of assay sites, wherein each of the assay sites has a volume between about 10 attoliters and about 50 picoliters; and at least one channel formed in the surface at least partially surrounding the plurality of assay sites that is positioned and configured to collect excess assay sample liquid applied to the surface that overflows the assay sites.

In some embodiments, an automated method for forming a plurality of sealed assay sites for performing an assay is provided comprising operatively associating an assay consumable having a surface comprising a plurality of assay sites with a sealer apparatus comprising a sealer and a controller; and applying a sealing component to the plurality of assay sites with the sealer apparatus such that a plurality of sealed assay sites are formed, wherein the contents of each sealed assay site is substantially isolated from the contents of each of the other plurality of sealed assay sites.

In some embodiments, a method for inserting beads into reaction vessels on an assay consumable is provided comprising generating a magnetic field in proximity to a surface of the assay consumable comprising a plurality of the reaction vessels such that a magnetic field vector of the magnetic field is directed from the surface towards a bottom of the reaction vessels and/or towards the perimeter of the surface; delivering a plurality of magnetic beads in proximity to the surface; and creating relative motion between the magnetic beads and the reaction vessels.

In some embodiments, a method for forming a plurality of sealed reaction vessels for performing an assay is provided comprising associating an assay consumable having a surface comprising a plurality of assay sites with a sealing component by applying the sealing component to the surface, wherein the contents of each assay site are substantially isolated from the contents of each of the other plurality of assay sites following association of the sealing component without maintaining any pressure applied to the sealing component, and wherein each of the assay sites has a volume between about 10 attoliters and about 50 picoliters.

In some embodiments, a method for forming a plurality of sealed reaction vessels for performing an assay is provided comprising associating an assay consumable having a surface comprising a plurality of assay sites with a sealing component by applying the sealing component to the surface of the assay consumable and applying pressure to the sealing component, wherein the contents of each assay site are substantially isolated from the contents of each of the other plurality of assay sites following association of the sealing component with the assay consumable; wherein the sealing component comprises a pressure-sensitive adhesive such that the pressure-sensitive adhesive is activated upon application of the pressure to the sealing component and the adhesive forms an adhesive bond between the sealing component and the surface of the assay consumable; and wherein each of the assay sites has a volume between about 10 attoliters and about 50 picoliters.

In some embodiments, a method for forming a plurality of sealed assay sites for performing an assay is provided comprising providing an assay consumable having a surface comprising a plurality of assay sites wherein each of the assay sites has a volume between about 10 attoliters and about 50 picoliters; and applying a liquid that is substantially immiscible with liquid contained in the plurality of assay sites to the plurality of assay sites such that a plurality of sealed assay sites are formed, wherein the contents of each sealed assay site is substantially isolated from the contents of each of the other plurality of sealed assay sites.

In some embodiments, an apparatus for removing beads from a surface of an assay consumable is provided comprising a first magnet, wherein the first magnet is located adjacent to a surface of the assay consumable and is positioned opposite the surface comprising the plurality of assay sites, a second magnet, a third magnet, and a metal object, wherein the second magnet and third magnet are located adjacent the surface comprising the plurality of assay sites and such that the opposite poles of the second magnet and the third magnet are directed towards each other; and wherein the metal object is positioned between the second magnet and the third magnet.

Figure 1:
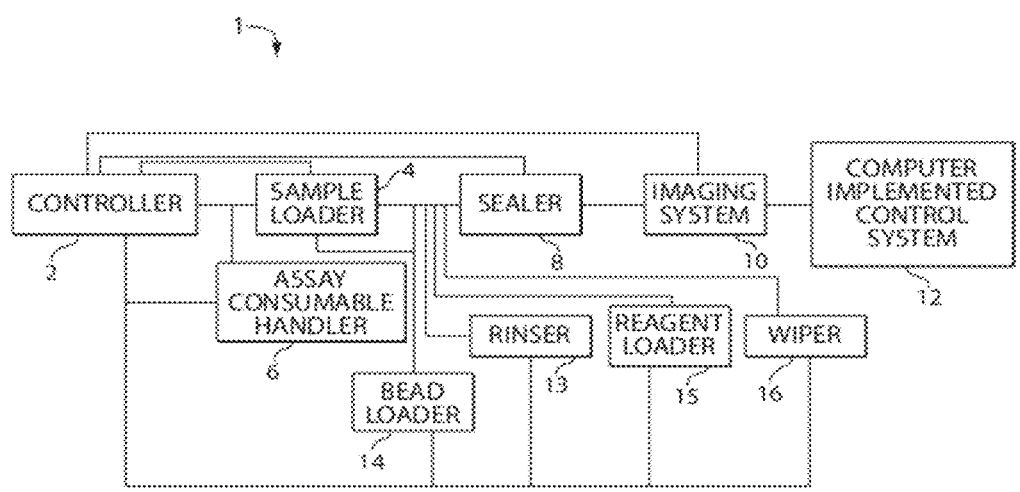
FIG. 1 is a block diagram showing the components of an embodiment of an automated assay system comprising at least a sample loader, a sealer, and an imaging system.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Described herein are systems, apparatus, and methods for performing fluid and sample manipulation. In certain embodiments, the systems, apparatus, and methods are configured for use in assays relating to the detection and/or the quantification of analyte molecules or particles in a sample fluid. In some cases, the systems, methods, and apparatus are automated. The subject matter of the present invention involves, in some cases, interrelated products, alternative solutions to a particular problem, and/or a plurality of different uses of one or more systems and/or articles.

The systems, apparatus, and methods may include at least a portion thereof configured to be used to analyze a sample fluid comprising a plurality of analyte molecules and particles. The systems, apparatus and methods, in some embodiments, are directed towards determining the concentration of analyte molecules or particles in the sample fluid. Various aspect or portions of the apparatus and systems may include one or more of at least one controller, a sample loader, a sealer, an imaging system and/or a computer control system associated with the imaging system. In addition, the apparatus and systems may additionally comprise an assay consumable handler, a reagent loader, a rinser, a wiper, a bead loader, and/or other components, examples of which are described herein. In some embodiments, automated apparatus and systems may allow for fast and/or precise input of samples and/or may reduce errors or variations due to human error and/or manipulation of an assay sample, as compared to non-automated systems.

In some embodiments, an assay method performed by an apparatus or system described herein may comprise at least the following steps. First a sample fluid is provided comprising a plurality of analyte molecules or particles (i.e. molecules and/or particles whose quantity and/or presence is desired to be determined). The sample fluid is exposed to a plurality of beads, wherein at least a portion of the analyte molecules (or particles) in the sample fluid associate with a bead. In some cases, the ratio of beads to analyte molecules is such that statistically, zero or one analyte molecules associate with a bead, as described herein. In some cases, the ratio of beads to analyte molecules is such that statistically, multiple analyte molecules associate with a bead, as described herein. The beads are then loaded into an assay consumable (e.g., associated with an assay consumable handler). The assay consumable comprises a surface having a plurality of assay sites. In some cases, the beads are magnetic or can be induced to be magnetic (e.g., paramagnetic). In some cases, zero or one beads may be contained at/in individual assay sites. In certain cases, essentially all of the assay sites will contain a bead(s), whereas in other cases, only a portion of the assay sites will be loaded with beads. In some embodiments where beads are not used and instead the analyte molecules and/or particles are loaded directed into/onto assay sites, zero or one analyte molecules may be located at/in any each assay site. The assay sites may be exposed to one or more reagent fluids (e.g., to provide a precursor detection agent which is converted to a detection agent upon exposure to an analyte molecule and allows for detection of an analyte molecule, as further described below). In some cases, the assay sites are sealed (e.g., using a sealing component and a sealer apparatus) such that the contents of each assay site are fluidically isolated from each other assay site. At least a portion of the assay sites may be interrogated or analyzed (e.g., using an imaging system) to determine the number of assay sites (or beads) containing at least one analyte molecule or particle. The imaging system, and in certain embodiments other components of the system as well, may be associated with a computer control system that is capable of acquiring and/or analyzing the images obtained by the imaging system. A measure of the concentration of analyte molecules may be determined based at least in part on the images obtained.

A non-limiting example of a system for performing an assay is shown in outline in FIG. 1. In FIG. 1, system 1 comprises at least one controller 2 configured to control and operate assay consumable handler 6, sample loader 4, sealer 8, and/or imaging system 10. Assay consumable handler 6 is configured to be operatively coupled to an assay consumable (not shown; e.g., comprising a plurality of assay sites). Sample loader 4 is configured to load an assay sample (e.g., comprising a plurality of analyte molecule and/or particles) into assay sites of an assay consumable (e.g., associated with assay consumable handler 6). Sealer 8 is constructed and positioned to apply a sealing component to the surface of the assay consumable comprising a plurality of assay sites. Imaging system 10 is configured to acquire at least one image of at least a portion of the assay sites of the assay consumable. Computer implemented control system 12 is associated with at least imaging system 10 and is configured to automatically operate the imaging system and receive information from the imaging system. Apparatus 1 may optionally comprise additional components including, but not limited to, bead loader 14 separate from or associated with sample loader 4, rinser 13 configured to rinse the surface of the assay consumable comprising a plurality of assay sites, reagent loader 15 configured to load a reagent into assay sites of the assay consumable, and, wiper 16 configured to remove excess beads from the surface of an assay substrate. Each of the assay consumable handler, the sample loader, the sealer, the bead loader, the rinser, the reagent loader, and/or the imaging system may be associated with the same or different controllers (e.g., controller 2) configured to operate the component as described herein. The controller may be configured such that the various stages of the assay methods are performed automatically. In certain embodiments, one or more of the components or their functions shown as being separate in FIG. 1 may be integrated into a single component. For example, in certain cases, two or more of the functions of rinser 13, reagent loader 15 and wiper 16 may be combined in a single component of the system. As another example, in certain embodiments, a single computer implemented control system (e.g., computer implemented control system 12) may perform both operation of the imaging system as well as perform the functions of controller 2 as described above. Therefore, reference herein to any one of the components does not preclude such component from performing other functions of the system unless specifically so indicated. Similarly, reference to a system comprising a series of separately recited components does not require the components to be physically distinct structural elements unless specifically so illustrated or described as such (e.g., multiple components may share the same structural elements or have structural elements in common but be configured to function as multiple components of the overall system).

In certain embodiments, system 1 comprises only a single assay consumable handler. It should be noted that more than one spatially separated chamber may be present on an assay consumable, wherein each spatially separated chamber comprises a plurality of assay sites and each spatially separated chamber may be used to analyze a single assay sample, as described below (e.g., see FIGS. 2B and 2C).

The components of system 1 may be positioned in any suitable manner and order, and there may be multiple copies of some components of the apparatus. For example, a rinser may be present in sequence following a sample loader (e.g., such that the assay consumable may be rinsed following application of a sample fluid to an assay consumable) and another rinser may be positioned to operate on the assay consumable following a reagent loader (e.g., such that the assay consumable may be rinsed following application of a reagent fluid to an assay consumable). In some cases, the same device used as a sample loader may also be and function as a rinser, reagent loader, etc.

Figure 3A:
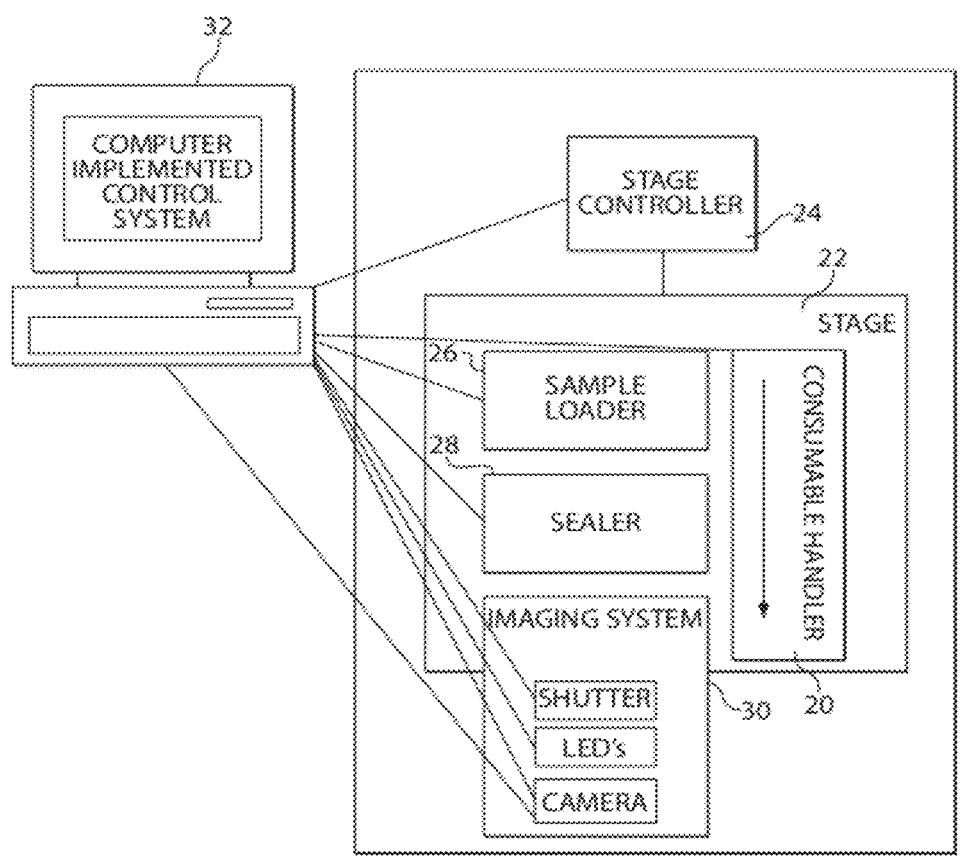
FIG. 3A is a block diagram showing the components of another embodiment of an automated assay system comprising at least a sample loader, a sealer, and an imaging system.

In some embodiments, system 1 may be configured such that the assay consumable may be moved relative to certain system components (e.g., the sample loader, the sealer, the imaging system). As a first example, the assay consumable handler may be associated with an assay consumable handler comprising or part of a stage, wherein the stage and/or the assay consumable handler is configured to move the assay consumable relative to other system components. For example, as shown in FIG. 3A, consumable handler 20 is associated with stage 22. Stage 22 is associated with and configured to be controlled by stage controller 24 such that stage 22 (and thus consumable handler 20) is movable with respect to sample loader 26, sealer 28, and imaging system 30. That is, sample loader 26, sealer 28, and imaging system 30 are located in a fixed position and consumable handler 20 is moved to/from each of the sample loader 26, sealer 28, and imaging system 30. In this embodiment, each of the sample loader 26, sealer 28, and imaging system 30 is associated with a controller and/or computer implements control system 32.

Figure 3B:
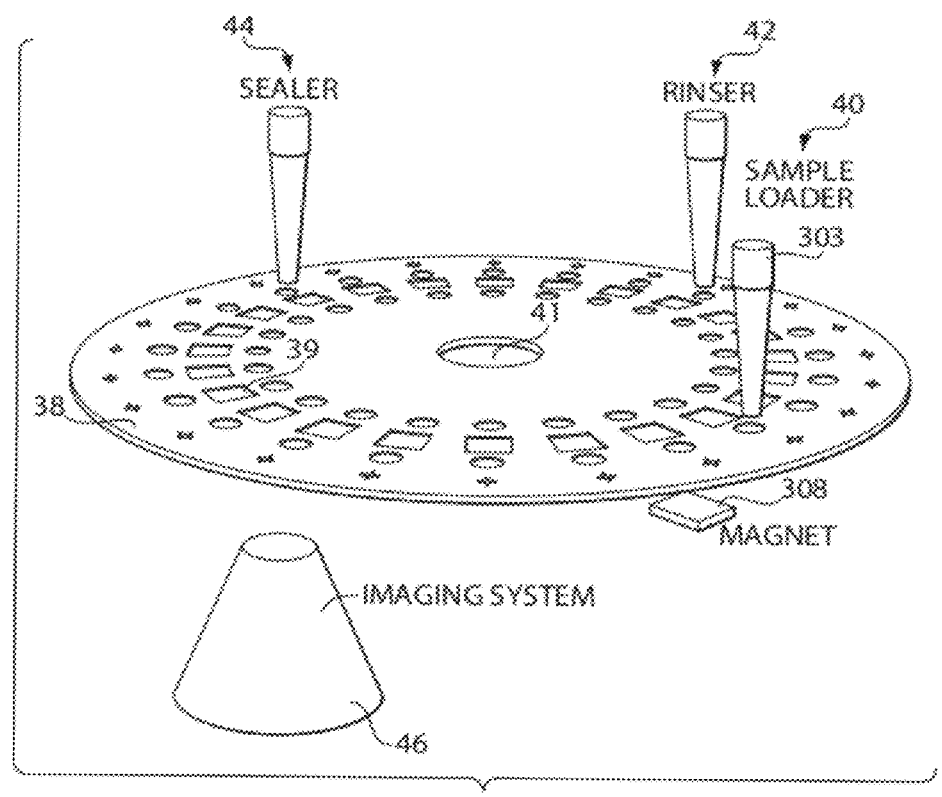
FIG. 3B is a schematic diagram showing an embodiment of an automated assay system using a disk-shaped assay consumable.

As a second example, as shown in FIG. 3B, assay consumable 38 is in the form of a disk comprising a plurality of spatially separated chambers 39, wherein each of the spatially separated chambers contains a surface comprising a plurality of assay sites. Assay consumable 38 may be associated with an assay consumable handler (e.g., a turntable—not shown) configured to rotate assay consumable 38 about the center 41 of the assay consumable. Situated about the disc are sample loader 40, rinser 42, sealer 44, and imaging system 46. Each of sample loader 40, sealer 44, and imaging system 46 may be associated with and/or configured to be operated by a controller and/or a computer implemented control system (not shown). It should be noted that the system may comprise additional components (e.g., a reagent loader, a second rinser, a bead loader, etc.).

Figure 3C:
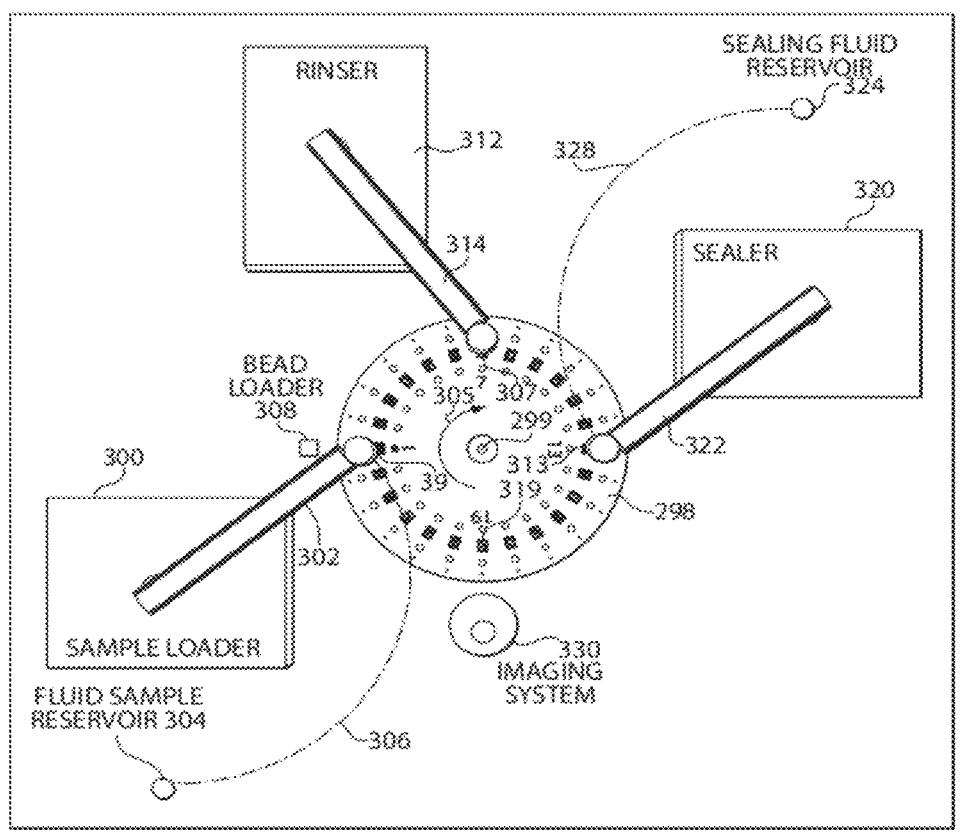
FIG. 3C is a schematic diagram showing another embodiment of an automated assay system using a disk-shaped assay consumable.

FIGS. 3C-3F show a more detailed view of an exemplary system similar to that described in FIG. 3B, showing the system at varying stages of operation. In FIG. 3C, sample loader 300, rinser 312, sealer 320, and imaging system 330 are shown. Each of the sample loader and the sealer comprise an arm which is capable of moving between a first position and a second position, wherein the first position comprises a fluid reservoir (e.g., a sample fluid reservoir, a sealing fluid reservoir) wherein a fluid which is to be applied to the assay consumable is provided. Position two is the location over or in engaging proximity to the spatially separated chambers 39 on the assay consumable. The assay consumable 298 is configured to be rotated about center 299 (e.g., through association of the assay consumable with an assay consumable handler (not shown)), as indicated by arrow 305. It should be understood that any of the components of this system (e.g., sample loader, rinser, sealer, etc.), may be associated with a controller (not shown) configured to control operation of the component. The controller(s) of the components may be configured such that the apparatus operates automatically.

Figure 3D:
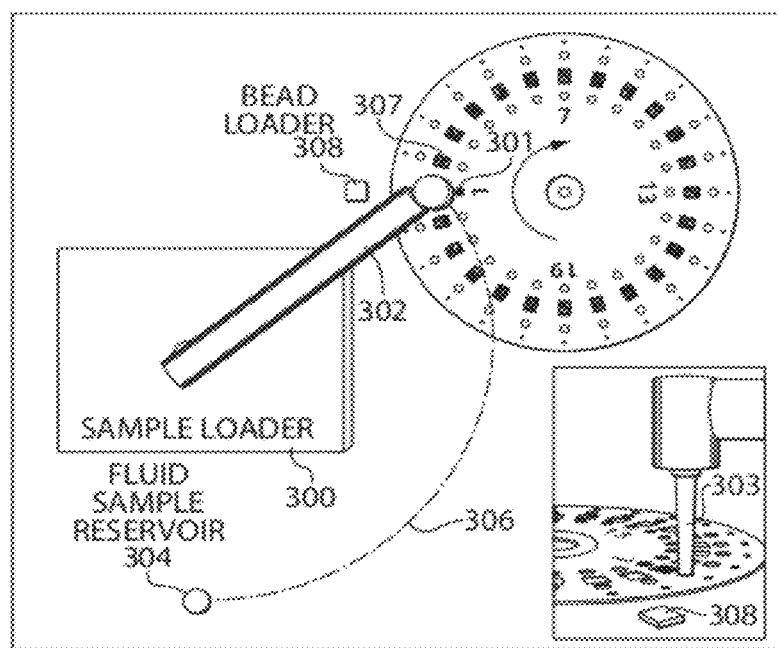
FIG. 3D is a schematic diagram showing the sample and bead loader components of the embodiment illustrated in FIG. 3C in greater detail.

In FIG. 3D, a broadened view of the sample loader 300 is shown. In this particular figure, sample loader 300 comprising a sample loader arm 302 (e.g., associated with a disposable pipette tip) is used to aspirate the sample fluid from sample fluid reservoir 304. Sample arm 302 moves about line 306 such that it may collect a fluid from sample fluid reservoir 304 and then dispense the sample fluid onto spatially separated chamber 301 (e.g., comprising a plurality of assay sites) present on the surface of the assay consumable. In embodiments wherein the sample fluid contains magnet beads, the system may further comprise a bead loader 308. For example, FIG. 3D shows a magnetic bead loader 308 positioned below the point of the assay consumable where the sample fluid is provided to the assay consumable (see inset). In embodiments where the sample arm is associated with a disposable pipette tip (e.g., 303, as shown in the inset), the pipette tip may be disposed of after each sample loading. If no disposable tip is used, the portion of the sample arm which had contacted the sample fluid may be rinsed such that no cross contamination of samples occurs (e.g., by providing a rinsing fluid). Following loading of the sample fluid onto/into the assay consumable, the assay consumable disc may rotate at least one position, for example, such that a second spatially separated chamber (e.g., 307) comprising a plurality of assay sites is positioned at the sample loading station.

Figure 3E:
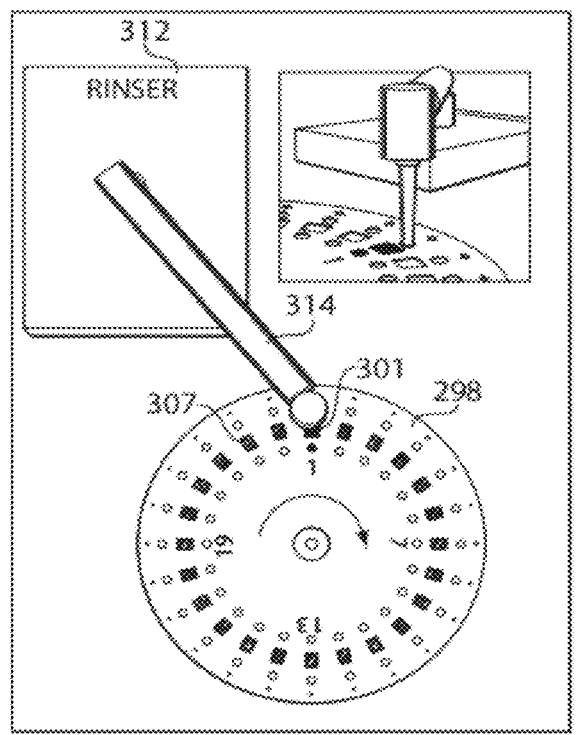
FIG. 3E is a schematic diagram showing the bead wiper components of the embodiment illustrated in FIG. 3C in greater detail.

FIG. 3E shows an expanded view of the rinser 312, which is the next component to which chamber 301 is positioned. In this figure, rinser 312 comprising rinser arm 314 is positioned over spatially separated chamber 301 of the assay consumable. The rinser is capable of providing fluid to spatially separated chamber 301 of the assay consumable 298. In some cases, rinser arm 314 may be directly associated with a fluid pump (not shown) which provides fluid to the rinser arm. In other cases, the rinser arm may function similar to the sample arm described in FIG. 3D (e.g., wherein the system comprises a rinser fluid reservoir (not shown)). Following rinsing of spatially separated chamber 301 of the assay consumable, the assay consumable disc rotates at least one position, for example, such that second spatially separated chamber 307 is positioned at the rinsing station.

Figure 3F:
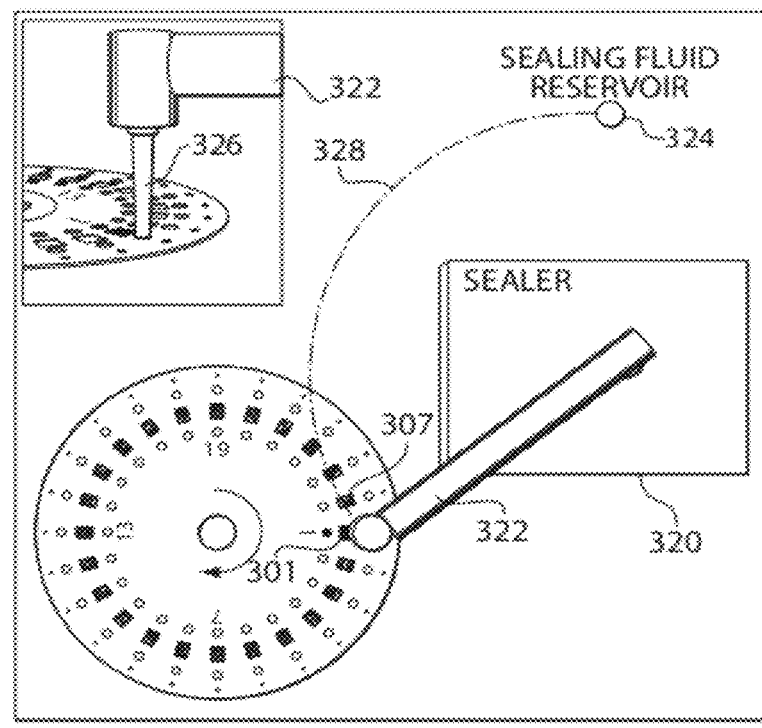
FIG. 3F is a schematic diagram showing the sealer components of the embodiment illustrated in FIG. 3C in greater detail.

FIG. 3F shows an expanded view of the sealer 320, which is the next component to which chamber 301 is positioned. In this exemplary embodiment, the sealer is configured to apply a sealing component comprising a sealing fluid to the assay sites, and the sealer comprises a fluid injector (e.g., pipette 326) configured to apply sealing fluid to the plurality of assay sties in spatially separated chamber 301. The sealer in this apparatus is configured to work in a similar fashion as the sample loader shown in FIG. 3D, wherein sealer arm 322 moves from a first position comprising sealing fluid reservoir 324 along line 328 to spatially separated chamber 301. It should be understood, that other variations of sealers and sealer components (e.g., as described herein) may be substituted for sealer 320 (e.g., a sealer utilizing a roller and a sealing film). In some cases, prior to sealing the assay sited in spatially separated chamber 301, the apparatus may introduce a reagent into the spatially separated chamber via a reagent loader station (not shown). In certain other embodiments, the system may further comprise a second rinser (e.g., to rinse excess reagent from the spatially separated chamber), and/or a wiper (e.g., to remove any beads present on the surface of the assay consumable but not located in reaction vessels on the surface). For example, in some cases, a wiper, a second rinser, and/or a bead loader may be placed between the rinser 312 and sealer 320. Following sealing of spatially separated chamber 301 with sealing fluid, the assay consumable disc rotates at least one position, for example, such that second spatially separated chamber 307 is positioned at the sealer.

Figure 3G:
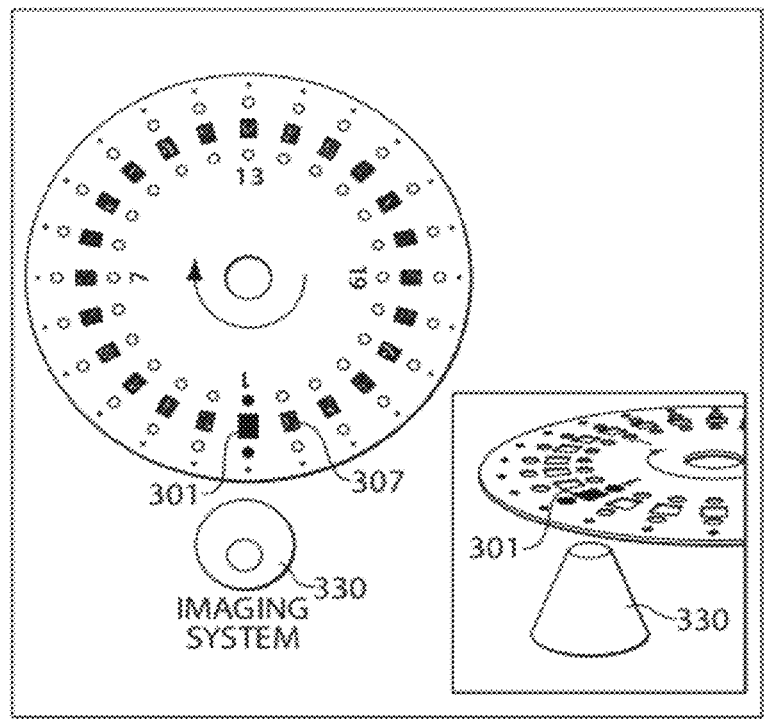
FIG. 3G is a schematic diagram showing the imaging system components of the embodiment illustrated in FIG. 3C in greater detail.

FIG. 3G shows an expanded view of the imaging system. After sealing, the disc is rotated such that spatially separated chamber 301 is aligned with the imaging system such that the assay sites of spatially separated chamber 301 may be imaged. Imaging system 330 may be stationary (e.g., positioned below the disc) or may be movable (e.g., such that it moves into position for imaging). The imaging system may be associated with a computer implemented control system (not shown). Following imaging of spatially separated chamber 301, the assay consumable disc may rotate one position such that second spatially separated chamber 307 is positioned at the imaging system and may be imaged. Similarly, the disc may continue to be rotated until all of the chambers are processed by each of the system component stations. In addition, following imaging of the spatially separated chambers, the assay sites may be rinsed (e.g., using a rinser) and reused or the disc may be disposed of following use of the disc (e.g., a disposable or a recyclable assay consumable disc).

It should be understood, that for the system described in FIGS. 3B-3G, each of the stations (e.g., sample loading station, rinsing station, sealing station, imaging station) may operate simultaneously, or substantially simultaneously, thereby carrying out functions on different spatially separated chambers at about the same time. For example, in FIG. 3C, a sample loader may be applying a sample fluid to spatially separated chamber 301 on assay consumable disc 298, which the rinser is rinsing spatially separated chamber 307 on assay consumable disc 298, while the sealer is applying a sealing fluid to spatially separated chamber 313 on assay consumable disc 298, and/or while the imaging system is obtaining an image of spatially separated chamber 319 on assay consumable disc 298. The timing of the rotation may be adjusted such that good image quality and results are obtained (e.g., adjustment of ideal development time of an assay substrate between sealing and imaging).

Figure 4A:
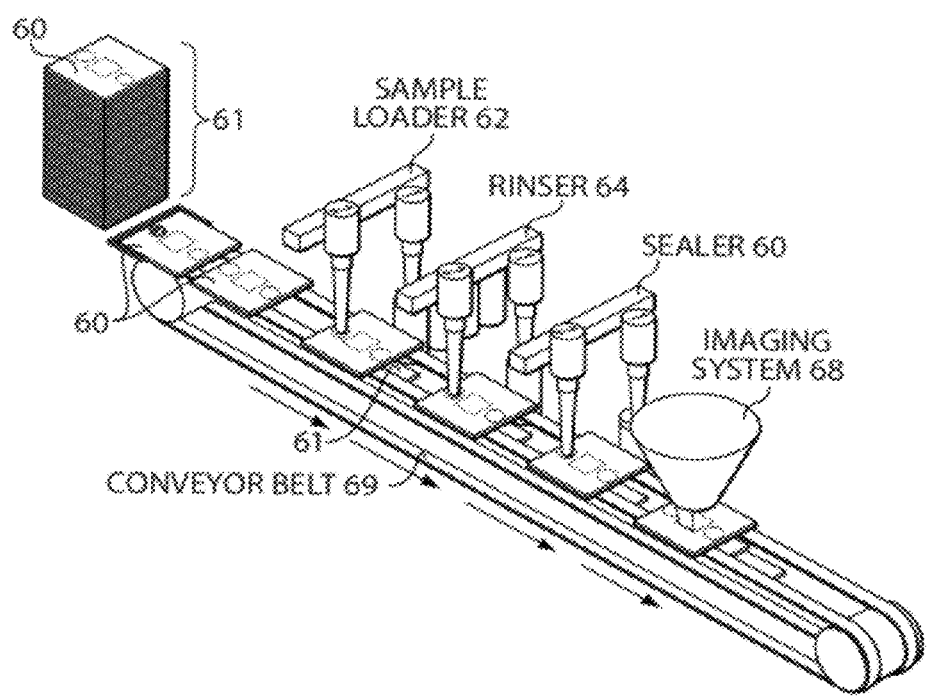
FIGS. 4A-4E are schematic diagrams showing an embodiment of an automated assay system using a linear assay consumable conveyor arrangement (FIG. 4A) and more detailed views of subcomponents thereof (FIGS. 4B-4E)

As yet another example, in some cases, a system may comprise an assay consumable handler that is configured to be operatively coupled to a plurality of assay consumables. For example, as shown in FIG. 4A, numerous assay consumables 60 are shown, each associated with an assay consumable handler comprising a conveyer belt 69. The assay consumable handler may be configured to move each assay consumable on, for example, a conveyer belt type assembly such that each assay consumable is moved sequentially through a plurality of stations. For example, in FIG. 4A, the assay consumable handler comprises conveyer belt 69 configured to move assay consumables 60 from sample loader 62, to rinser 63, to sealer 66, and then to imaging system 68. In some cases, a stack of assay consumables 61 is provided near the conveyor belt. Assay consumables from the stack may be placed on the conveyor belt as needed or as controlled by a mechanism configured to load assay consumables as necessary, for example, see FIGS. 5E and 5F, as described herein. Additional aspects of this system are described herein.

Figure 6A:
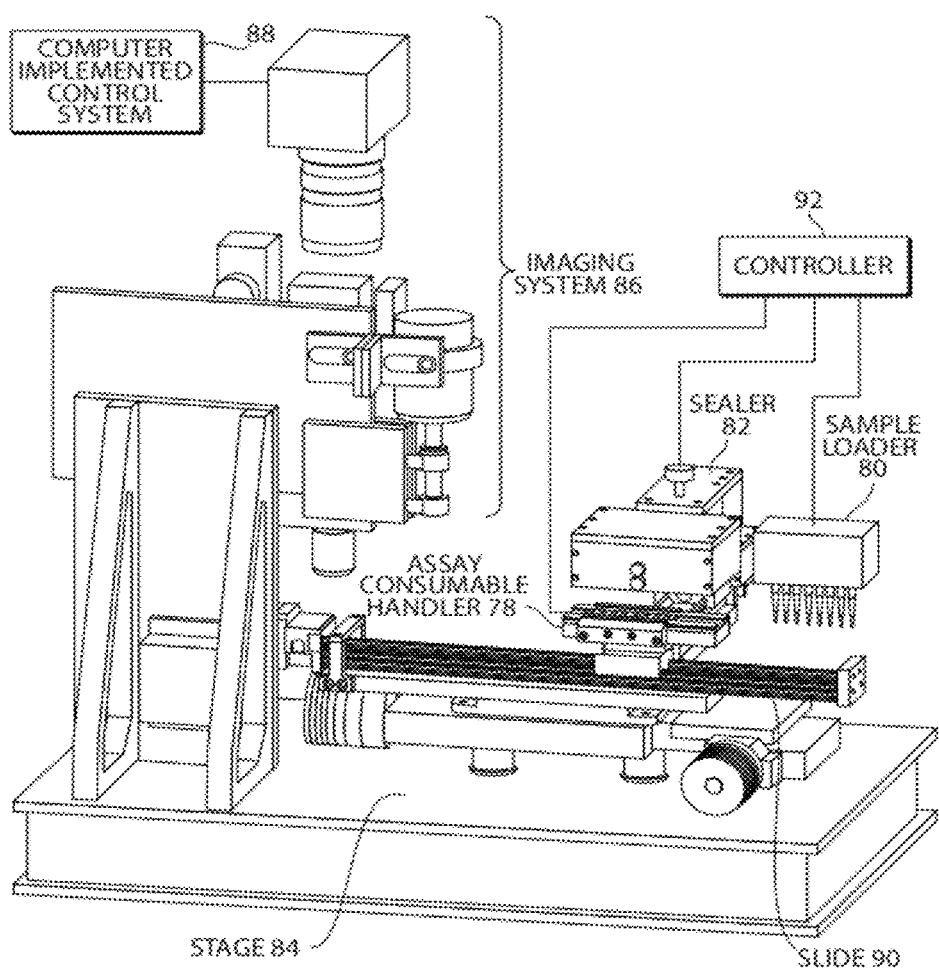
FIG. 6A is a schematic diagram showing an embodiment of an assay system employing a slide for moving an assay consumable.
Figure 6B:
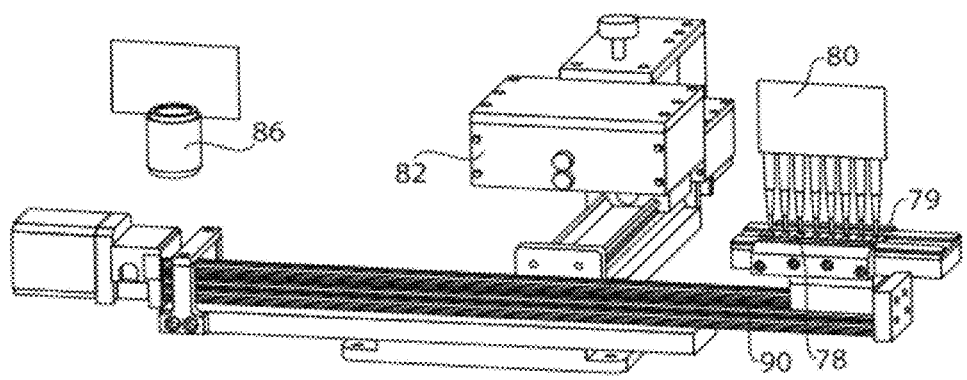
FIG. 6B is a schematic diagram showing portions of the system of FIG. 6A with the assay consumable positioned for sample loading.
Figure 6C:
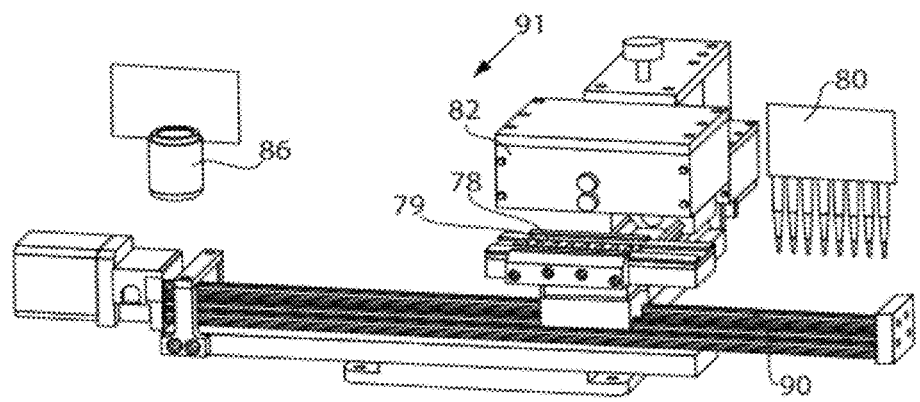
FIG. 6C is a schematic diagram showing portions of the system of FIG. 6A with the assay consumable positioned for sealing.
Figure 6D:
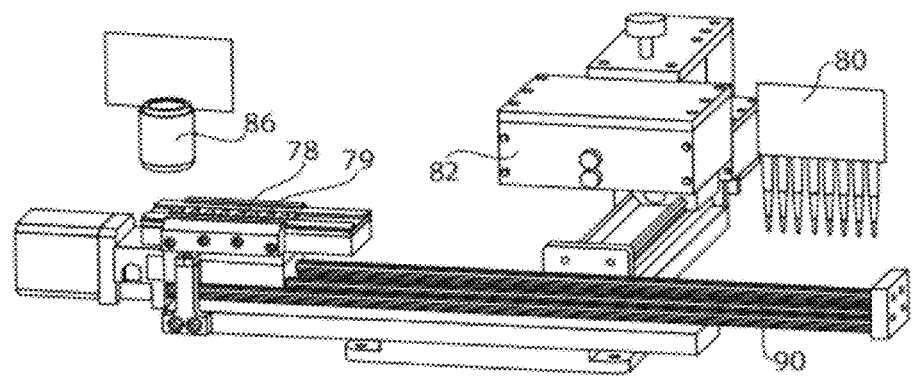
FIG. 6D is a schematic diagram showing portions of the system of FIG. 6A with the assay consumable positioned for imaging.

Yet another example of an apparatus is shown in FIGS. 6A-6D. FIG. 6A shows a system comprising sample loader 80, sealer 82, assay consumable handler 78, imaging system 86, and computer implemented control system 88. The system comprises at least one controller, for example, controller 92 configured to control operation of sample loader 80 and/or sealer 82. The controller may also be configured to control movement of assay consumable handler 78 between the various components (e.g., sample loader, sealer, imaging system, etc.). In this embodiment, the controller is configured to control movement of assay consumable handler 78 on slide 90 between the various components of the system. Imaging system 86 is associated with computer implemented control system 88 (which in some embodiments may the same as or combined with controller 92). Sample loader 80 may be associated with a sample reservoir and/or pumping system (not shown) and supported by and connected to the stage 84 by an appropriate support means (not shown). FIG. 6B shows the system in operation with the assay consumable 79 in a sample loading position. FIG. 6C shows the system in operation with the assay consumable in a seal position. In this system, the sealer comprises a roller, as described in more detail herein, and the sealer moves into position to apply a sealing component in the form of, for example, a resilient membrane or pressure sensitive adhesive, (not shown) to the assay consumable (e.g., along the direction shown by arrow 91). FIG. 6D shows the system in operation with the assay consumable in an imaging position.

Figure 7A:
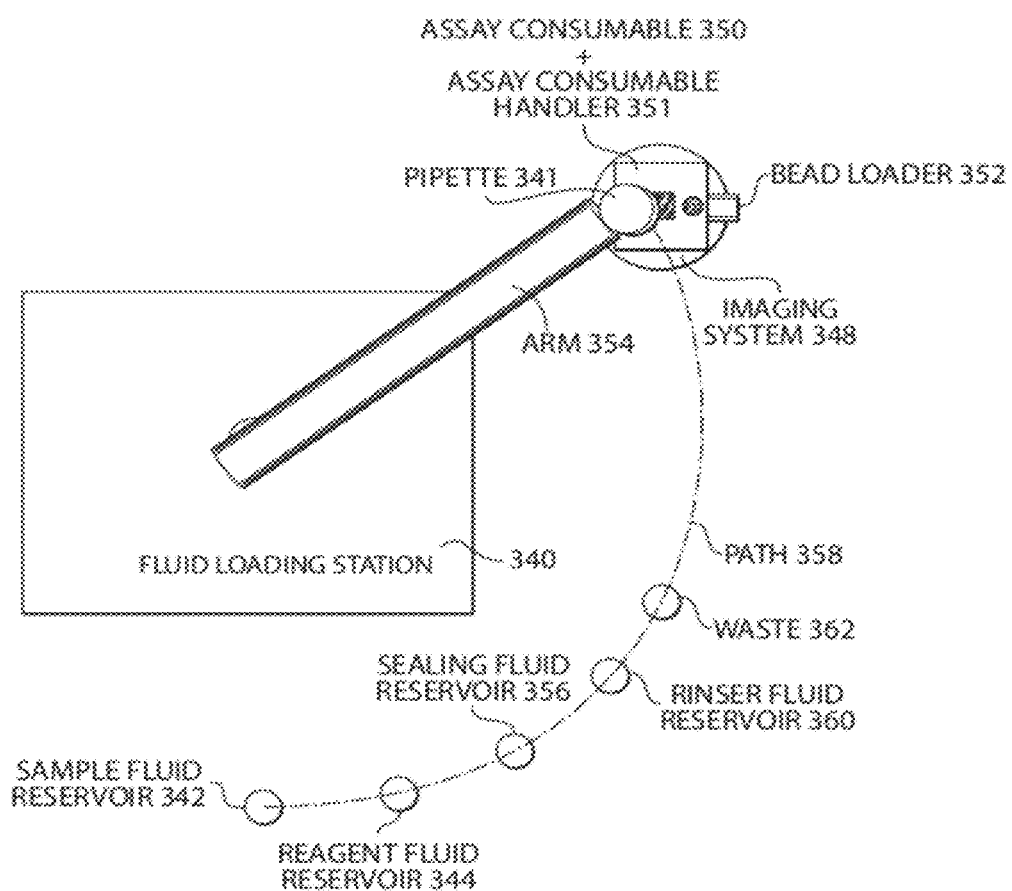
FIGS. 7A-7C are schematic diagrams showing a non-limiting example of a system comprising at least an assay consumable handler, a bead loader, and an imaging system.
Figure 7B:
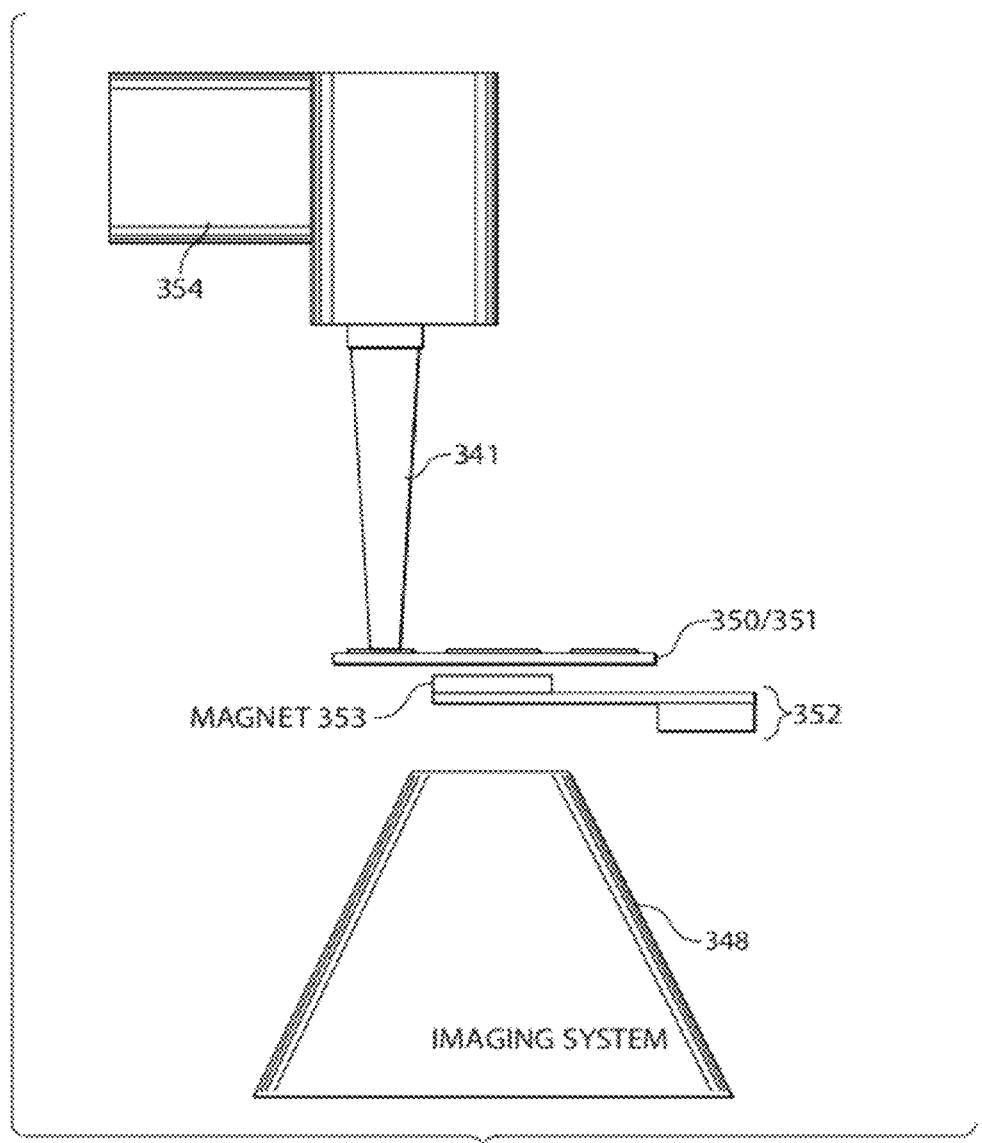
Figure 7C:
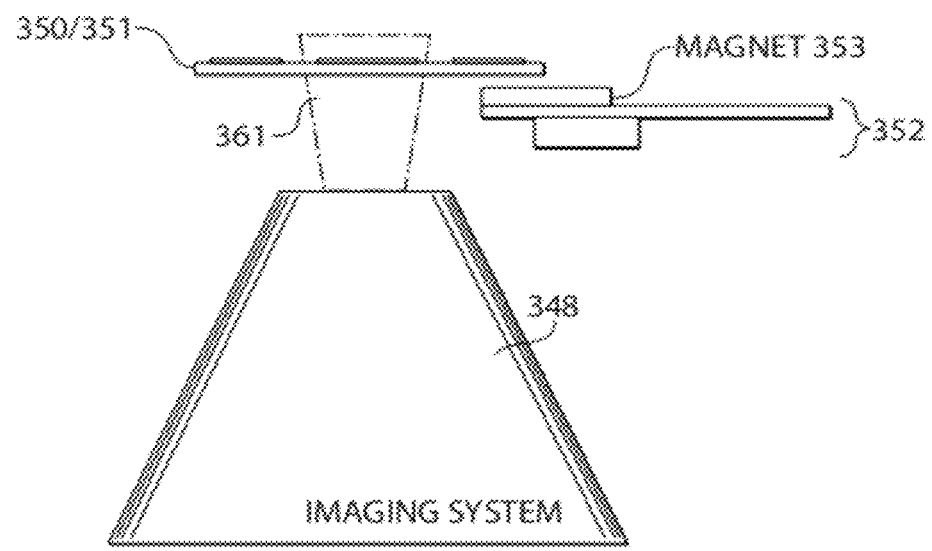

In some embodiments, systems of the invention may be configured such that the assay consumable(s) is held substantially stationary and the components/stations of the apparatus (e.g., the sample loader, the sealer, the imaging system) are moved relative to the assay consumable. For example, a similar apparatus as described in FIGS. 3B-3G is shown in FIGS. 7A-7C. The system in FIG. 7A includes a fluid loading station 340 comprising arm 354 which is capable of and/or configured to move along path 358. Arm 354 is configured to access sample fluid reservoir 342 (e.g., comprising a sample fluid), reagent fluid reservoir 344 (e.g., comprising a reagent fluid), sealing fluid reservoir 346 (e.g., comprising a sealing fluid), and rinsing fluid reservoir 360 (e.g., comprising rinsing fluid). In this example, the system comprises pipette tip 341 (e.g., see FIG. 7B) which is configured to access each of the reservoirs and assay consumable 350. The system may also include a waste reservoir 362, also positioned along path 358, configured to receive excess fluids for disposal (e.g., rinsing fluid used to rinse the pipette between accessing the different reservoirs). The depicted system also includes an assay consumable handler 351 associated with assay consumable 350, imaging system 348 position adjacent to assay consumable 350/assay consumable handler 351, and bead loader 352 comprising a magnet which is movable from a position underneath and adjacent the bottom surface of the assay consumable opposite the upper surface comprising a plurality of reaction vessels (e.g., in a position between the assay consumable and the imaging system) to a second position in which the magnet is not between the assay consumable and the imaging system (e.g., to allow for imaging of the assay sites—as illustrated). The system thus includes components collectively forming a sample loader (i.e., fluid loading station 340, arm 354, sample fluid reservoir 342), a rinser (i.e., fluid loading station 340, arm 354, rinsing fluid reservoir 360), a reagent loader (i.e., fluid loading station 340, arm 354, reagent fluid reservoir 344), a sealer (i.e., fluid loading station 340, arm 354, sealing fluid reservoir 346), a bead loader 352, and an imaging system 348. In this figure, the bead loader (e.g., for use in embodiments wherein the sample fluid includes magnetic beads) comprises a magnet 353 positioned on a movable stage capable of moving from a first position below the assay consumable (e.g., as shown in FIG. 7B) to a second position wherein the magnet is not located below the assay consumable (e.g., as shown in FIG. 7C). In FIG. 7C, due to the retraction of the bead loader 352 comprising magnet 353, the imaging system optical path (e.g., as indicated by area 361) for imaging the assay sites of the assay consumable 350 is unobstructed.

Figure 8A:
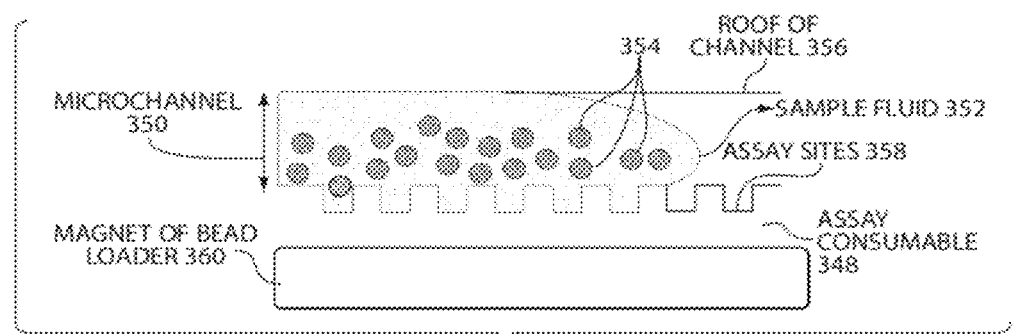
FIGS. 8A-8G is a schematic illustration showing various stages of a method and system for applying a sealing component comprising a fluid.
Figure 8B:
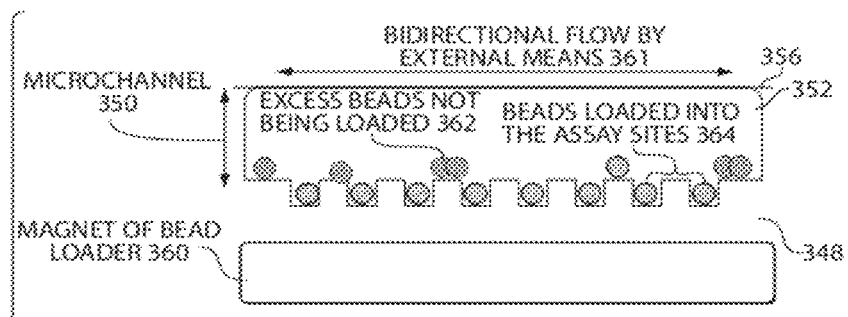
Figure 8C:
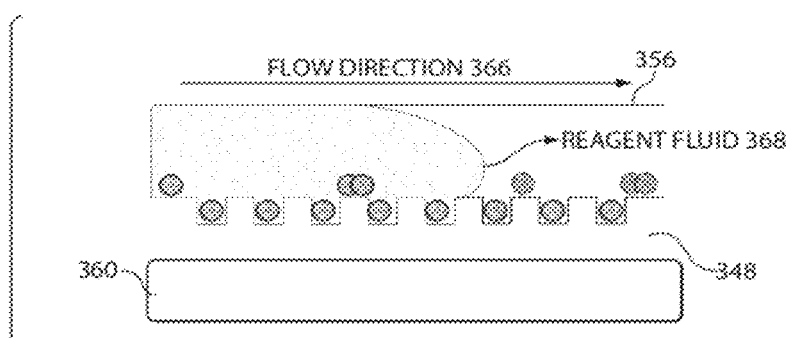
Figure 8D:
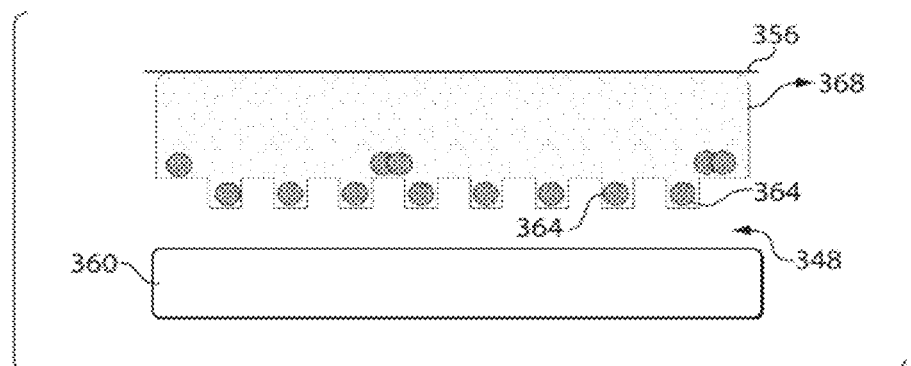
Figure 8E:
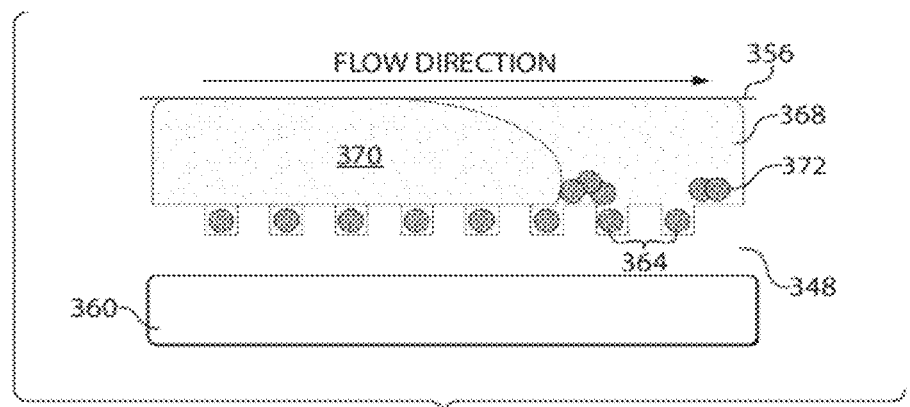
Figure 8F:
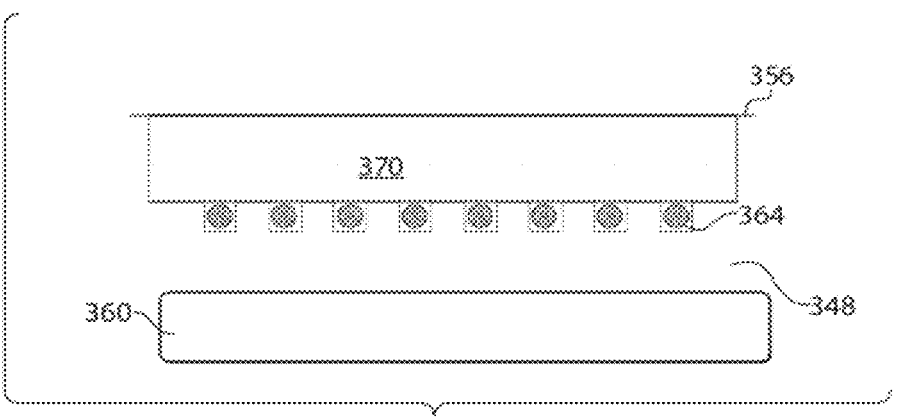
Figure 8G:
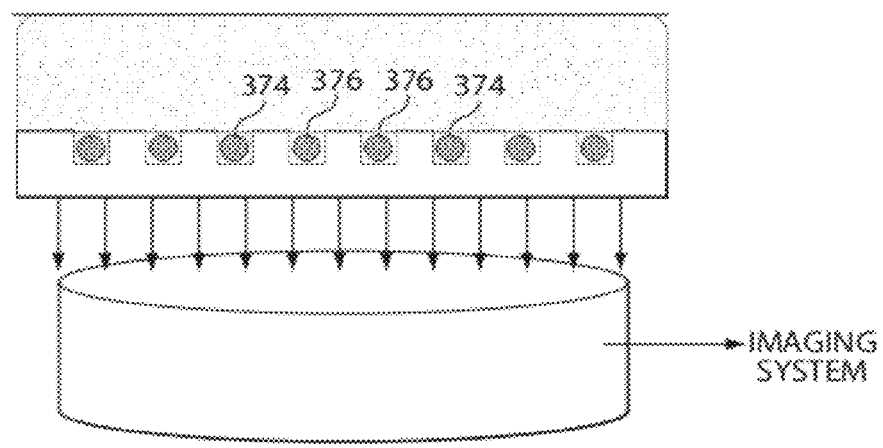

FIGS. 8A-8G depict another embodiment of an arrangement of a system of the invention in which the sealing component is a sealing fluid and the assay sites are contained in a closed channel of the assay consumable. It should be understood, however, that all or at least a portion of the apparatus depicted in FIGS. 8A-8G may be used with an assay consumable wherein the assay sites are not contained in a channel but rather are contained in a surface that is not positioned in a closed channel or is positioned in an open channel. FIG. 8A shows assay consumable 348 comprising a plurality of assay sites 358. The assay consumable may be coupled to or otherwise associated with an assay consumable handler (not shown). Assay sites 358 are contained in microchannel 350. Sample fluid 352 is applied to the assay sites (e.g., through an inlet of the microchannel (not shown)). Sample fluid 352 in this embodiment comprises plurality of beads 354, which in this embodiment, are magnetic. Also provided is bead loader 360 comprising a magnet (or a magnetic field generator), wherein the magnet aids in placing the beads in/on the assay sites (e.g., reaction vessels as illustrated). In FIG. 8B, a bi-directional flow is provided in the channel of sample fluid 352 as indicated by arrow 361. The term "bidirectional flow" is meant to refer to flow such that the direction of the flow in the channel is changing directions (e.g., by apply pulsating negative and positive pressures to the inlet and/or outlet of the channel). The component capable of providing bi-directional flow is a portion of the bead loader, where the bi-directional flow causes relative motion between the beads and the assay consumable handler, and hence, between the beads and the assay sites/assay consumable. After application of the bi-direction flow for a suitable period of time, portion 362 of beads are not substantially contained in an assay site and portion 364 of beads are substantially contained in the assay sites. FIG. 8C shows addition of a reagent fluid 368 to the channel (e.g., using a fluid injector at a channel inlet (not shown)). Flow is provided in a single direction, as shown by arrow 366. FIG. 8D shows the system at a slightly later period of time wherein reagent fluid 368 has substantially replaced sample fluid 348 from FIG. 8B in the channel. FIG. 8E shows a similar set-up as in FIG. 8C, but in this embodiment, reagent fluid 368 is being replaced by sealing fluid 370. FIG. 8F shows the system at a later time at which sealing fluid 370 has substantially replaced reagent fluid 368 in the channel. Generally, sealing fluid 370 should be substantially immiscible with reagent fluid 368 and/or sample fluid 352 at least over the course of the time required to perform the assay. In some cases, sealing fluid 370 may also function as a wiper and aid in removing or substantially removing beads 372 not substantially contained in as assay site, as shown in FIG. 8E. Magnet 360 in FIGS. 8E and 8F may optionally be removed. A least a portion of the sealed assay sites of the assay consumable from FIG. 8F may then be imaged, as shown in FIG. 8G. Assay sites which contain an analyte molecule or particle may provide a different signal (e.g., assay sites 374) as compared to assay sites which do not contain any analyte molecules or particles (e.g., assay sites 376). An example of a system using an apparatus as described in FIGS. 8A-8F is provided in Example 3.

The foregoing exemplary system and system components (e.g., assay consumable, assay consumable handler, sample loader, rinser, sealer, bead loader, imaging system, etc.) may take a variety of different forms and/or formats in different embodiments of the invention, several examples of which are described herein. For example, as mentioned and discussed above, in certain embodiments, a single structural element or associated elements may perform multiple functions and constitute more than one of the above-recited system components. Additional components may be utilized as a substitute for and/or in combination with the exemplary systems described herein within the scope of the invention.

Assay Consumable Handlers

An assay consumable handler is a component which is configured to be operatively coupled to an assay consumable and/or to support and facilitate manipulation and/or positioning of the assay consumable by or in the system. The assay consumable handler may be stationary or may be movable, or at least parts thereof may be movable. For example, the assay consumable handler may be operatively associated with or comprise a stage, wherein the stage is movable. The stage may be associated with a controller configured to automatically move the stage, and/or the assay consumable handler. An assay consumable handler may be sized and/or shaped to mate with the assay consumable in certain embodiments. For example, an assay consumable handler may comprise a depressed area wherein the assay consumable may be situated and secured. Alternatively, the assay consumable handler may comprise a substantially planar surface that the assay consumable is placed upon. In some cases, the assay consumable handler comprises a plurality of fasteners (e.g., snaps, clips, clamps, ring clamps, etc.) which aid in attaching the assay consumable to the assay consumable handler, such that there is little or no movement between the consumable and the consumable handler during at least certain periods of operation of the system. As another example, the assay consumable handler may utilize a vacuum or pneumatic system for securing the assay consumable. In certain embodiments, the assay consumable handler can comprise recognition elements which are complimentary to recognition elements of an assay consumable to facilitate proper positioning and/or to prevent use of improperly configured or counterfeit assay consumables. For example, an assay consumable may comprise a plurality of notches and the assay consumable handler may comprise a plurality of complimentary indentations. As another example, the assay consumable may comprise an RFID chip or bar code reader and the assay consumable may be required to comprise an authorized RFID chip or bar code to permit coupling of the assay consumable and the assay consumable handler without triggering an alarm condition or causing the controller to shut down operation of the system.

Figure 5A:
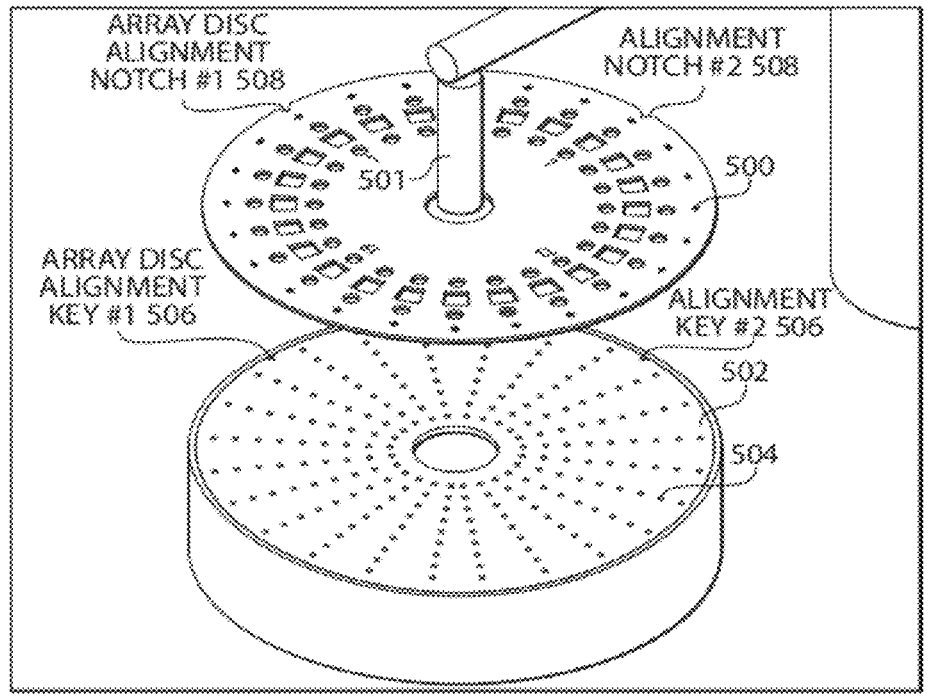
FIGS. 5A-5F are schematic diagrams showing illustrating exemplary assay consumable handlers, according to some embodiments.
Figure 5B:
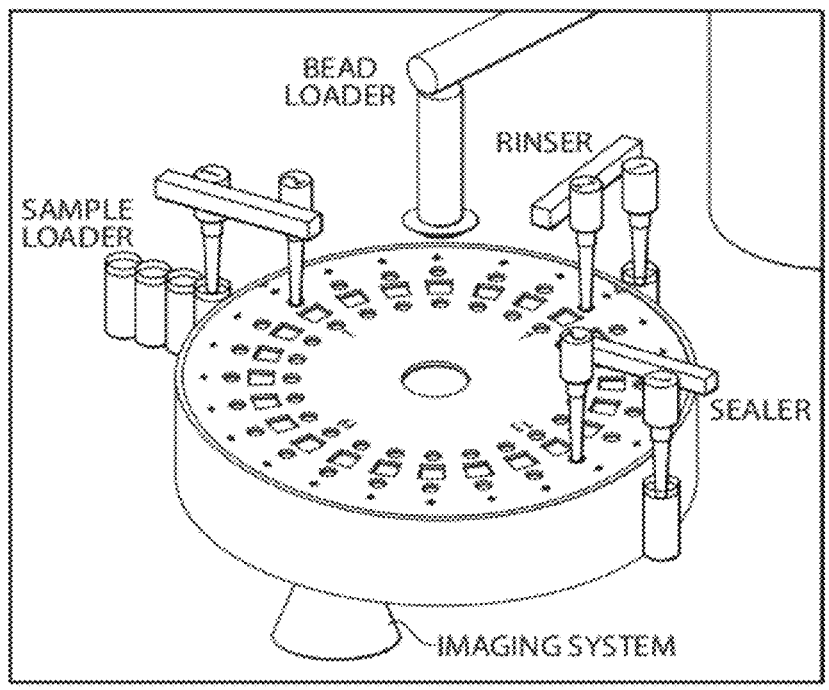
Figure 5C:
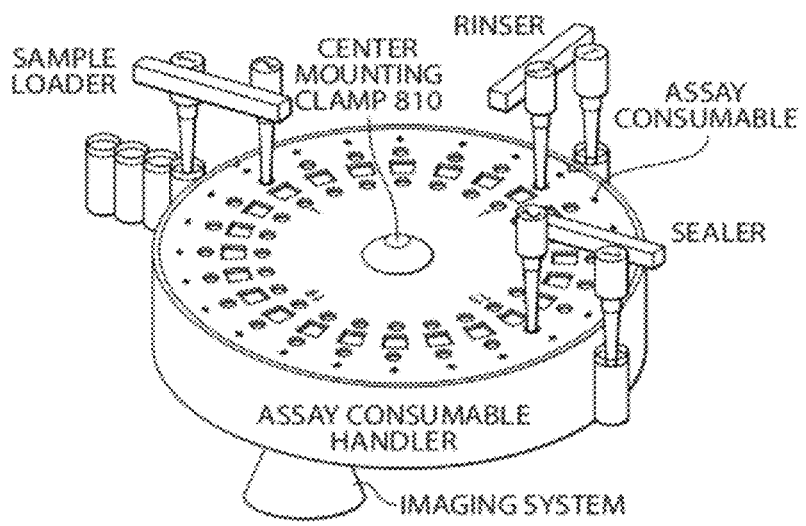
Figure 5D:
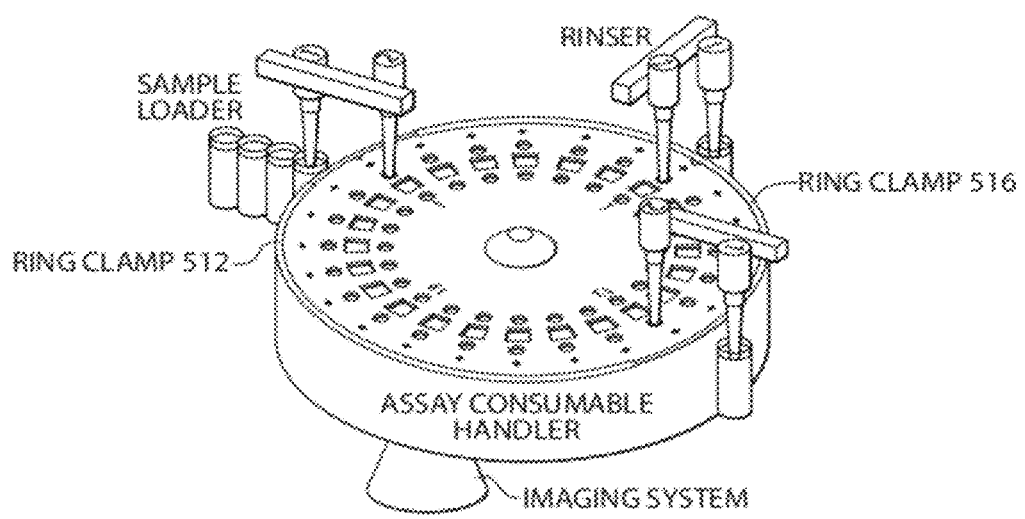

Non-limiting examples of assay consumable handlers are depicted in FIGS. 5A-5F. FIG. 5A shows assay consumable 500 and assay consumable handler 502. The apparatus comprises a component capable of moving assay consumable 500 from a first position not associated with the assay consumable handler to a position associated with assay consumable handler (e.g., arm 501). Assay consumable 500, in this example, comprises at least one notch or recognition element (e.g., notches 508) which interact specifically with a key or recognition element (e.g., keys 506) on assay consumable handler 502. Assay consumable handler 502 also comprises a plurality of holes 504 which through which a vacuum may be applied to the assay consumable. Once the assay consumable is lowered into position (e.g., as shown in FIG. 5B), where notches 508 are aligned with keys 506, vacuum may be applied to holes 504, which causes assay consumable 500 to lie flat in a secured position on the assay consumable handler. Following loading of the assay consumable on to the assay consumable handler, the handler may be positioned such that the various components of the apparatus (e.g., sample loader, bead loader, sealer, wiper, imaging system, etc.), are in the appropriate places. The vacuum may be maintained until the desired number of the individual groups of assay sites have been analyzed. FIG. 5C shows an assay consumable associated with the assay consumable handler via center mounting clamp 510. Center mount clamp 510 secures and holds the assay consumable flat. FIG. 5D shows an assay consumable associated with an assay consumable handler via first ring clamp 512 and second ring clamp 516. The ring clamps are configured and positioned to hold the assay consumable to the assay consumable handler by clamping the outer edges of the assay consumable.

Figure 5E:
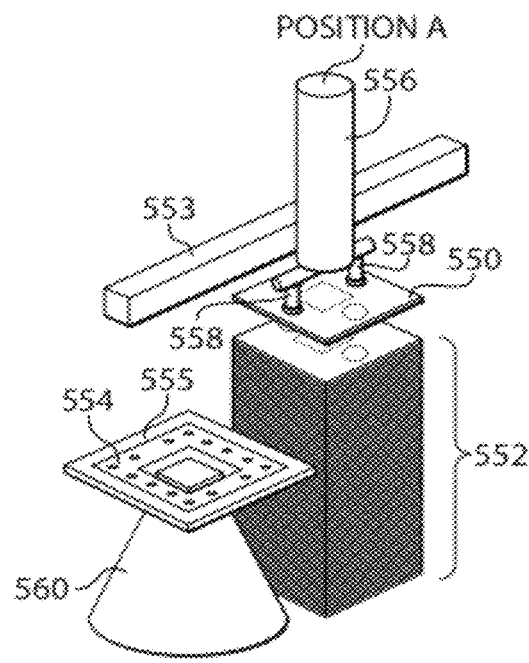
Figure 5F:
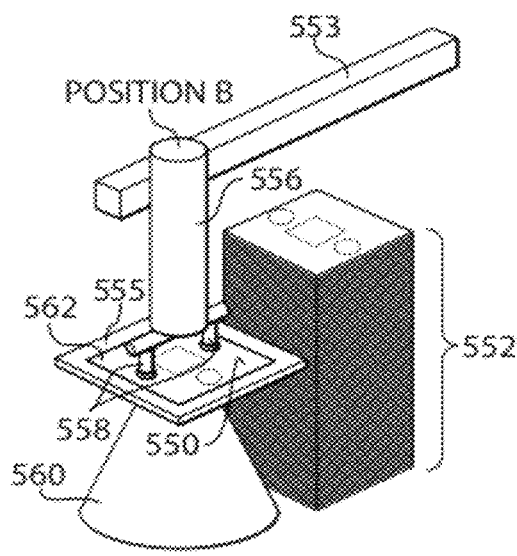

FIGS. 5E and 5F show another example of an assay consumable handler comprising handler grabbing arm 556, cross arm 553 operatively connected with a portion of the apparatus (not shown), assay consumable handler stage 555, and assay consumable attachments 558. Also shown in the figure is imaging system 560. In FIG. 5E, single assay consumable 550 is configured to be moved from stack 552 to assay consumable stage 555. Arm 556 is in position A such that arm 556 is positioned above stack 552. Assay consumable attachments 558 (e.g., suction cups, clips, etc.) are lowered so as to grab assay consumable 550. Handler arm 556 is moved from position A in FIG. 5E to position B in FIG. 5F along cross arm 553 such that assay consumable 550 is positioned above assay consumable stage 555. FIG. 5F shows the assay consumable lowered so as to connect assay consumable 550 to assay consumable stage 555. In this figure, assay consumable stage 555 comprises holes 554 in fluid communication with a source of vacuum, so that a vacuum may be applied to the underside of assay consumable 550 to hold it in position, as described herein (e.g., for similar, also see FIG. 5A (holes 504)).

In some cases, the assay consumable handler may comprise a conveyor belt type assembly (e.g., see FIG. 4A (69)). Additional assay consumable handlers are depicted in the figures described throughout, for example, see FIG. 5A (502), FIG. 5A (502), FIG. 5E (555), FIG. 6B (78), etc.

Exemplary Sample Loaders, Rinsers, and Reagent Loaders

A variety of liquid injection/application systems useful or potential useful for use as a sample loader, rinser and/or reagent loader are known to those skilled in the art. Generally, the sample loader is configured to apply an assay sample to or into an assay consumable to facilitate loading of the assay sample into assay sites of the assay consumable. In some embodiments the assay sample comprises a fluid, and the sample loader comprises a fluid injector. For example, the fluid injector may comprise a pipettor, in certain embodiments an automated pipettor, an inkjet printer, blister pack, microfluidic connectors, etc. The pipetting or liquid injection/application system may also include a means for pressurizing the fluid for injection/application, e.g., a pump and may be connected in fluid communication with a source of fluid to be injected via appropriate tubes, valves, connectors, etc. In some cases, the sample loader is associated with a controller configured to automatically control operation of the sample loader to load the sample to each fluidically isolated area of an assay consumable.

FIG. 6A illustrates a non-limiting example of a sample loader that comprises a plurality of pipettes, wherein each pipette is configured to align with a spatially separated group of assay sites on an assay consumable. In this example, multiple pipettes are present as the assay consumable comprises a plurality of spatially separated groups of assay sites, which can be fluidically isolated, e.g., by a seal component. Each pipette may be used to apply the same or a different assay sample in certain embodiments.

Figure 4B:
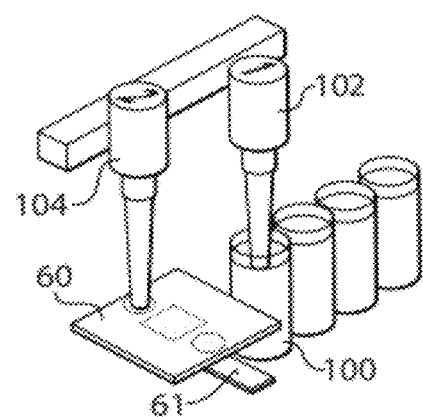

In some embodiments, however, the sample loader may comprise only a single injection point (e.g., a single pipette) to load only a single area of an assay consumable. For example, as shown in FIG. 3B, the sample loader comprises a single pipette. As another example, FIG. 4B shows a single pipette being used as the sample loader, wherein the sample pipette is capable of being moved from an intake position 102 (e.g., positioned over sample vial 100, wherein sample intake occurs) to an output position 104 (e.g., position over assay consumable 60), wherein the sample may be applied to the assay consumable.

In some cases, a system of the invention may additionally include a rinser and/or a reagent loader, which may be separate from the sample loader in certain cases. A rinser may be a liquid injection system configured and positioned to rinse at least a portion of the assay consumable, typically after the sample has been loaded. For example, in some cases, the rinser provides a fluid to the surface of the assay consumable comprising a plurality of reaction vessels, thereby diluting and/or removing any other fluids present (e.g., fluids comprising analyte molecules, fluids comprising a reagent, etc.). In some cases, the fluid may also act as a wiper to cause at least a portion of beads present to be removed.

Figure 4C:
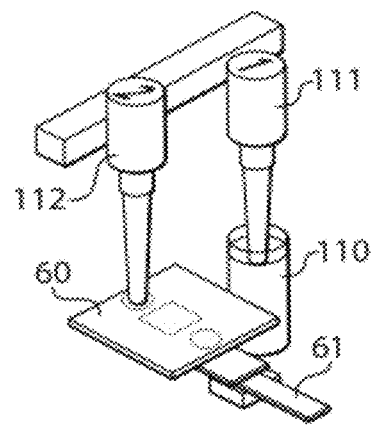
Figure 4D:
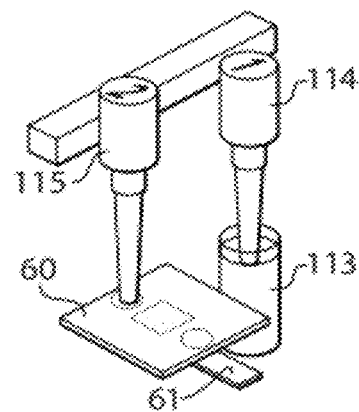

Similar to a sample loader, a reagent loader may be configured to load a reagent that is not the sample into assay sites of an assay consumable. The rinser and/or the reagent loader may be associated with a controller configured to automatically operate the rinser/reagent loader. Rinsers and/or reagent loaders may utilize similar set-ups and components as described for sample loaders. A non-limiting example of a rinser is shown in FIG. 4C. FIG. 4C shows a single pipette, which would be interconnected with a pump, aspiration system, etc (not shown) as appropriate, being used as the rinser (e.g., injecting a rinsing fluid). As illustrated, the pipette 64 is capable of being moved from an intake position 111 (e.g., positioned over rinse fluid reservoir 110, wherein rinse fluid intake occurs) to an output position 112 (e.g., positioned over assay consumable 60), in which the rinsing fluid may be applied to the assay consumable. Another example of a rinser 312 is illustrated in FIG. 3E.

The rinsers and the reagent loaders are positioned and/or operated in an appropriate sequence with respect to other components of the system to affect the steps of a desired assay to be performed with the system. For example, an assay system of the invention may be configured such that an assay consumable is exposed to the following components in the following order (optionally with other operations intervening between one or more of the enumerated steps): 1) sample loader (e.g., to load a sample into the assay sites), 2) rinser (e.g., to remove any excess sample fluid from the surface of the assay consumable), 3) reagent loader (e.g., to load a reagent into the assay sites), 4) sealer, etc. Other variations will depend on the particular assay/use for which the system is employed, as would be understood by those skilled in the art.

Exemplary Bead Loaders and Bead Applicators

In some embodiments, an apparatus of the present invention may comprise a bead loader to facilitate loading of assay beads into reaction vessels in an assay consumable. A bead loader is a component which is configured to facilitate insertion of beads into individual assay sites. In some cases, the bead loader may be configured such that substantially all individual assay sites contain zero or one beads after loading (e.g., as described in more detail below). In other cases, however, the bead loader may be configured such that a substantial fraction of assay sites assay site contain more than one bead. As with other components, the bead loader may be associated with a controller configured to automatically operate the bead loader.

In some cases, the bead loader may function, at least in part, by causing relative motion between the beads and the assay consumable handler, and thus, in some embodiments, between the beads and a surface of an assay consumable (e.g., the surface comprising a plurality of assay sites) associated with the assay consumable handler. In some cases, the assay consumable handler may be configured to move (e.g., in circular motions, side-to-side motion), thereby causing relative motion between the assay consumable and a liquid containing the beads or just the beads themselves. In some cases, the beads may be contained in a liquid on the surface of the assay consumable, and the fluid in which the beads are contained may be moved (e.g., using a fluid pump, and pipette, doctor blade, etc.) such that the beads contained in the fluid are moved relative to a stationary assay consumable. In certain cases, both the assay consumable and the beads/bead containing liquid are moved to create the relative motion.

In some embodiments, as described herein, the beads are magnetic. In such embodiments, the bead loader may comprise at least one magnet or other magnetic field generator. The magnetic field generator may be positioned such that appropriate magnetic field gradients are present to draw the beads towards/into the assay sites. In some cases, the bead loader comprises at least one magnetic field generator located or positionable adjacent to the surface of the assay consumable handler (e.g., a bottom surface). In a particular embodiment, the magnetic field generator is located opposite the surface of the assay consumable in which a plurality of reaction vessels are formed (i.e. underneath the wells). It should be understood, that in embodiments comprising or describing a permanent magnet, an electromagnet or other magnetic field generator may be substituted for the permanent magnet. Appropriate or potentially useful magnetic field generators are known in the art. Non-limiting examples of magnetic field generators include permanent magnets, arrays of permanent magnets, arrangements of two or more permanent magnets and various combinations of permanent and/or electromagnets.

Figure 9A:
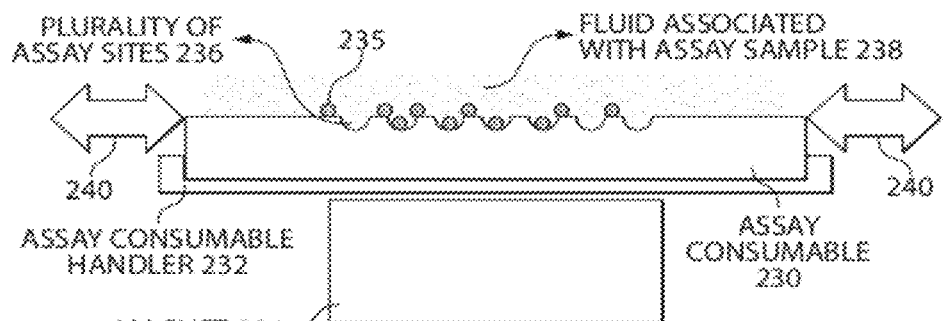
FIGS. 9A-9C are schematic diagrams showing exemplary configurations which may be used to provide relative motion between a magnet and an assay consumable handler and/or an assay consumable.
Figure 9B:
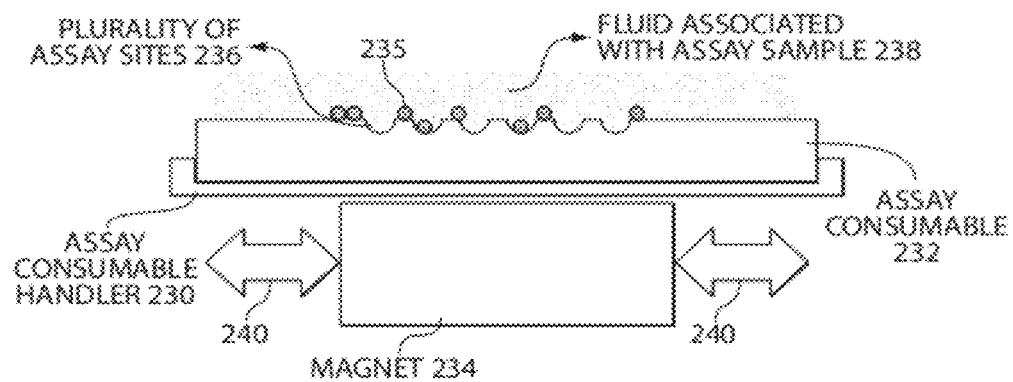
Figure 9C:
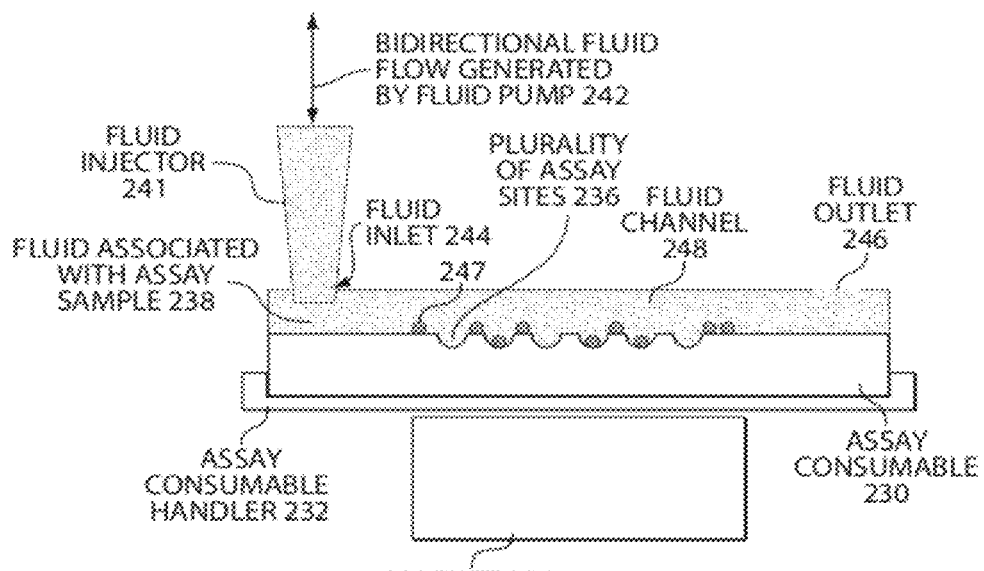

A non-limiting example of a bead loader comprising a magnet (or a magnetic field generator) is shown in FIGS. 9A-9C. In FIG. 9A, assay consumable handler 232 is associated with assay consumable 230 comprising a plurality of assay sites 236. Sample fluid 238 comprising magnetic beads 235 are in contact with surface of assay consumable 230 comprising plurality of assay sites 236 in the form of reaction vessels (i.e. wells). Magnet 234 is positioned adjacent assay consumable handler 232 and adjacent the underside of assay consumable 230. Assay consumable handler 232 is moved (e.g., using a controller (not shown)) as indicated by arrow 240, thereby causing relative motion between assay consumable handler 232 (e.g., associated with assay consumable 230) and magnet 234. Alternatively, in a similar set-up, as shown in FIG. 9B, magnet 234 is moved (e.g., using a controller (not shown)) as indicated by arrow 240, thereby causing relative motion between assay consumable handler 232 (e.g., associated with assay consumable 230) and magnet 234. In another embodiment (not depicted), both magnet 232 and assay consumable handler 232 may be moved simultaneously to cause relative motion between the two components. Another exemplary bead loader in shown in FIG. 3D, as described herein.

Another example of a bead loader comprising a magnet is shown in FIG. 9C, wherein the assay consumable comprises fluid channel 248 having fluid inlet 244 and fluid outlet 246. Sample fluid 238, containing beads 247, is present in fluid channel 248. In this example, magnet 234 is positioned adjacent assay consumable handler 232 and adjacent the bottom surface of assay consumable 230. Fluid inlet 244 is associated with fluid injector 241 which is associated with a fluid pump (not shown). The fluid pump is configured to provide bi-directional (i.e. back and forth) flow (as described herein) as indicated by arrow 242 such that sample fluid 238 is caused to move back in forth in the channel, thus causing beads 247 in the sample fluid to move back and forth, thereby providing relative motion between beads 247 and the assay sites, while magnet 234 tends to pull the beads 247 into the reaction vessels 236.

Figure 4E:
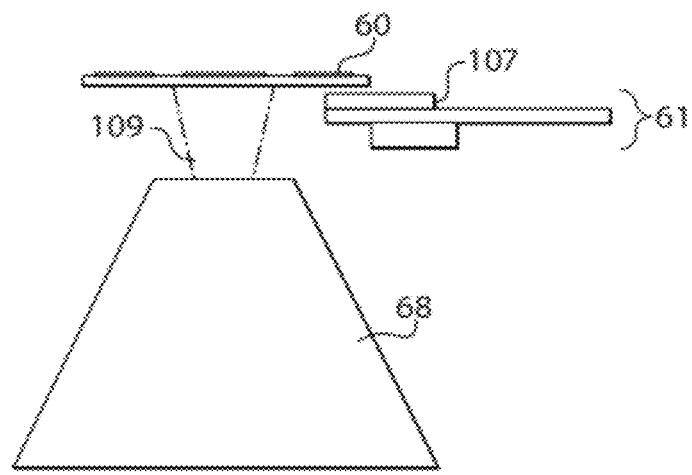

It should be understood, that in some embodiments, an apparatus may comprise more than one bead loader. For example, as shown in FIG. 4A, each assay consumable 60 is associated with a bead loader 61. In some cases, a magnet of the bead loader may form part of the assay consumable handler. As another example, FIG. 4E shows assay consumable 60 positioned over imaging system 68. Assay consumable 60 is associated with bead loader 61. In this figure, the bead loader is has been moved away from the assay consumable to a position such that a clear imaging pathway (shown by area 109) is present between imaging system 68 and assay consumable 60. In this figure, the bead loader comprises magnet 107.

In some cases, a system of the present invention comprises a bead applicator configured to apply a plurality of beads (e.g., magnetic beads) to the surface of an assay consumable or to place a plurality of magnetic beads in close proximity to the surface of an assay consumable. In some embodiments the bead applicator may be associated with controller configured to automatically operate the bead applicator. In some cases, the bead application comprises a liquid injector. Non-limiting examples of liquid injectors have been described herein. In some cases, a bead applicator and a sample loader may be the same device (e.g., wherein the sample fluid comprises beads). However, in some cases, the beads may be providing separately to the assay consumable, such that sample loader and bead applicator are different.

In some cases, for example where the assay consumable comprises a channel in which a surface containing assay sites is contained, the bead application may comprise a fluid pump capable of moving fluid containing the beads into and within/through the channel. For example, as shown in FIG. 9C, the bead applicator comprises fluid injector 241 connected to a fluid pump (not shown) associated with fluid inlet 244 and fluid channel 248 of assay consumable 230. In another example, the bead applicator comprises a pipettor used to deliver beads to an entry port of a microfluidic channel dispense it over the assay consumable. Other non-limiting examples of bead applicators include an automated pipette associated with a fluid pump (e.g., a syringe pump, a piston-action pump, membrane pump, etc.).

Exemplary Wipers

In certain embodiments of the present invention, particularly those employing beads, the system may comprise a wiper which is configured to remove excess beads, and in certain embodiments substantially all of the excess beads, from the surface of the assay consumable that are not substantially contained in an assay site (e.g., well). In some cases it is beneficial to remove excess beads on the surface of the assay consumable that are not substantially contained in assay sites prior to sealing the assay sites as a better seal may result between the surface of the assay consumable and a sealing component. That is, beads on the surface of the assay consumable, in some cases, may prevent and/or reduce the seal quality between the surface of the assay consumable and the sealing component. Therefore, in some cases, inventive assay systems may comprise a wiper positioned and or used in sequence between (and/or between operation of) a bead loader and a sealer to remove any excess beads.

A variety of components or systems known in the art may be suitable or may be modified or adapted to be suitable to function as a wiper. In some cases, the wiper comprises a blade, such as a doctor blade, and is configured to apply the edge of the blade in wiping contact with the surface of the assay consumable comprising a plurality of assay sites. The wiper may be configured to be operated manually (e.g., a squeegee on a graspable handle). In some cases, however, the wiper may be associated with an actuation system and controller which creates and controls movement of the wiper to affect the wiping function. For example, the controller may control movement of a wiper blade so that it contacts the surface of the assay consumable and moves from at or near a first edge of the surface of the assay consumable containing the assay sites to or near a second, opposite edge of the assay consumable, for example, as depicted in FIGS. 10A and 10B.

Figure 10A:
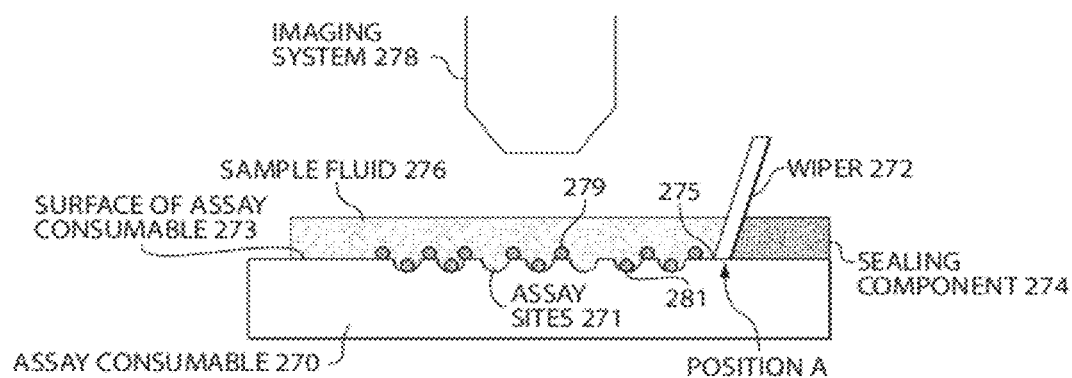
FIGS. 10A-10B are schematic diagrams showing a non-limiting example of a system comprising an imaging system, a wiper, and a sealing component.
Figure 10B:
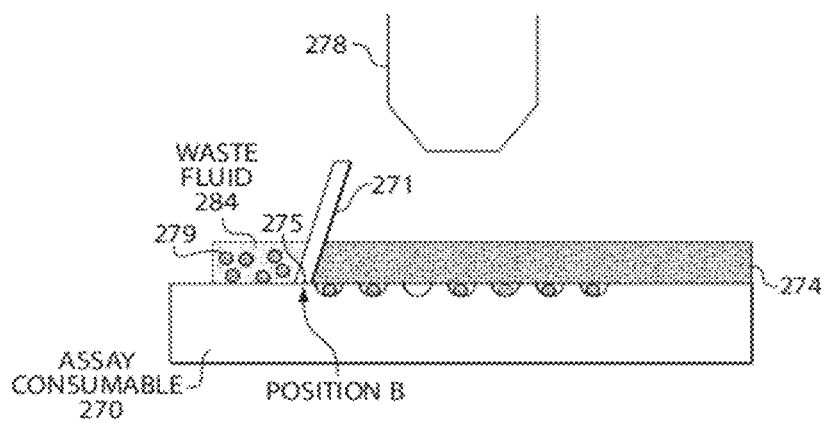

In FIG. 10A, edge 275 of wiper blade 272 is in contact with assay consumable 270 and, and the wiper blade is associated an actuator for moving the blade that is controlled with a controller (not shown). Sample fluid 276 comprising beads 279 and 281 is in contact with the surface of assay consumable 270 comprising plurality of reaction vessels/wells forming assay sites 271. At least some beads 281 are contained in the wells 271 and at least a portion of the beads 279 are not contained in wells 271 and are present on the top surface 273 of assay consumable 270. The controller/actuator is configured to move wiper blade 272 from Position A (FIG. 10A) to Position B shown in FIG. 10B. Substantially all of the beads (e.g., 279) which were not contained in wells 271 and were present on the surface 272 of assay consumable 270 are now present in waste fluid 284. It should be noted, that in FIG. 10A, also shown is a portion of an imaging system 278 associated with a computer implemented control system (not shown).

Figure 11:
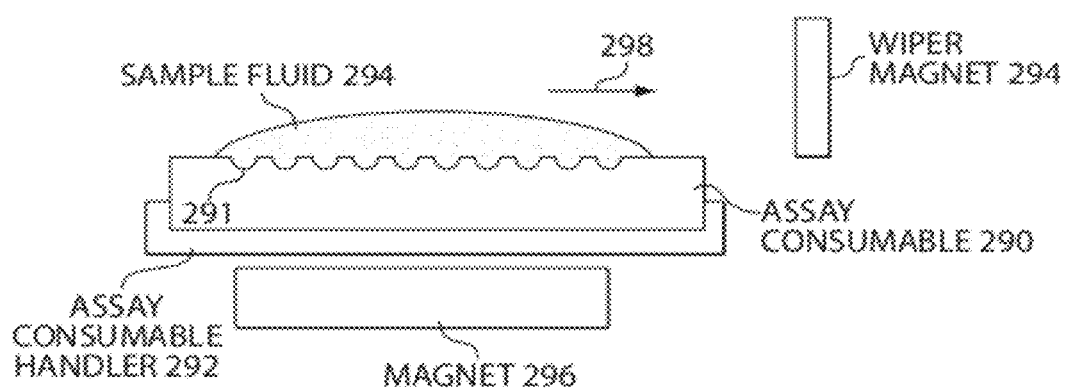
FIG. 11 is a schematic diagram showing a non-limiting example of a wiper comprising at least one magnet.

In embodiments where the beads are magnetic, the wiper may comprise at least one magnet (or at least one magnetic field generator). In a first exemplary embodiment, a wiper comprising a magnet is positioned to generate a magnetic field imposing a force on the magnetic beads having a component that is directed substantially perpendicular to the surface of the assay consumable comprising a plurality of assay sites. For example, FIG. 11 shows an embodiment of a portion of a system including an assay consumable 290 comprising a plurality of reaction vessels 291 positioned and secured by assay consumable handler 292. A bolus of sample fluid 294 comprising a plurality of beads (not shown) is in contact with the surface of assay consumable 290 comprising the plurality of reaction vessels 291. Wiper magnet 294 is positioned to generate a magnetic field imposing a force on the magnetic beads having a component 298 that is directed substantially perpendicular to the surface of assay consumable 290 comprising of reaction vessels 291. The beads in the sample fluid are attracted to the magnetic wiper magnet 294, as tend to move in the direction of the applied magnetic force (arrow 298). In some cases, the system may additionally comprise a bead loader magnet 296 positioned under the assay consumable. Bead loader magnet 296 may aid in keeping any beads which are substantially contained in the reaction vessels from being pulled out of and away from the reaction vessels due to attraction to wiper magnet 294. Those of ordinary skill in the art will be able to determine suitable strengths and positions of magnets 294 and 296 to permit effective loading and wiping functions to occur.

In some cases, the wiper magnet(s) and the assay consumable may be movable relative to each other. In certain cases, the wiper magnet(s) is positionable and movable over the surface of the assay consumable containing reaction vessels. In certain such embodiments, a magnet positioned adjacent to the surface of the assay consumable opposite the surface in which the reaction vessels are formed (i.e. a bead loader magnet), cooperates with the wiper magnet(s) to both load and wipe magnetic beads, in some cases in a single step. In such embodiments, the bead loader magnet is considered part of both the bead loader and wiper components. Furthermore, the wiper may be associated with an actuator controlled by a controller capable of and/or configured to move the magnet positionable and movable over the surface of the assay consumable containing reaction vessels from at or near first edge of the assay consumable to at or near a second, opposite edge of the surface of the assay consumable.

In an exemplary embodiment, the wiper comprises three magnets, wherein a first magnet (also functioning as a bead loader) is located adjacent to the surface of the assay consumable opposite the surface containing reaction vessels, and wherein a second magnet and a third magnet are positionable adjacent the surface comprising the plurality of reaction vessels. In one embodiment, a magnetizable metal separator (e.g., steel) may be positioned between and in contact or in close proximity to the second and the third magnets. In certain embodiments, the metal separator is in the form of a sheet or bar having a thickness that is less than the height or width of the separator that is positioned so that the second and third magnets are separated from each other by a smallest distance substantially equal to the thickness of the separator. In certain embodiments, the second and the third magnets are aligned such that same pole of each magnet is oriented towards the metal separator. Without wishing to be bound by any particular theory of operation, the above wiper configuration may advantageously enable control the magnetic field gradients generated by the arrangement, such that the field gradients increase with distance away from the end/edge of the magnetized metal separator positioned closest to the surface of the assay consumable, such that the wiper arrangement functions acts as a sort of "magnetic squeegee." The magnetic field generated by such an arrangement can induce the beads to move side to side and down into the reaction vessels of an assay consumable.

Figure 12A:
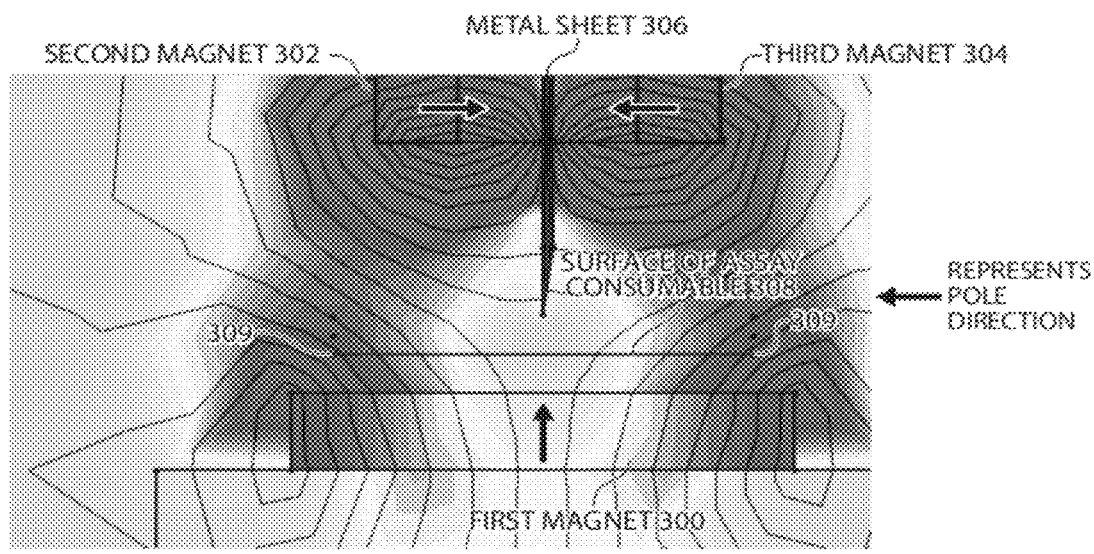
FIGS. 12A-12E are diagrams illustrating the magnetic field and forces applied by a non-limiting example of a wiper comprising more than one magnet.
Figure 12B:
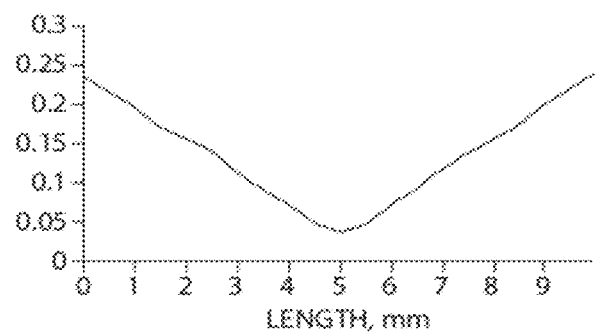
Figure 12C:
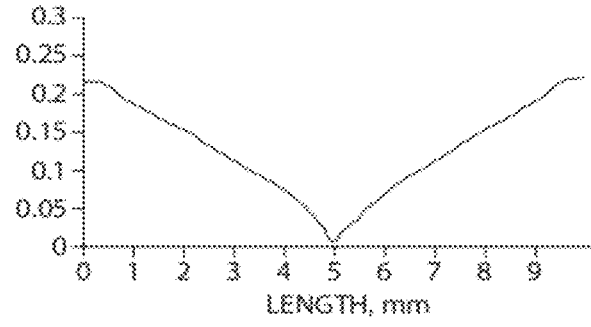
Figure 12D:
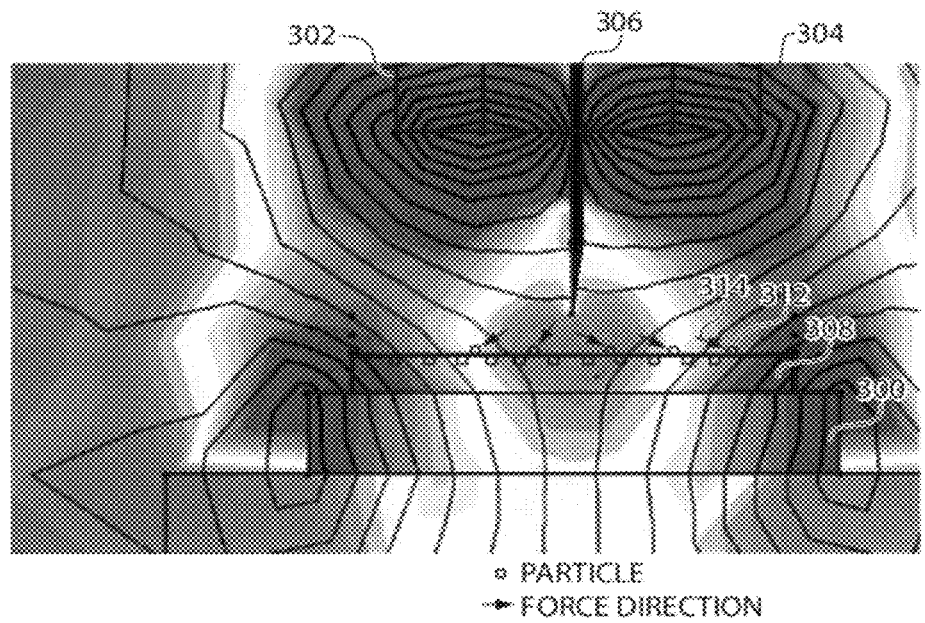
Figure 12E:
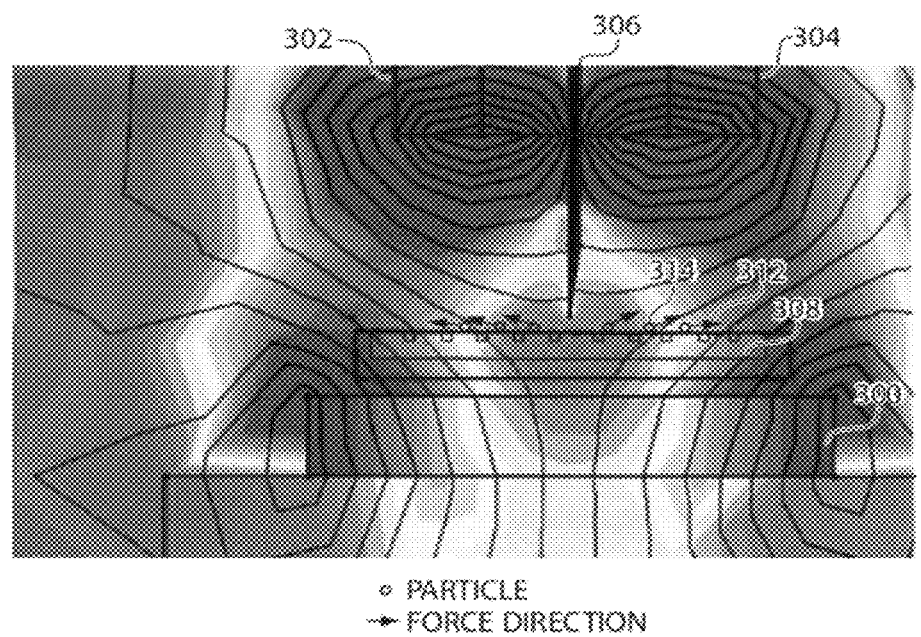

An example of such a "magnetic squeegee" is depicted in FIGS. 12A, 12D and 12E. The wiper depicted in these figures includes a first magnet 300, second magnet 302, third magnet 304, metal sheet 306 positioned between the second and third magnets and positioned above surface 308 of the assay consumable. In FIG. 12A, the darker colors represent relatively higher magnetic field strengths. Beads present on the surface 308 of the assay consumable will experience a force exerted on them that will tend to push the beads both down and towards the outer edges 309 of the assay consumable. The field strength as a function of position across surface 308 is shown in the plot in FIG. 12B. As will be understood by one of ordinary skill in the art, the force on a paramagnetic particle is proportional to the magnetic field gradient. The gradient along the line in FIG. 12B is a force away from the tip of the metal sheet 306 on either side of the sheet. The gradient from the magnet results in a force vector toward the magnet 300. The superposition of these two vectors means that a paramagnetic particle, in this field, sitting at a point along line 300 would experience a force vector that is generally perpendicular to the line on the plot in FIG. 12B pointing downward. It should be understood that the magnetic field maintains the same general shape in the area between the tip of the metal sheet and the first magnet, and thus, the consumable may be placed at varying heights between the tip of the metal sheet and the first magnet and experience similar magnetic field. For example, FIG. 12C shows a similar plot as to FIG. 12B, except in this plot, the surface of the consumable is at a different height as compared to in FIG. 12B (e.g., the surface in FIG. 12C is 0.5 mm above the surface in FIG. 12B). FIGS. 12D and 12E depict the magnetic squeegie wiper in operation. Assay consumable surface 308 includes magnetic beads 312 thereon, which are subject to magnetic force vectors 314 based on the magnetic field at the location of the bead. FIGS. 12D and 12E depict assay consumables with beads on the surface, placed at two different heights between the tip of the metal sheet and the first magnet, again showing that the forces between the tip of the metal sheet and the first magnet are approximately equal.

In yet another embodiment, the wiper may comprise a fluid injector configured to apply a fluid to the surface of the consumable containing the plurality of reaction vessels in a manner capable of removing the excess beads positioned on the surface of the assay consumable, but not contained within a reaction vessel. For example, as shown in FIGS. 8E and 8F, and as described in more detail below, sealing fluid 370 may act as both a sealing component and as a wiper to aid in the removal of beads 372 on the surface of the assay consumable in certain embodiments.

In yet another example, the wiper may comprise an adhesive sheet, wherein the adhesive sheet may be contacted with the surface of an assay consumable in a manner such that excess beads on the surface of the assay consumable stick to and are removed by the adhesive sheet.

Exemplary Sealers

In some embodiments, an assay system of the present invention may include a component and/or sub-system that is configured to be used for sealing a plurality of assay sites. In some cases the assay system comprises an assay consumable handler (e.g., as described herein), a sealer, and a controller configured to control operation of the sealer to apply a sealing component to the plurality of assay sites. The sealer may be constructed and positioned to apply the sealing component to the surface of the assay consumable, thereby forming a plurality of sealed assay sites. In some cases, following sealing of the plurality of assay sites, the contents of each of the sealed assay sites may be substantially fluidically isolated from the contents of each of the other plurality of sealed assay sites, as described herein.

The sealing component is a material applied to a surface of the assay consumable containing assay sites that is able to seal the assay sites and at least partially or temporarily isolate the contents of one assay site from at least one other assay site. The sealing component may be in solid, gel, and/or a liquid form and may be formed of any suitable material. In some cases, the sealing component comprises a film. Non-limiting examples films that a sealing component may comprise include solid films (e.g., of a compliant material), fluid films (e.g., of fluids substantially immiscible with sample fluid contained in the assay sites), or the like. Non-limiting examples of suitable materials for a solid sealing component include elastomers, such as silicas or silica oxides (e.g., PDMS, etc.), polymers (e.g., polyurethanes, COP, COC), latex rubber, synthetic rubbers, various natural and synthetic gels, pressure-sensitive adhesives, and tapes. In some cases, the surface of the solid materials are modified to produce better seal quality.

Depending on the characteristics of the sealing component, the sealer may be configured appropriately to apply the sealing component to a plurality of assay sites formed on a surface of an assay consumable. For example, for a sealing component that comprises a film formed of a compilable solid material, the film may be applied to the surface of the assay consumable by applying pressure, either uniformly or non-uniformly, to the sealing component when it is in contact with the surface. Pressure may be applied to the sealing component using any number of known methods. In a certain embodiment, a sealing component may be applied using a movable stage such that the sealing component and/or the consumable substrate are forced together to effect sealing.

Figure 13A:
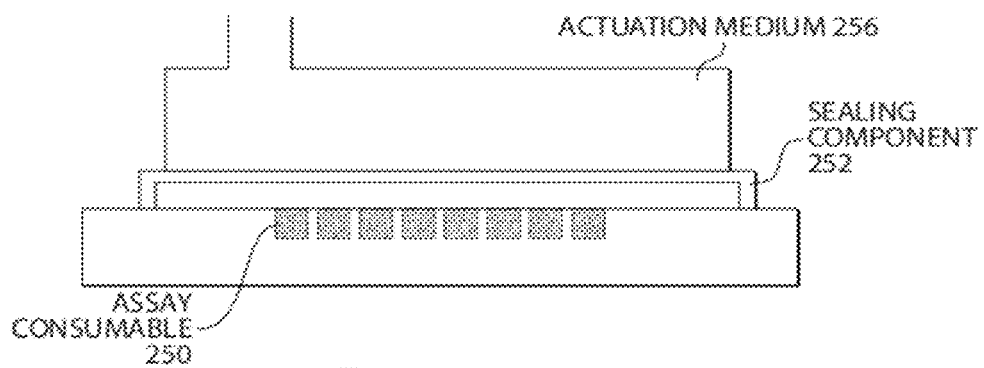
FIGS. 13A-13B are schematic diagrams showing a non-limiting example of a sealer comprising an actuator.
Figure 13B:
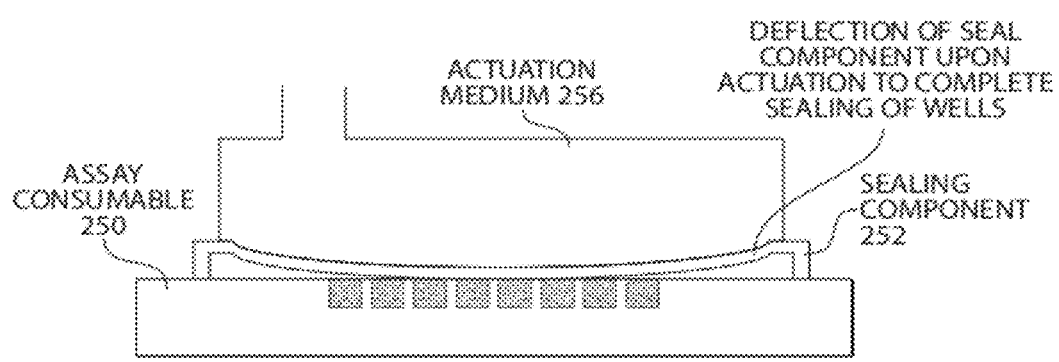

As another example, a device, such as a pneumatic or hydraulic device, using a fluid actuation medium may be employed. For example, as shown in FIGS. 13A and 13B, an assay system comprising assay consumable 250 comprising a plurality of assay sites and sealing component 252 is shown, wherein sealing component 252 is not in contact with the surface of assay consumable 250. The sealer comprising the sealing component also includes a force generator, comprising an actuation medium 256, in contact with sealing component 252, wherein actuation medium is capable of applying force to the sealing component and moving it towards the assay consumable. In FIG. 13B, the sealer is activated via a controller (not shown), e.g., by pressurizing a fluid comprising the actuation medium, so that the actuation medium 256 presses on and forces sealing component 252 into sealing contact with the surface of assay consumable 250 comprising a plurality of assay sites.

In certain embodiments, the sealer may comprise at least one roller. The roller may be moved across the surface of the sealing component such that the sealing component is progressively contacted with the entirety of the surface of the assay consumable containing assay sites. In some cases, the sealer may comprise more than one roller.

Figure 14A:
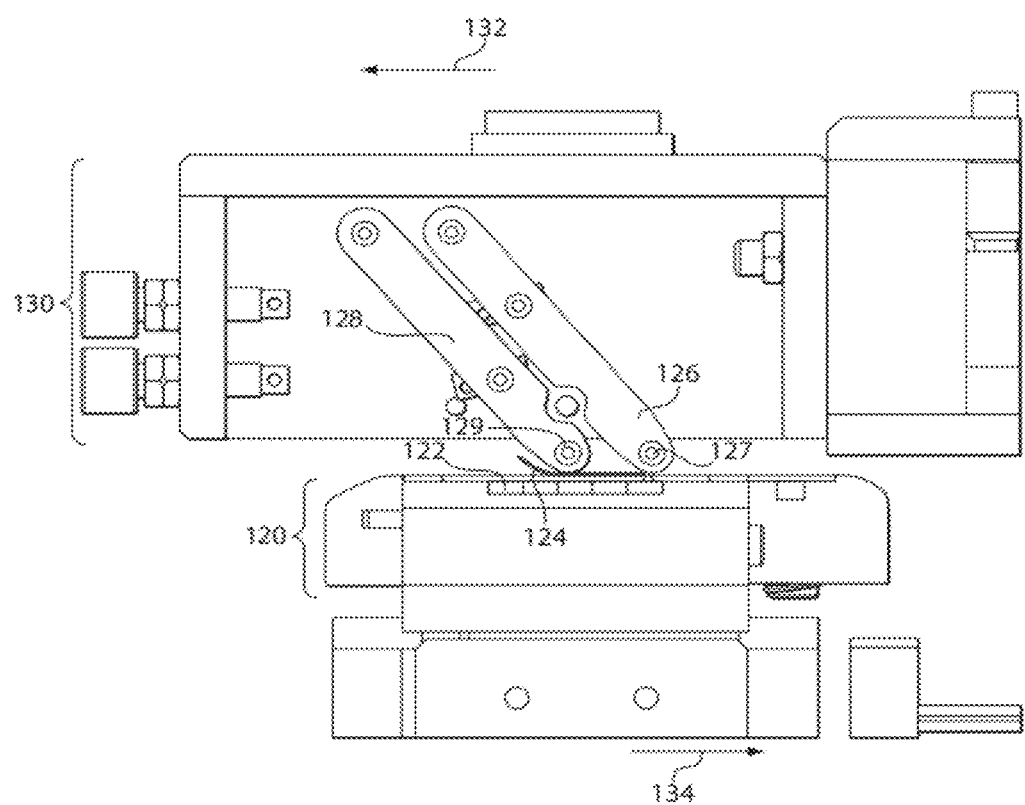
FIGS. 14A-14D are schematic diagrams showing an exemplary embodiment of a sealer of the present invention in various stages of sealing an assay consumable.

For example, as shown in FIG. 14A, sealer 130 comprises first roller assembly 126 and second roller assembly 128. First roller assembly 126 and second roller assembly 128 each comprising a roller (127 and 129) which are biased to be forced into contact with and extend across the width of (into the plan of the figure as drawn) sealing component 124. Sealing component 124 is positioned in adjacent to the upper surface of assay consumable 122, which is position and secured by consumable handler 120. The sealer may be moved in a direction, for example as shown by arrow 132, such that rollers 127 and 129 create sealing contact between sealing component 124 and assay consumable 122. In another example, sealer 130 may be stationary and assay consumable handler 120 associated with assay consumable 122 may be moved laterally, thereby causing rollers 127 and 129 to create sealing contact between sealing component 124 and assay consumable 122. FIG. 14D shows another view of the sealer in FIG. 14A, wherein a portion of the roller assemblies 126 and 128 are not shown so that the rollers 127 and 129 are shown extending across sealing component 122.

Figure 14B:
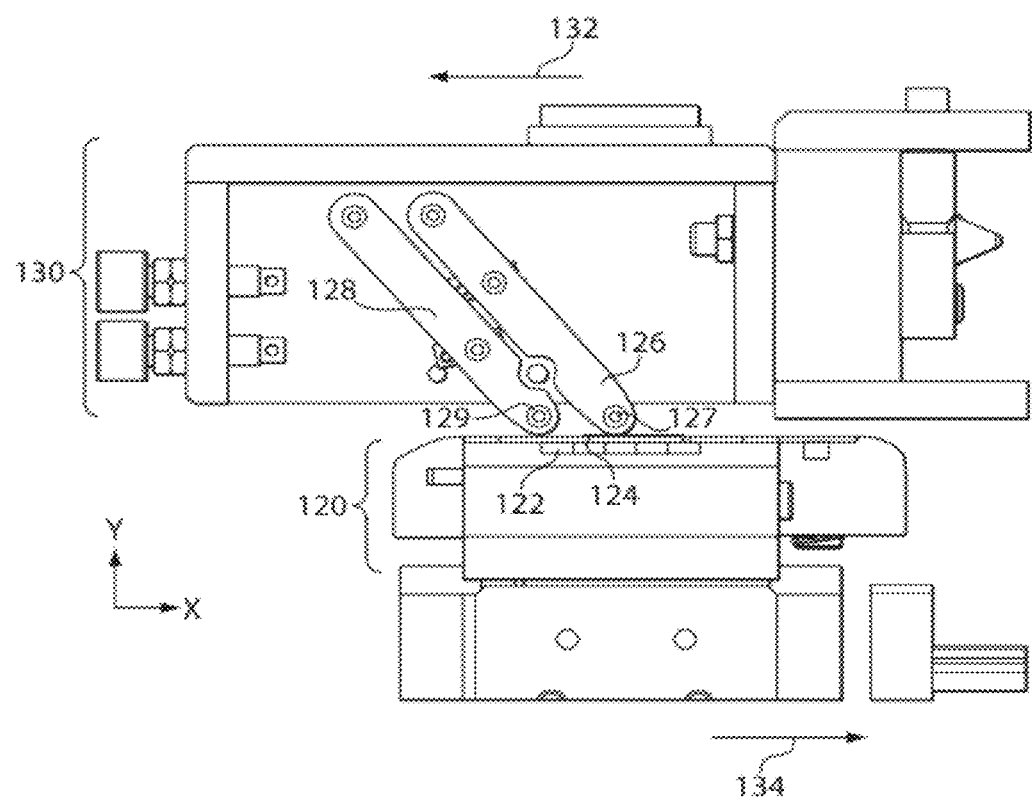
Figure 14C:
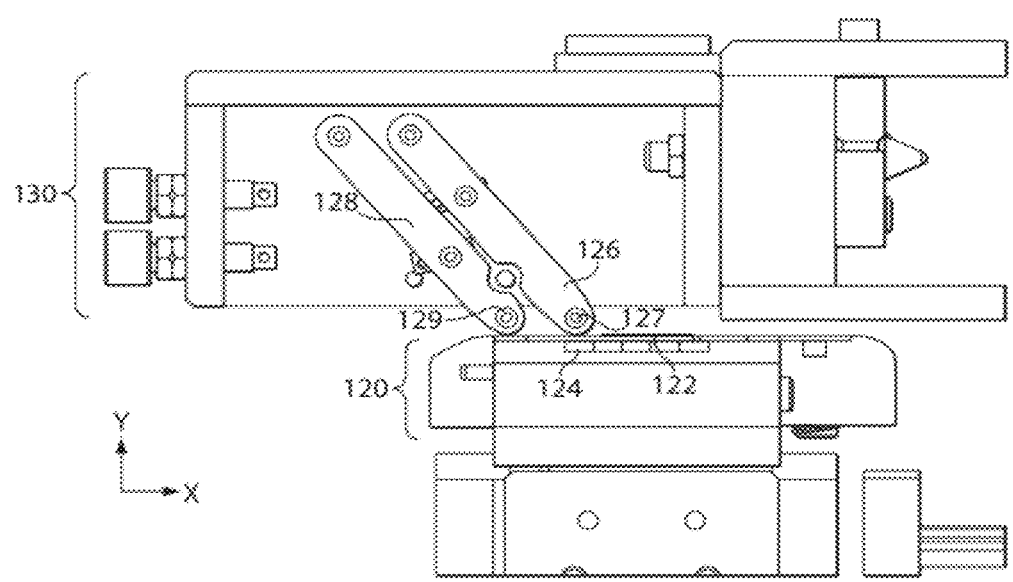
Figure 14D:
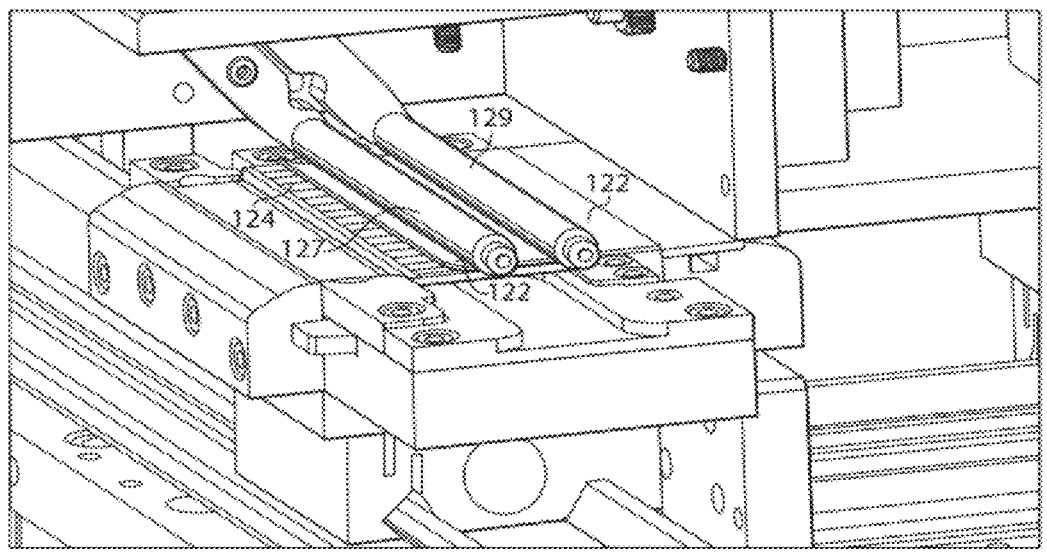

FIG. 14B shows a second configuration in which sealer 130 has already been moved relative to assay consumable handler 120 such that sealer component 124 is in substantially full contact with assay consumable 122 but roller 127 is still in contact with sealing component 124. FIG. 14C shows the configuration after the sealer has traversed its full range of sealing motion, in which rollers 129 and 127 are both no longer in contact with sealing component 124. Those of ordinary skill in the art will understand that sealer may comprise more or less than two rollers (e.g., one roller, three rollers, four, rollers, five rollers, etc.).

It should be noted, that in embodiments where the sealer comprises rollers which are moved across a sealing component in contact with an assay consumable surface, any excess fluid and/or beads not contained within wells on the surface may be pushed to one side of the sealing component (i.e. the sealer may also act as the wiper in some instances). In such embodiments, it may be beneficial to provide channels and/or openings in the surface of the assay consumable in contact with the sealing component, which may contain and channel away any excess fluids and/or beads which are removed while applying the sealing component.

In some cases, a sealing component comprises a pressure-sensitive adhesive. For example, the pressure-sensitive adhesive may be formed on one or more surfaces of a film. The pressure-sensitive adhesive may be activated upon application of the sealing component to the surface of the assay consumable containing the plurality of assay sites. The pressure-sensitive adhesive may form an adhesive bond between the sealing component and the surface of the assay consumable so that a seal is maintained even after force applied by the sealer is released (e.g., see the configuration of FIG. 14C).

In some embodiments, the sealing component may be a fluid. The fluid comprising the sealing component is advantageously substantially immiscible with the fluid contained in the assay sites. As used herein, a "fluid" is given its ordinary meaning, i.e., a liquid or a gas. The fluid may have any suitable viscosity that permits flow. If two or more fluids are present, the fluids may each be substantially miscible or substantially immiscible. In some cases, the fluid(s) comprising the sealing component can miscible or partially miscible with the assay sample fluid at equilibrium, but may be selected to be substantially immiscible with the assay sample fluid within the time frame of the assay or interaction. Those of ordinary skill in the art can select suitable sealing fluids, such as fluids substantially immiscible with sample fluids, using contact angle measurements or the like, to carry out the techniques of the invention. In some cases, the sample fluid and/or rinsing fluid and/or reagent fluid is an aqueous solution and the sealing component comprises a non-aqueous fluid. Non-limiting examples of potentially suitable non-aqueous fluids include fluorous liquids, oils (e.g., mineral oils, fluorinated oils), ferrofluids, non-aqueous polymer solutions (e.g., thickeners), and the like. In other cases, the sample fluid and/or rinsing fluid and/or reagent fluid is a non-aqueous solution and the sealing component comprising an aqueous fluid. In some cases, the sample fluid is a hydrogel whose viscosity changes upon temperature or other physicochemical triggers.

A fluid sealing component may be applied using a sealer which is configured and adapted to apply the fluid to a surface of an assay consumable containing assay sites. For example, the sealer may comprise a suitable liquid injection system, such as described above. In some cases, the sealer comprises a pipette, an automatic pipettor, an inkjet printer, or the like.

The example shown in FIG. 10 illustrates the use of a fluidic sealing component in combination with a wiper. In the illustrated system, a fluidic sealing component 274 is applied to the assay sites substantially immediately after removing excess beads from the surface of the assay consumable by wiper blade 272. Wiper blade 272 is in contact with assay consumable 270, and on one side of the wiper is sample fluid 276, while on the other side of the wiper is sealing liquid 274. As wiper blade 272 is moved from first Position A in FIG. 10A to second Position B in FIG. 10B, the sealing liquid is also applied.

The sealing component may be provided in such a set-up using any of the apparatus as described herein (e.g., fluid injected associated with a fluid pump). For example, a similar example is shown in FIGS. 8E and 8F. In FIG. 8E, assay consumable 348 comprising a plurality of assay sites 364 is positioned in a channel as indicated by roof of channel 356. Sealing fluid 370 is provided through an inlet (not shown), thereby substantially replacing sample fluid 368. The flowing of sealing fluid 370 may also act as a wiper. In FIG. 8F, sealing fluid 370 has substantially replace the sample fluid, and assay sites are sealed.

Other non-limiting examples of apparatus comprising a sealer for use with a sealing component comprising a liquid (also referred to as a sealing liquid) are shown in FIG. 3F (320) and FIG. 4A (60).

The use of a sealing fluid may be advantageous for the use of assay consumable shapes having substantially non-planar surfaces containing assay sites. Other potential beneficial features of fluid sealing components include: 1) substantial immiscibility of the sealing fluid and an assay fluid may allow for a creation of a total or near total barrier between assay sites preventing diffusion of a detecting molecule (e.g., a fluorophore) between assay sites; 2) the sealing fluid may be better at conforming to the surface of the certain assay consumables as compared to a certain solid sealing components; and 3) optical properties of the sealing fluid may cause less optical interference/distortion with certain imaging system.

Exemplary Imaging Systems

A variety of imaging systems potentially useful for practice of certain embodiments and aspects of the invention are known in the art and commercially available. Such systems and components may be adapted based upon the needs and requirements of a selected assay method being performed by the system and the technique used for detecting the analyte molecules and/or particles. For example, in some assays, the analyte molecules and/or particles are not directly detectable and additional reagents (e.g., detectable labels) are used aid in the detection. In such instances, components of the imaging system would be selected to detect such reagents.

In certain embodiments, the imaging system is configured to optically interrogate the assay sites. The sites exhibiting changes in their optical signature may be identified by a conventional optical train and optical detection system. Depending on the species to be detected and the operative wavelengths, optical filters designed for a particular wavelength may be employed for optical interrogation of the locations, as will be understood by those of ordinary skill in the art.

In embodiments where optical interrogation is used, the imaging system may comprise more than one light source and/or a plurality of filters to adjust the wavelength and/or intensity of the light source. Examples of light sources include lasers, continuous spectrum lamps (e.g., mercury vapor, halogen, tungsten lamps), and light-emitting diodes (LED). For example, in some cases, a first interrogation of the assay sites may be conducted using light of a first range of wavelengths, whereas a second interrogation is conducted using light of a second, differing range of wavelengths, such that the plurality of detectable molecules fluoresce. An exemplary system configuration is described below (see FIG. 15).

In some embodiments, the optical signal from a plurality of assay sites is captured using a CCD camera. Other non-limiting examples of devices that can be used to capture images include charge injection devices (CIDs), complimentary metal oxide semiconductors (CMOSs) devices, scientific CMOS (sCMOS) devices, time delay integration (TDI) devices, photomultiplier tubes (PMT), and avalanche photodiodes (APD). Camera variety of such devices are available from a number of commercial vendors. The detection devices (e.g., cameras) can be fixed or scanning.

In one embodiment, the assay consumable comprises a fiber optic bundle, and a plurality reaction vessels is formed in an end of the fiber optic bundle. According to one embodiment, the array of assay sites for the present invention can be used in conjunction with an optical detection system such as the system described in U.S. Publication No. 2003/0027126.

Figure 15A:
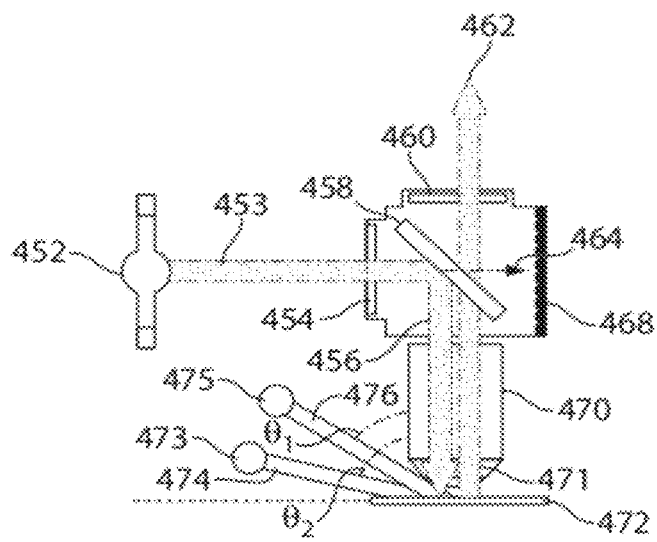
FIGS. 15A-15B are schematic diagrams showing a non-limiting example of an imaging system.
Figure 15B:
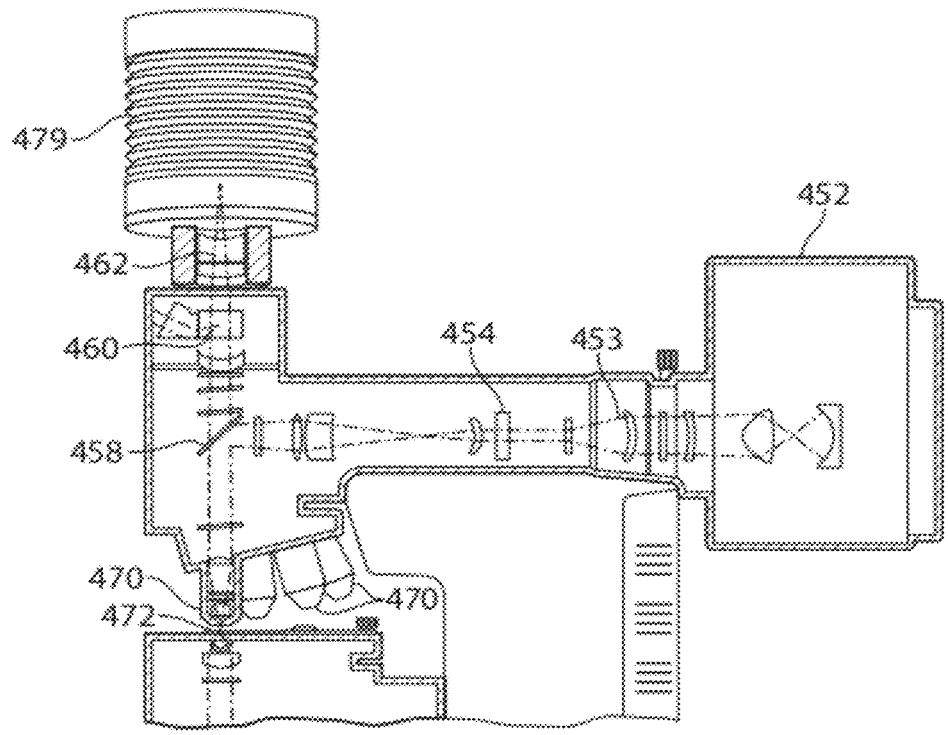
Figure 16A:
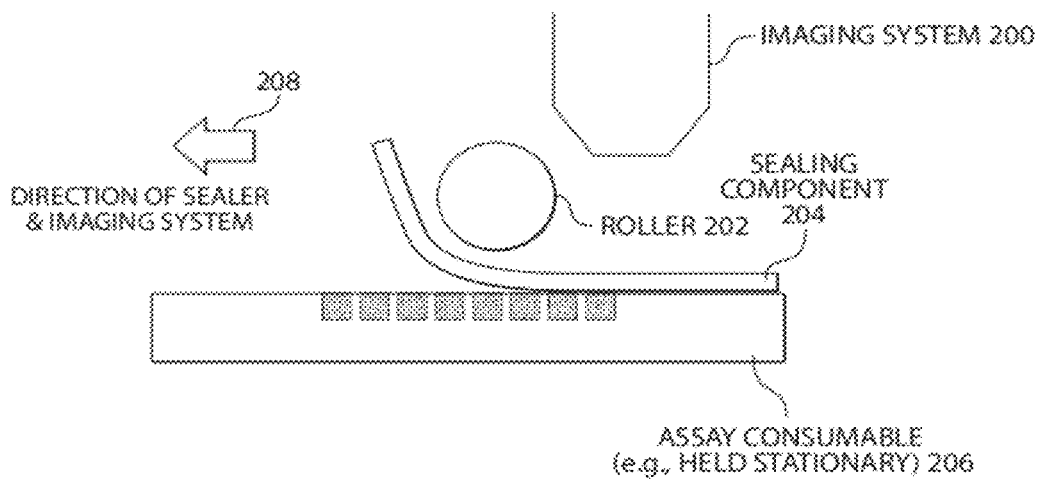
FIGS. 16A-16F are schematic diagrams showing exemplary approaches which can be used for sealing and imaging an assay consumable substantially simultaneously.
Figure 16B:
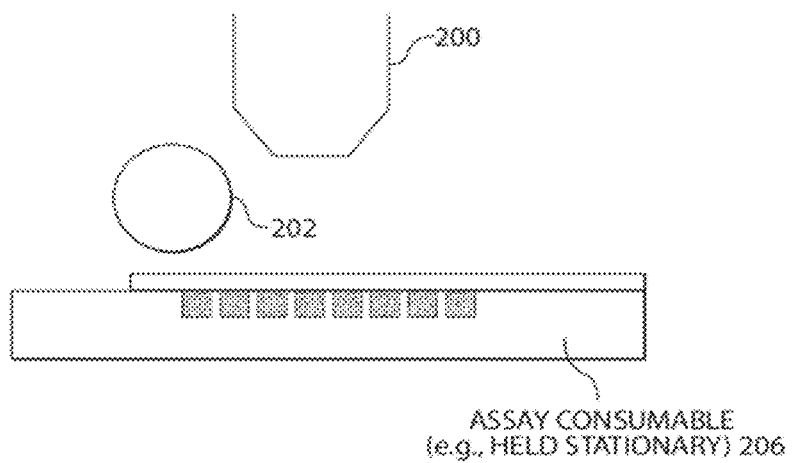
Figure 16C:
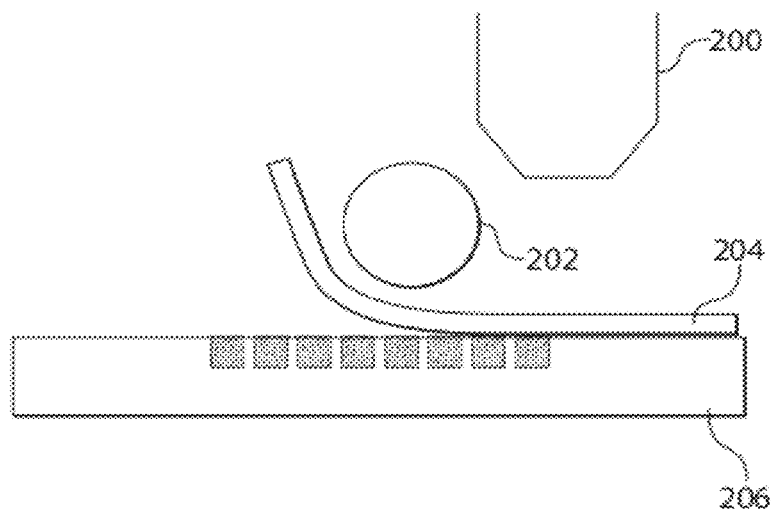
Figure 16D:
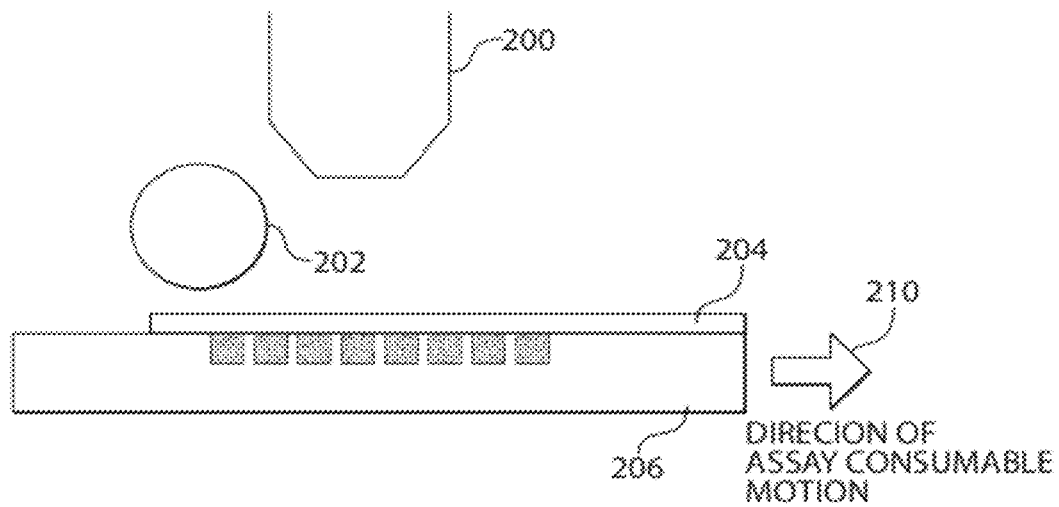
Figure 16E:
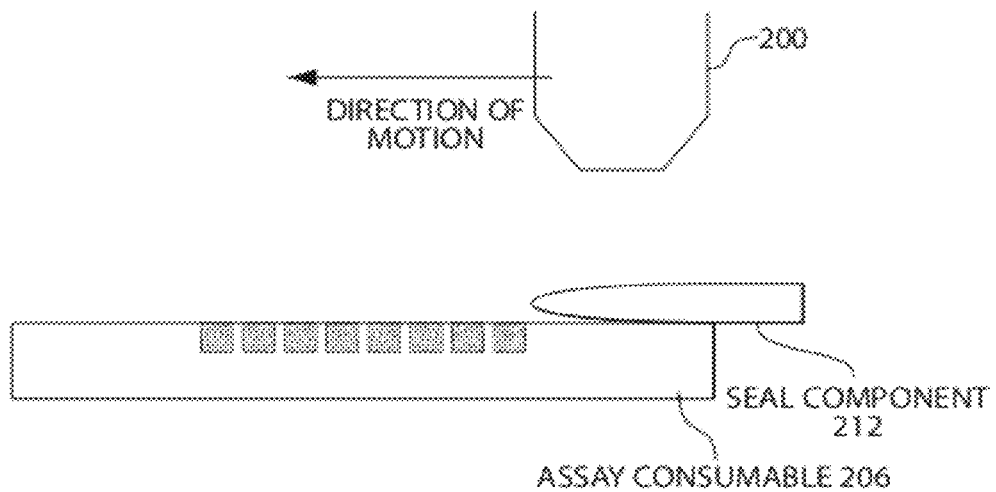
Figure 16F:
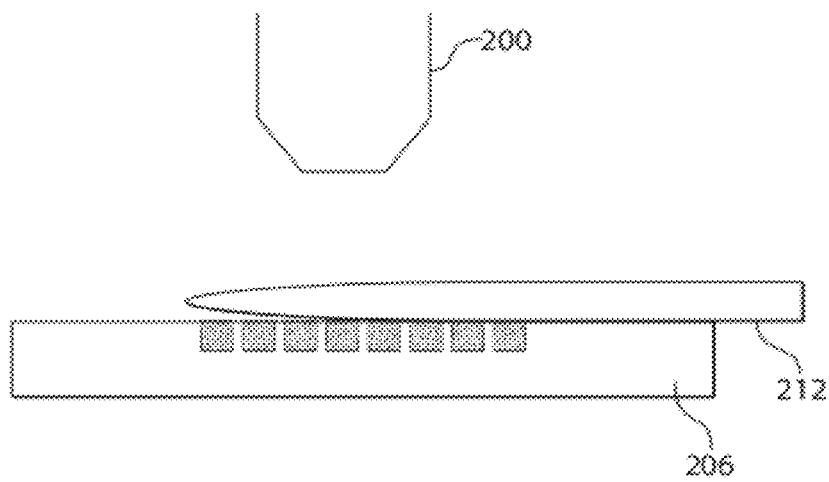

FIGS. 15A and 15B show a non-limiting example of an imaging system. The system comprises a light source 452, excitation filter 454, dichromatic mirror 458, emission filter 460 and objective 470. The objective is positioned to interrogate assay sites on assay consumable 472. Light 453 from light source 452 passes through excitation filter 454. The light reflects off dichromatic mirror 458, passes through objective 470 and shines on the assay consumable surface comprising a plurality of assay sites. In some cases, stray light 464 may be reduced by a stray light reducing component 468, such as an iris or aperture. Light 471 emitted from the assay consumable passes through objective 470 and emission filter 460 to produce a processed light signal 462, which is observed, processed and/or recorded. The system may comprise additional components (e.g., additional filters, mirrors, magnification devices, etc.) as needed for particular applications, as would be understood by those of ordinary skill in the art.

The system shown in FIG. 15A may additionally comprise components which aid in the determination of the number of assay sites which contain a bead (e.g., using white light or a turret containing filters capable of measuring the fluorescence of different fluorescently labeled beads). Additional components may also be used to determine the total number of assay sites and/or provide spatially information regarding the position of the assay sites (e.g., those containing or not containing a bead), which may help corroborate signals observed under different light regimes (e.g., fluorescence, white light) corresponding with the position of a reference location (e.g., a mask may be created).

In FIGS. 15A and 15B, excitation light is emitted from source 452 and collimated into a beam 453. The excitation filter 454 may be configured to transmit only the wavelength band that excites a particular fluorophore (e.g., 575 nm+/−10 nm for resorufin). The excitation light is reflected downward by the dichroic filter 458 and illuminates the assay consumable surface comprising a plurality of assay sites containing the sample through the objective lens 470. The emitted image light is collected by the objective lens 470, collimated into a beam 471 and transmitted through the dichroic filter 458. Only the image light corresponding to the fluorescence wavelength band (e.g., 620 nm+/−30 nm for resorufin) is transmitted through the emission filter 460. The remaining collimated beam 462 contains only the emitted fluorescence wavelengths which will subsequently be imaged through the camera system.

The same imaging system may be used to determine the positioning of the assay sites on the consumable surface (e.g., reaction vessels) containing sample. The assay sites containing beads may be illuminated with a "bright field" white light illumination. The assay consumable surface comprising a plurality of assay sites may be illuminated (e.g., using light source 475 shown in FIG. 15A) by directing a pseudo-collimated white light (e.g., white light LED) onto the assay consumable surface comprising a plurality of assay sites from an angle (e.g., $\theta_1$ in FIG. 15A may be about 20 degrees, about 25 degrees, about 30 degrees, about 35 degrees, about 40 degrees, or greater) just outside the numerical aperture of the collection objective. Light that hits the assay consumable surface comprising a plurality of assay sites 472 (e.g., light 476) is reflected (and scattered) off the surface, collimated 471, and collected by the objective lens (470). The collimated beam is subsequently imaged through the camera system.

The same imaging system may also be used to determine which assay sites contain a bead. It should be understood, that in some embodiments, more than one type of bead may be employed (e.g., a first type of bead and a second type of bead, wherein the first type of bead has a fluorescence emission different from the second type of bead) and in certain of such embodiments, the inventive assay systems are configured to perform multiplexed assays. Any particular bead may or may not be associated with an analyte molecule. The assay consumable surface comprising a plurality of assay sites may be illuminated (e.g., using light source 473 as shown in FIG. 15A) with a "dark field" white light illumination. The assay consumable surface comprising a plurality of assay sites may be illuminated by aiming a pseudo-collimated white light (e.g., white light LED 473) onto the surface of the assay consumable comprising a plurality of assay sites from an angle (e.g., $\theta_2$ in FIG. 15A is about 65 degrees, about 70 degrees, about 75 degrees, about 80 degrees, about 85 degrees) substantially outside the numerical aperture of the collection objective. Light that hits the surface of the assay consumable comprising a plurality of assay sites 472 (e.g., light 474) is reflected (and scattered) off the surface, collimated 471, and collected by the objective lens 470. The collimated beam is subsequently imaged by the camera system 479.

In some embodiments, an optical detection system may be employed that is similar to that described in U.S. Publication No. 2003/0027126, herein incorporated by referenced. In an exemplary system, light returning from an array of reaction vessels formed at the distal end of an assay consumable comprising a fiber optic bundle is altered via use of a magnification changer to enable adjustment of the image size of the fiber's proximal or distal end. The magnified image is then shuttered and filtered by a shutter wheel. The image is then captured by charge coupled device (CCD) camera. A computer implemented system may be provided that includes and executes imaging processing software to process the information from the CCD camera and also optionally may be configured to control shutter and filter wheels.

Those of ordinary skill in the art will be aware that various components of the imaging system can be adapted and/or configured to provide a good image. For example, in some cases, the assay consumable is imaged through a sealing component, and thus, the imaging system can be adapted and/or configured to account for the presence of the sealing component in the optical path. As will be known to those of ordinary skill in the art, certain thickness of material may lead to spherical aberration and loss of resolution of the arrays. Therefore, if the sealing component is of a thickness where such aberrations occur, the optical portion of the imaging system may be designed to correct for this increased thickness. Designing the optics such that fluid that matches the index of the seal material may be placed between the objective and the assay consumable is used so that differences in the material between the objective and the seal do not lead to blurring.

As another example of an aspect of the imaging system which may be configured and/or adapted to improve performance is the speed and quality of focus of the imaging system. In some cases, focusing may involve using a laser focusing system based on reflection off the assay consumable surface. Laser focusing systems are commercially available. In other cases, the surface of the assay consumable comprising assay sites (which may be similar in size as the wavelength of light being processed) may include structures/fiducials built in to the assay consumable that may be used to focus the image via diffraction, refraction, absorption, reflection, fluorescence, or a combination of these and other optical phenomena.

In some cases, all of the surface or essentially all of the surface of the assay consumable comprising assay sites may be imaged at a single time. In some cases, however, only a portion of the surface of the assay consumable comprising assay sites may be imaged at a time, and other portions may be imaged in a sequential fashion to build an image of the entire surface.

In some embodiments (e.g., wherein the sealing component is applied to the surface of the assay consumable in a progressive fashion, for example as described above in the context of the embodiment illustrated in FIGS. 14A-14C when applying a sealing component using a roller or when the sealing component is a moving front of a bolus of sealing liquid), sequential imaging may allow reduction in the time between sealing of the assay sites and imaging of the sealed assay sites. In such cases, for example, imaging of an assay site may be completed immediately following sealing of an assay site (e.g., by application of a sealing component) by scanning the imaging system across the array of assay sites as they are sealed (e.g., like a photographic line scanner) as opposed waiting until sealing of the entire array is completed to interrogate all or substantially all of the assay sites at one time.

As an non-limiting example, FIGS. 16A-16F depict such a technique in action. These figures depict a cartoon of a system comprising an imaging system 200, roller 202 (e.g., a portion of a sealer), sealing component 204, and assay consumable 206. In this system, assay consumable 206 is held stationary, and imaging system 208 and roller 202 are configured such that substantially immediately after roller 202 has applied sealing component 204 to assay sites on a particular portion of assay consumable 206, imaging system 200 obtains an image of those assay sites. Thus, imaging system 202 and roller 202 move substantially simultaneously (e.g., see arrow 208) across the array of assay sites. In another embodiment, shown in FIG. 16C and FIG. 16D imaging system 200 and roller 202 are held stationary and assay consumable 210 is moved (e.g., see arrow 210) to achieve the same result. In still yet another embodiment depicted in, FIG. 16E and FIG. 16F sealing component 212 is a liquid. This system is configured so that imaging system 200 moves at a similar speed at does sealing fluid 212. The synchronized motion of the imaging system 200 and the sealing fluid 212 can allow for the sealing and imaging to occur substantially simultaneously. In this example, the assay consumable is held stationary.

The imaging system may be associated with a computer implemented control system that may be separate from or the same as other of the controllers of the system. The computer implemented control system can perform or be configured to control a variety of components, including being configured to automatically operate the sealer (and optionally one, several or all of the other components of the overall system associated with a controller) and receive information from the imaging system related to the image. In some cases, the computer is further configured to determine a measure of the unknown concentration of the analyte molecule in the assay sample. The controller may be able to determine a measure of the unknown concentration of analyte molecules or particles in the assay sample, at least in part, based on the fraction of the at least a portion of the assay sites interrogated which contain zero or one analyte molecules or particles. Further information regarding the structure and configuration of the computer implemented control systems is provided below.

Exemplary Assay Consumables

The assay consumable may be configured in a wide variety ways. The particular shape, size, and other parameters of the assay consumable can be selected to function well within the constraints of the configurations of the other components of the assay system with which the assay consumable is to be used, for example the configuration and design of the assay consumable handler, the sample loader, the rinser, the sealer, the bead loader, the imaging system, etc. Similarly, the configurations of other assay system components should be selected to be compatible with the design characteristics of the assay consumable. Several exemplary assay consumable configurations were discussed previously in the context of the description associated with the systems of FIG. 3B (38), FIG. 4C (60), FIG. 2A (398), FIG. 2B (410), FIG. 2C (432), FIG. 2D (439), FIG. 5A (500), FIG. 5E (550), etc. In some assay consumable embodiments, the plurality of assay sites comprises a plurality reaction vessels/wells on a substrate. The reactions vessels, in certain embodiments, may be configured to receive and contain only a single bead (e.g., as described below) or more than one bead. In some embodiments of the assay consumable, the plurality of reaction vessels may be sealed using a sealer comprising a seal component that is separate from or integrated into the structure of the assay consumable itself. The sealing of the reaction vessels may be such that the contents of each reaction vessel cannot escape the reaction vessel during the remainder of the assay. In some cases, the reaction vessels may be sealed after the addition of sample, assay beads and, optionally, additional reagents (e.g., to facilitate detection of the analyte molecules and/or particles in the sample).

A plurality of reaction vessels may be formed on a surface of the assay consumable using a variety of methods and/or materials. In some cases, the plurality of reaction vessels is formed as an array of depressions on a surface. In other embodiments, the portions of the surface of the assay consumable surrounding the assay sites may be on the same level as the assay sites. For example, in some cases, the assay consumable includes a surface that is substantially planar and the assay sites formed on the surface and the area surrounding the assay sites are at substantially similar levels.

In some cases, the areas surrounding the surface containing assay sites or reaction vessels/wells is raised, such that the assay sites/wells are contained in a channel on or in the assay consumable. The channel may be an open (e.g., uncovered like a trough) or closed (e.g., enclosed like a tube or conduit).

Any of the assay consumable components, for example, the surface containing assay sites or any sealing component, may be fabricated from a compliant material, e.g., an elastomeric polymer material, to aid in sealing. The surfaces may be or made to be hydrophobic or contain hydrophobic regions to minimize leakage of aqueous samples from the assay sites (e.g., microwells).

Sealing component may be essentially the same size as the surface containing assay sites or may be different in size. In some cases, the sealing component is approximately the same size as the surface containing assay sites and mates with substantially the entire surface of the surface containing assay sites. In other cases, the sealing component is smaller than the surface containing assay sites and/or the sealing component only mates with a portion of the surface containing assay sites.

In some embodiments, the assay sites are wells that may all have approximately the same volume. In other embodiments, the wells may have differing volumes. The volume of each individual well may be selected to be appropriate to facilitate any particular assay protocol. For example, in one set of embodiments where it is desirable to limit the number of beads per well, the volume of the wells may range from attoliters or smaller to nanoliters or larger depending upon the size and shape of the beads, the detection technique and equipment employed, the number and density of the assay sites on the substrate, and the expected concentration of beads in the fluid applied to the surface containing the wells, etc. In one embodiment, the size of the wells may be selected such only a single bead used for analyte capture can be fully contained within the well. In accordance with one embodiment of the present invention, the assay sites (e.g., reaction vessels/wells) may have a volume between about 1 femtoliter and about 1 picoliter, between about 1 femtoliters and about 100 femtoliters, between about 10 attoliters and about 100 picoliters, between about 1 picoliter and about 100 picoliters, between about 1 femtoliter and about 1 picoliter, or between about 30 femtoliters and about 60 femtoliters. In some cases, the assay sites (e.g., reaction vessels) have a volume of less than about 1 picoliter, less than about 500 femtoliters, less than about 100 femtoliters, less than about 50 femtoliters, or less than about 1 femtoliter. In some cases, the reaction vessels have a volume of about 10 femtoliters, about 20 femtoliters, about 30 femtoliters, about 40 femtoliters, about 50 femtoliters, about 60 femtoliters, about 70 femtoliters, about 80 femtoliters, about 90 femtoliters, or about 100 femtoliters.

In embodiments where the plurality of assay sites comprise a plurality of reaction vessels/wells having a shape that is essentially that of a circular cylinder, the size of the assay sites may be based upon the size of any beads that will be used in an assay protocol and may be designed so as to ensure that the number of wells containing more than a single bead is minimal. In some cases, the maximum permissible well (e.g., assay site) diameter may be calculated according to Equation 3:

$$2*BeadRadius + \sqrt{(3*BeadRadius^2 - WellDepth^2 + 2*WellDepth*BeadRadius)} \quad (Eq.\ 3)$$

and/or the maximum permissible well (e.g., assay site) depth may be calculated according to Equation 4:

$$BeadRadius + \sqrt{(4*BeadRadius*WellDiameter - WellDiameter^2)} \quad (Eq.\ 4)$$

The minimum permissible well (e.g., assay site) depth and the minimum permissible well diameter (e.g., assay site) to assure that a single bead can be contained in the well (e.g., assay site), in most embodiments, will not be less than the average diameter of the bead. Having a properly sized reaction vessel which allows for no more than a single bead to be present in a reaction vessel may provide better ability to resolve individual beads allowing for more accuracy with regard to determining a measure of the concentration of analyte molecules in a sample fluid in certain assays.

In some embodiments, the average depth of the wells is between about 1.0 and about 1.7 times, between about 1.0 times and about 1.5 times, between about 1.0 times and about 1.3 times, or between about 1.1 times and about 1.4 times the average diameter of the beads. In some embodiments, the average diameter of the assay sites is between about 1.0 times and about 1.9 times, between about 1.2 times and about 1.7 times, between about 1.0 times and about 1.5 times, or between about 1.3 times and about 1.6 times the average diameter of the beads. In a particular embodiment, the average depth of the assay sites is between about 1.0 times and about 1.5 times the average diameter of the beads and the average diameter of the assay sites is between about 1.0 times and about 1.9 times the average diameter of the beads.

The total number of assay sites and/or density of assay sites present on the surface of an assay consumable can depend on the composition and end use of the assay consumable. For example, the number of assay sites employed may depend on the whether beads are employed in the assay to be performed, if so the number of beads to be used, the suspected concentration range of analyte in the sample(s) to be tested with the assay, the method of detection, the size of any beads, the type of detection entity (e.g., free labeling agent in solution, precipitating labeling agent, etc.). Assay consumables containing from about 2 to many billions of assay sites (or total number of assay sites) can be made by utilizing a variety of techniques and materials. The assay consumable may comprise between one thousand and one million assay sites per sample to be analyzed. In some cases, the assay consumable comprises greater than one million assay sites. In some embodiments, the assay consumable comprises between about 1,000 and about 50,000, between about 1,000 and about 1,000,000, between about 1,000 and about 10,000, between about 10,000 and about 100,000, between about 100,000 and about 1,000,000, between about 100,000 and about 500,000, between about 1,000 and about 100,000, between about 50,000 and about 100,000, between about 20,000 and about 80,000, between about 30,000 and about 70,000, between about 40,000 and about 60,000, or the like, assay sites. In some embodiments, the assay consumable comprises about 10,000, about 20,000, about 50,000, about 100,000, about 150,000, about 200,000, about 300,000, about 500,000, about 1,000,000, or more, assay sites.

The array of assay sites may be arranged on a substantially planar surface or in a non-planar three-dimensional arrangement. The assay sites may be arrayed in a regular pattern or may be randomly distributed. In a specific embodiment, the assay consumable is a regular pattern of sites on a substantially planar surface permitting the assay sites to be addressed in the X-Y coordinate plane. The array may also contain fiducial features (e.g., unique shapes of wells, fluorescently doped wells, etc.) that enable multiple images and arrays to be aligned.

In some cases, a plurality of assay sites on an assay consumable may be partially surrounded or completely surrounded by at least one channel and/or moat. The channel and/or moat may help to contain liquid (e.g., a sample fluid) that overflows from the array, and/or may aid in directing excess fluid removal and/or flow (e.g., during sealing of the array with a sealing component). For example, FIG. 2H shows open channel/trough 33 partially surrounding array 34 on a single side thereof, FIG. 2I shows channel 33 partially surrounding array 34 on three sides, and FIG. 2J shows channel 33 completely surrounding array 34. A portion of the assay consumable not comprising any assay sites may or may not be present between the channel and the assay sites. In FIGS. 2H-2K, a area 53 is present between channel 33 and the area comprising assay sites 34. The size of the channel (e.g., width, depth, length), the shape of the channel, and/or the proximity of the channel to the array (e.g., how much distance is between the assay sites and the channel) may be selected based on the parameters of the specific set-up of the system (e.g., based on the amount of fluid provided, etc.). The channel may or may not have the same shape (e.g., width, depth) throughout the entire length of the channel. For example, FIG. 2K shows channel 33 partially surrounding array 25, wherein segment 36 of the channel are narrower and/or shallower than segment 37. Those of ordinary skill in the art will be able to determine other appropriate variations, for example, segments 36 may be wider/deeper than segment 37. Arrow 35 in FIGS. 2H-2K indicate the direction of application of a sealing component, in some cases. In embodiments where the sealing component is applied directionally (e.g., as indicated by arrow 35), the channel/trough segment on the side of the array where the sealing component is last applied (e.g., 51) can be larger (e.g., wider, deeper, etc.) as compared to the other segments of the channel (e.g., such that any fluid being forced across the array due to application of the sealing component is channeled into and fully contained that segment of the channel). In some cases, the channel may be fluidically connected to a waste collection receptacle (e.g., such that there is not build-up of liquid in the channel).

In some embodiments, the assay sites are formed in a solid material. As will be appreciated by those skilled in the art, the number of potentially suitable materials in which the assay sites can be formed is very large, and includes, but is not limited to, glass (including modified and/or functionalized glass), plastics (including acrylics, polystyrene and copolymers of styrene and other materials, polycarbonate, polypropylene, polyethylene, polybutylene, polyurethanes, cyclic olefin copolymer (COC), cyclic olefin polymer (COP), poly(ethylene terephthalate) (PET), Teflon®, polysaccharides, nylon or nitrocellulose, etc.), elastomers (such as poly(dimethyl siloxane) and poly urethanes), composite materials, ceramics, silica or silica-based materials (including silicon and modified silicon), carbon, metals, optical fiber bundles, or the like. In certain embodiments, the substrate material may be selected to allow for optical detection without appreciable autofluorescence. In certain embodiments, the assay sites may be formed in a flexible material.

Assay sites in a surface may be formed using a variety of techniques known in the art, including, but not limited to, photolithography, embossing/stamping techniques, molding techniques, etching techniques, micromachining, or the like. As will be appreciated by those skilled in the art, the technique used can depend on a variety of factors such as the composition and shape of the material(s) forming the assay consumable and the size, number, shape, density and pattern/distribution of assay sites.

In a particular embodiment, an assay consumable comprising a plurality of assay sites is formed by creating microwells on one end of a fiber optic bundle and utilizing a planar compliant surface as a sealing component. Those of skilled in the art will be aware of methods for creating reaction vessels in the end of a fiber optic bundle. For example, the diameter of the optical fibers, the presence, size and composition of core and cladding regions of the fiber, and the depth and specificity of the etch may be varied by the etching technique chosen so that microwells of the desired volume may be formed. In certain embodiments, the etching process creates microwells by preferentially etching the core material of the individual glass fibers in the bundle such that each well is approximately aligned with a single fiber and isolated from adjacent wells by the cladding material. Potential advantages of the fiber optic array format is that it can produce thousands to millions of reaction vessels without complicated microfabrication procedures and that it can provide the ability to observe and optically address many reaction vessels simultaneously. Methods of forming and advantage regarding fiber optic arrays will be know to those of ordinary skill in the art, for example, as described in those described in U.S. Patent Application Publication No. US-2007-0259448 (Ser. No. 11/707,385), filed Feb. 16, 2007, entitled "METHODS AND ARRAYS FOR TARGET ANALYTE DETECTION AND DETERMINATION OF TARGET ANALYTE CONCENTRATION IN SOLUTION," by Walt et al.; U.S. Patent Application Publication No. US-2007-0259385 (Ser. No. 11/707,383), filed Feb. 16, 2007, entitled "METHODS AND ARRAYS FOR DETECTING CELLS AND CELLULAR COMPONENTS IN SMALL DEFINED VOLUMES," by Walt et al.; U.S. Patent Application Publication No. US-2007-0259381 (Ser. No. 11/707,384), filed Feb. 16, 2007, entitled "METHODS AND ARRAYS FOR TARGET ANALYTE DETECTION AND DETERMINATION OF REACTION COMPONENTS THAT AFFECT A REACTION," by Walt et al.; International Patent Application No. PCT/US2007/019184, filed Aug. 30, 2007, entitled "METHODS OF DETERMINING THE CONCENTRATION OF AN ANALYTE IN SOLUTION," by Walt et al.; U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE," by Duffy et al.; U.S. Patent Application Publication No. US-2010-00754072 (Ser. No. 12/236,486), filed Sep. 23, 2008, entitled "ULTRA-SENSITIVE DETECTION OF MOLECULES ON SINGLE MOLECULE ARRAYS," by Duffy et al., U.S. Patent Application Publication No. US-2010-0075439 (Ser. No. 12/236,488), filed Sep. 23, 2008, entitled "ULTRA-SENSITIVE DETECTION OF MOLECULES BY CAPTURE-AND-RELEASE USING REDUCING AGENTS FOLLOWED BY QUANTIFICATION," by Duffy et al.; U.S. Patent Application Publication No. US-2010-0075355 (Ser. No. 12/236,490), filed Sep. 23, 2008, entitled "ULTRA-SENSITIVE DETECTION OF ENZYMES BY CAPTURE-AND-RELEASE FOLLOWED BY QUANTIFICATION," by Duffy et al.; U.S. patent application Ser. No. 12/731,130, filed Mar. 24, 2010, entitled "ULTRA-SENSITIVE DETECTION OF MOLECULES OR PARTICLES USING BEADS OR OTHER CAPTURE OBJECTS," by Duffy et al.; U.S. patent application Ser. No. 12/731,135, filed Mar. 24, 2010, entitled "ULTRA-SENSITIVE DETECTION OF MOLECULES USING DUAL DETECTION METHODS," by Duffy et al.; of U.S. patent application Ser. No. 12/731,136, filed Mar. 24, 2010, entitled "METHODS AND SYSTEMS FOR EXTENDING DYNAMIC RANGE IN ASSAYS FOR THE DETECTION OF MOLECULES OR PARTICLES," by Duffy et al.; each herein incorporated by reference Alternatively, reaction vessels may be spotted, printed or photolithographically fabricated onto an assay consumable surface by techniques known in the art; see for example WO95/25116; WO95/35505; PCT US98/09163; U.S. Pat. Nos. 5,700,637, 5,807,522, 5,445,934, 6,406,845, and 6,482,593, each herein incorporated by reference.

In certain embodiments, an assay consumable of the invention may be configured to comprise a plurality of surfaces containing a group of assay sites, wherein each plurality of surfaces containing a group of assay sites is spatially separated from other such surfaces, for example by being contained in a series of spatially isolated chambers (e.g., such that each group of assay sites may be fluidically isolated from each other group of assay sites and/or such that each group of assay sites contains a distinct sample). In some such embodiments, an assay consumable may comprise a plurality of spatially separated chambers, wherein each of the spatially separated chambers contains a surface comprising a plurality of assay sites. That is, the assay consumable comprises a plurality of areas wherein each area contains a plurality of assay sites.

Figure 2A:
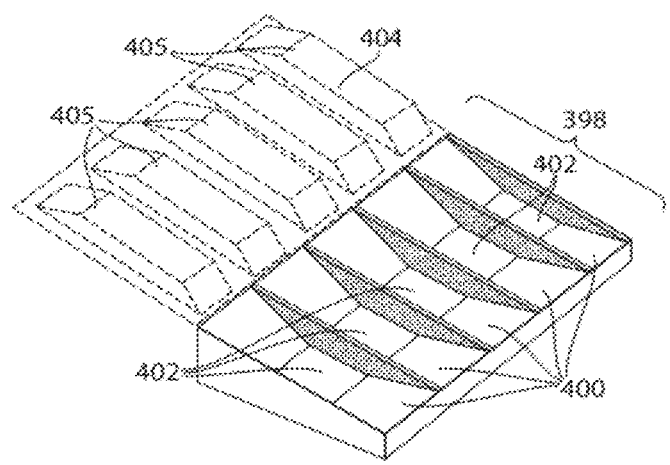
FIGS. 2A-2G are schematic diagrams showing non-limiting examples of assay consumable configurations.

For example, FIG. 2A shows assay consumable 398 comprising a plurality of spatially separated chambers 400, wherein each spatially separated chamber comprises a surface 402 containing a plurality of assay sites. In this example, the assay consumable may optionally includes a lid 404 comprising sealing components 405 constructed and positioned to be engagable with and disengagable from the spatially separated chambers 400. Upon engagement of the sealing components 405, each of spatially separated chambers become fluidicially isolated from the other chambers and each of the assay sites in each of the fluidically isolated chambers becomes fluidically isolated from the other assay sites in the same fluidically isolated chamber.

Figure 2B:
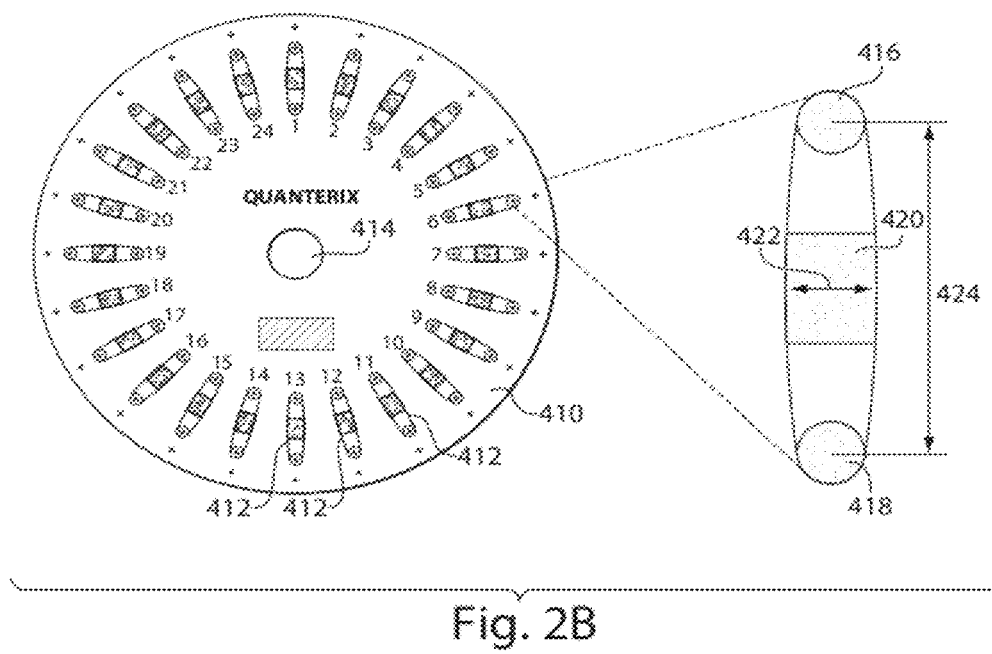

Another example of an assay consumable comprising a plurality of spatially isolated chambers and configured in the form of a disc is shown in FIG. 2B. Such discs may be manufactured by high volume processes such as injection molding and embossing that are used to manufacture CDs and DVDs. The assay consumable disc 410 includes a plurality of chambers 412, each comprising a surface containing a plurality of assay sites, which chambers are situated about disc 410. The disc may be configured to associate with an assay consumable handler, as described herein (e.g., such that the disc can rotate about center 414). Each chamber 412 comprises a channel, wherein the assay sites are positioned within the channel (e.g., an open or closed channel) on surfaces 420. In a particular embodiment, the channel is closed. The expanded portion of FIG. 2B shows a detail view of a single chamber 412 comprising a first opening 416, second opening 418, and a plurality of assay sites formed in surface 420. The sample as well as other fluids, e.g., bead containing fluids, rinsing fluids, sealing fluids, reagents, etc. may be introduced into the channel through the openings. The sizing of the channel may be selected based upon the particular needs of the assay and/or other system components, bead size, etc. In some cases, the channel has a width 422 and/or depth of between about 1 mm and about 100 mm, between about 1 mm and about 50 mm, between about 1 mm and about 20 mm, between about 1 mm and about 10 mm, or about 1 mm, about 2 mm, about 3 mm, about 4 mm about 5 mm, about 6 mm, about 7 mm, about 8 mm, about 9 mm, about 10 mm, or greater. The channel may have a length 424 between about 1 mm and about 100 mm, between about 10 mm and about 50 mm, between about 10 mm and about 20 mm, between about 1 mm and about 20 mm, or about 10 mm, about 11 mm, about 12 mm, about 13 mm, about 14 mm about 15 mm, about 16 mm, about 17 mm, about 18 mm, about 19 mm, about 20 mm, or greater. The shape of the channels may vary or may be constant along its length and/or width and may be substantially square, rectangular, oval, spherical, etc. in cross section. The diameter of the inlets may be between about 1 mm and about 10 mm, or about 1 mm, about 2 mm, about 3 mm, about 4 mm about 5 mm, about 6 mm, about 7 mm, about 8 mm, about 9 mm, about 10 mm, or greater.

Figure 17A:
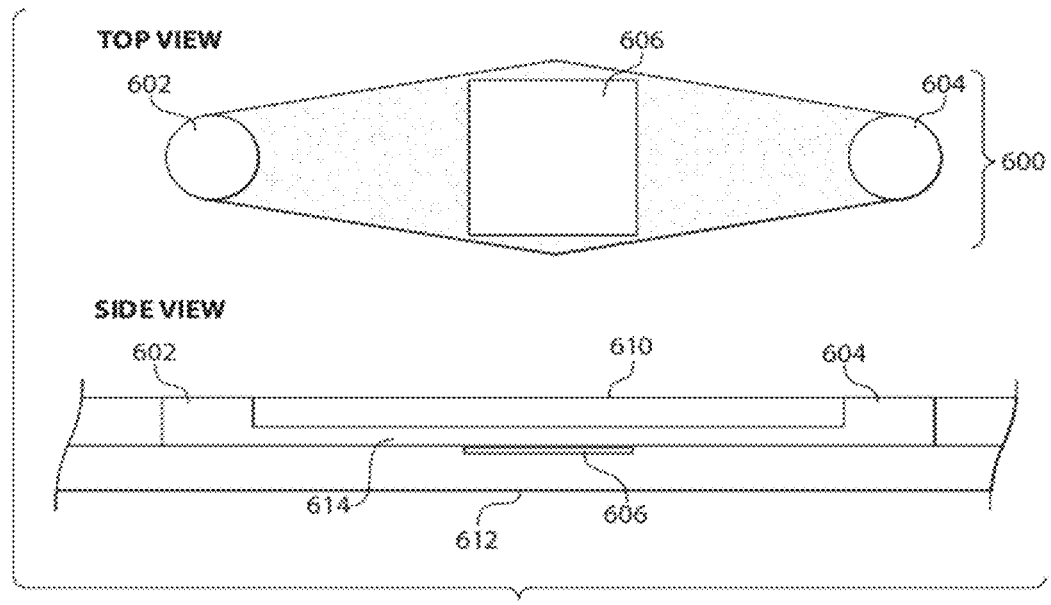
FIGS. 17A-17N are schematic diagrams showing non-limiting examples of assay consumable configurations.
Figure 17B:
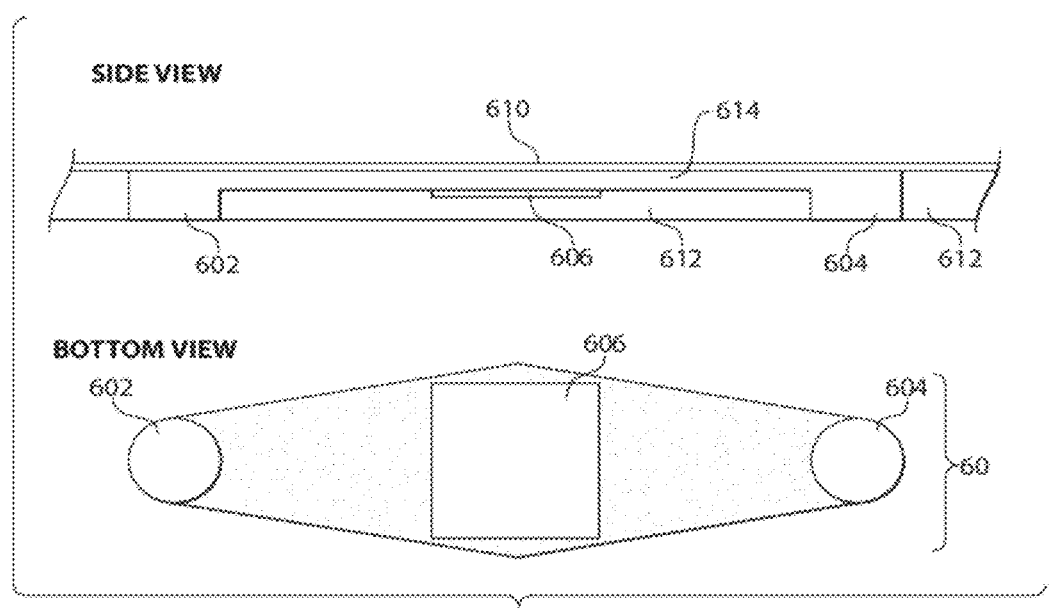
Figure 17C:
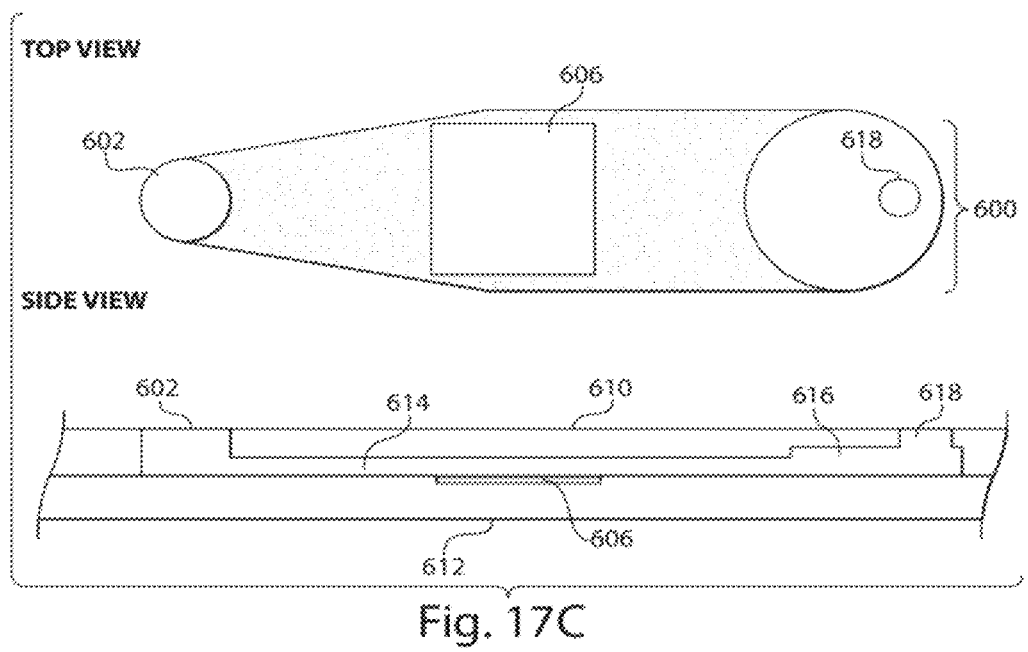
Figure 17D:
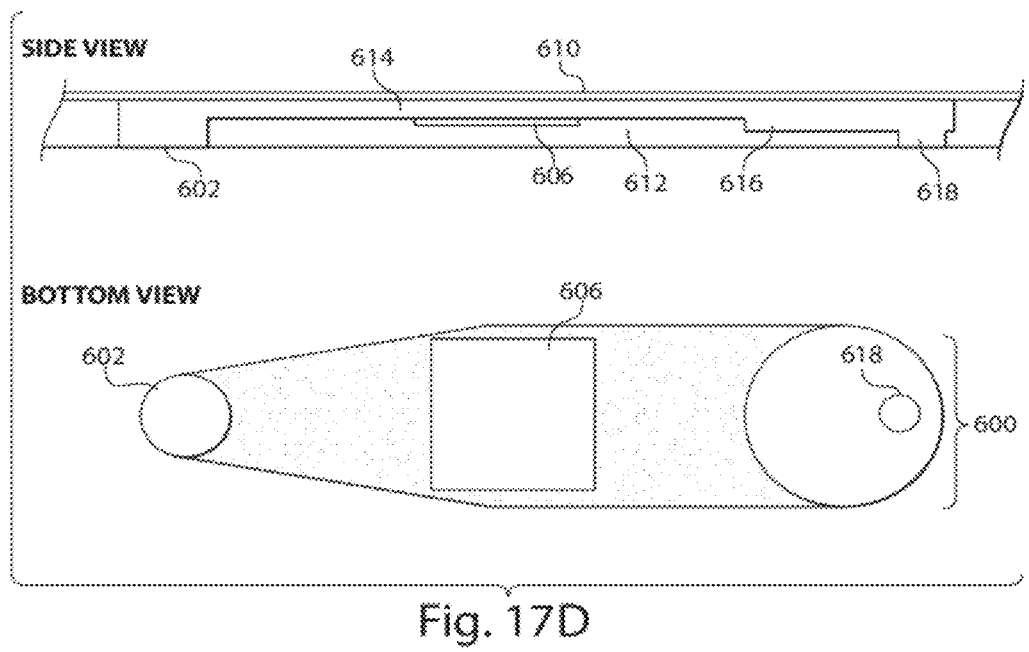
Figure 17E:
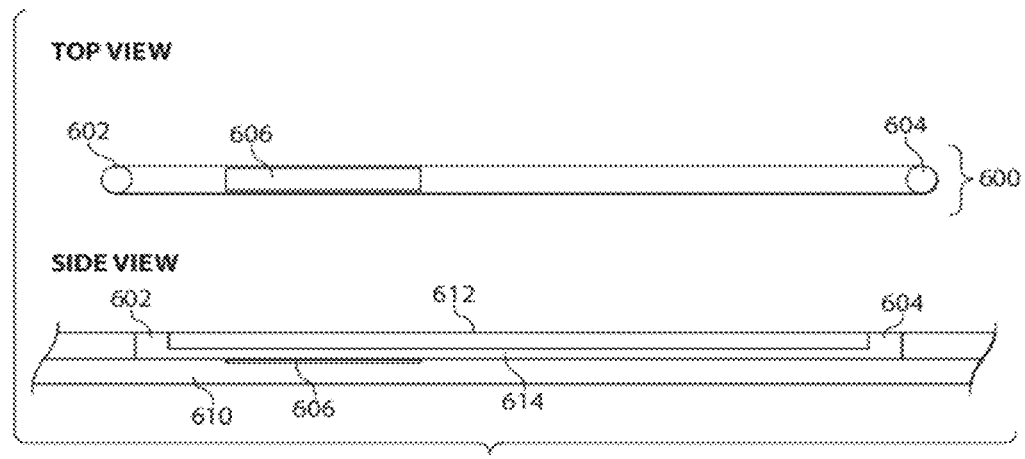
Figure 17F:
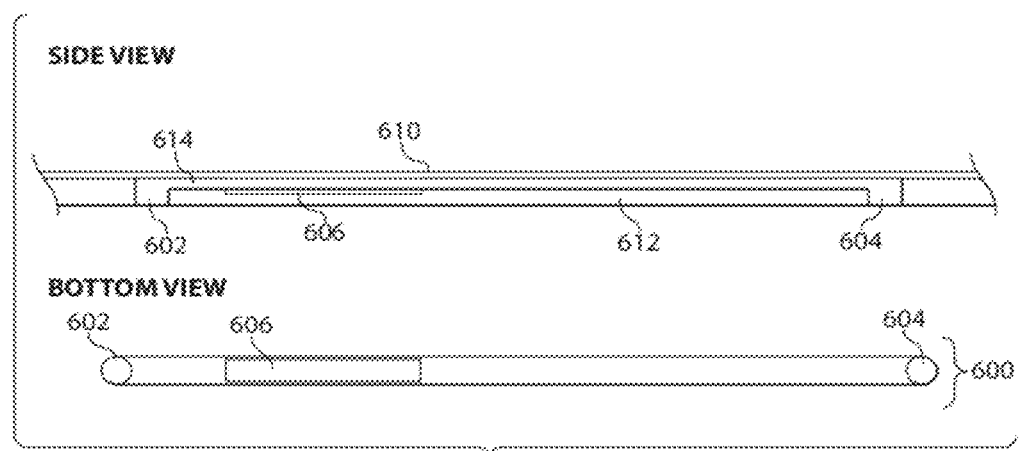
Figure 17G:
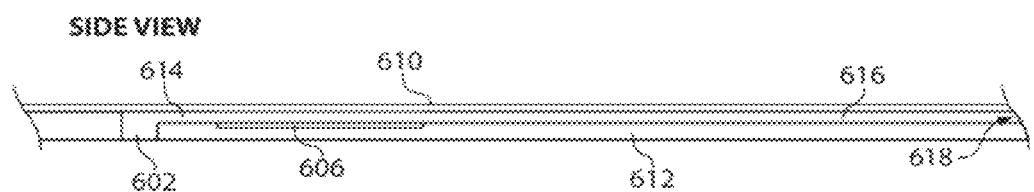
Figure 17H:
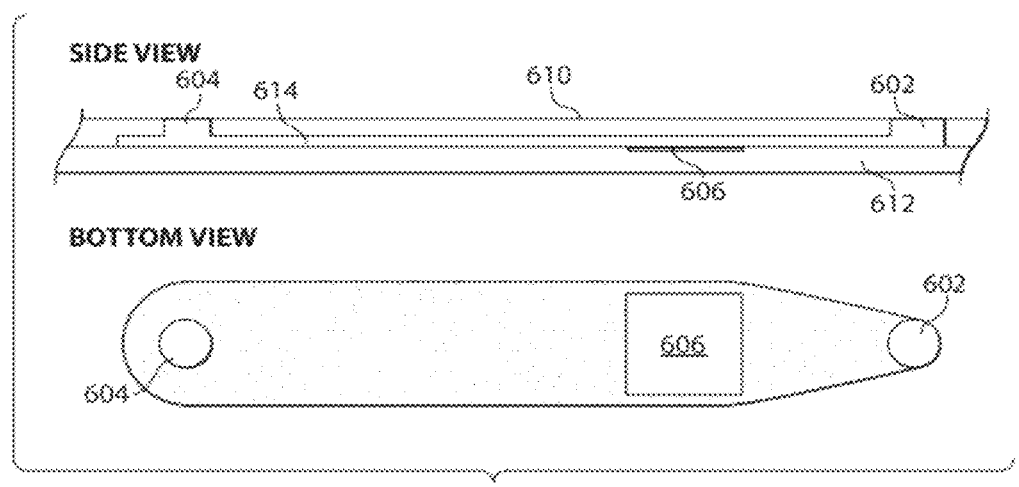
Figure 17I:
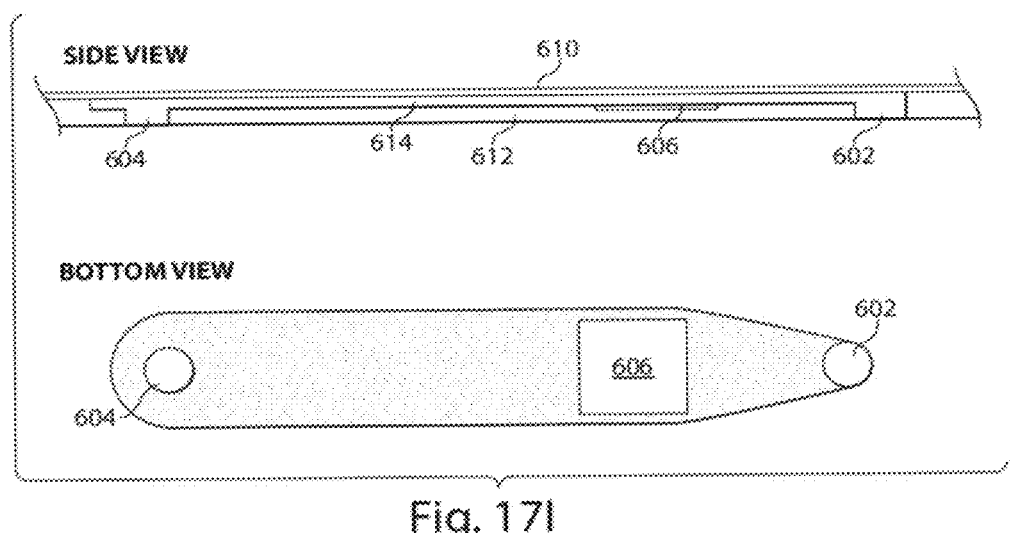
Figure 17J:
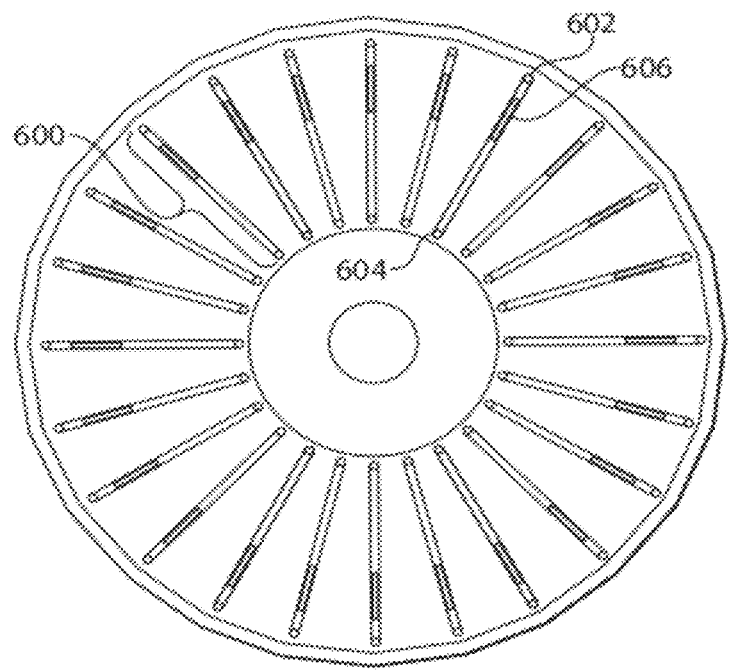
Figure 17K:
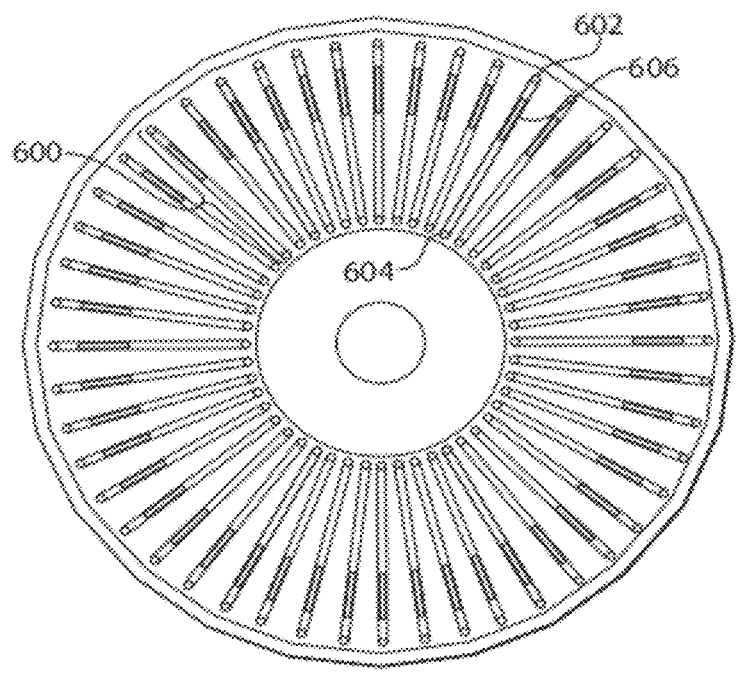
Figure 17L:
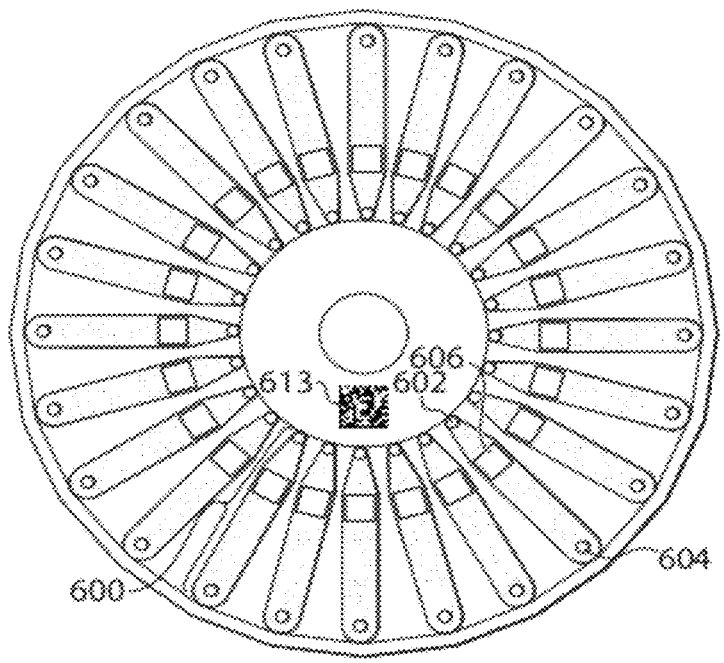
Figure 17M:
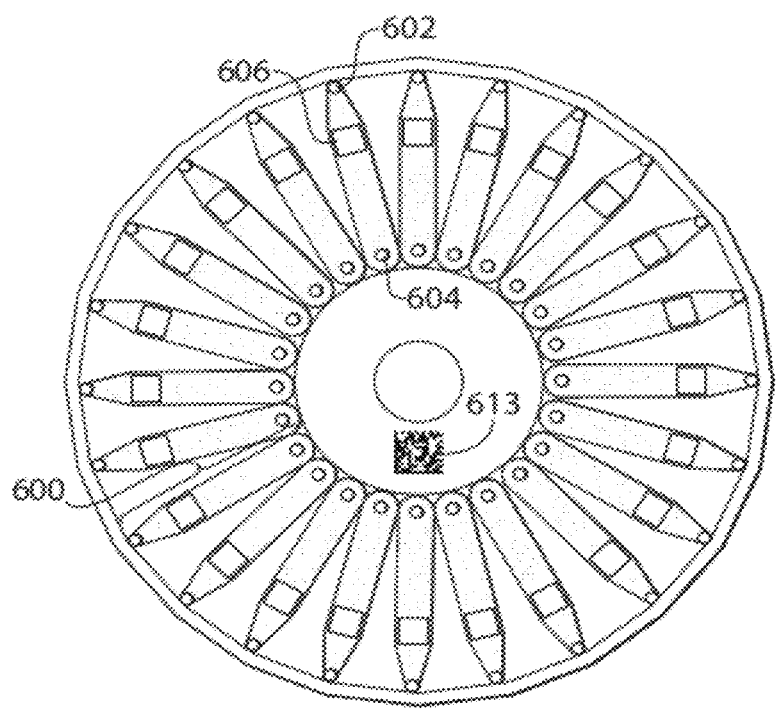
Figure 17N:
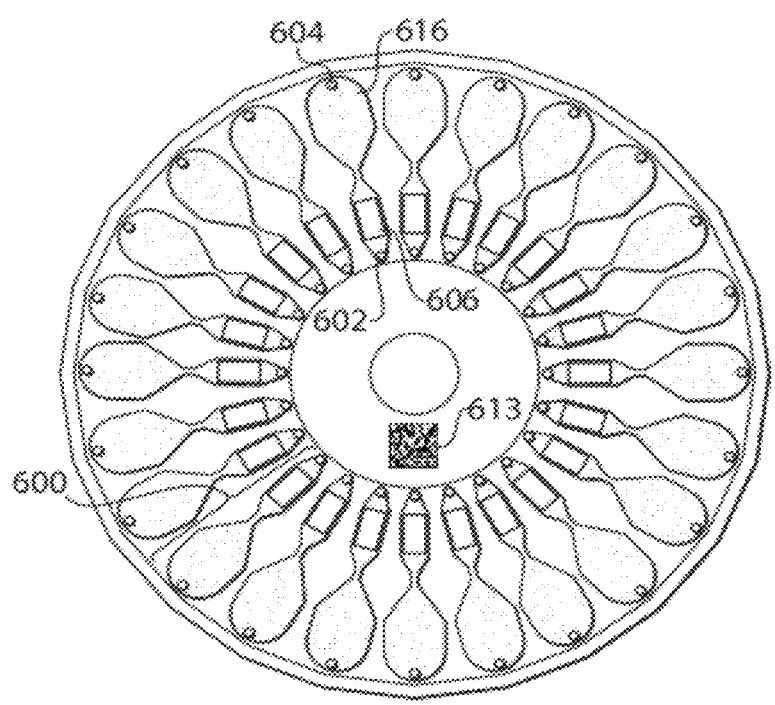

FIGS. 17A-17N illustrate embodiments of alternative arrangements of the assay consumable shown in FIG. 2B. For example, the chambers of assay consumables in various embodiments may vary with respect to one or more of the following features: the shape of the chamber, the location of assay sites in the chamber, the location, presence and/or absence of, and/or size of the inlet and/or outlet ports, the presence of a fluid reservoir, etc. For example, in FIG. 17A chamber 600 comprises an inlet 602, outlet 604, and plurality of assay sites in region 606. In this embodiment, as is shown in the side view, the plurality of assay sites 606 are formed in bottom material layer 612 and are contained in channel 614. Channel 614 is formed between bottom material layer 612 and top material layer 610, wherein inlet 602 and outlet 604 are also formed in top material layer 610.

FIG. 17B shows a similar arrangement as FIG. 17A, except inlet 602 and outlet 604 are formed in bottom surface layer 612. FIG. 17C shows another similar arrangement, except channel 614 comprises a fluid reservoir 616 which is designed as a reservoir for fluids used in an assay. In this figure, fluid reservoir 616 is associated with air vent 618 which allows for displacement of the air from fluid reservoir 616. The size of the fluid reservoir may be designed such that the fluid reservoir is capable of holding a required quantity of excess fluid based upon the specifics of an assay conducted using the assay consumable. FIG. 17D shows a similar arrangement as FIG. 17C, except inlet 602 and air vent 618 is formed in bottom surface layer 612. FIGS. 17E and 17F show similar arrangements as shown in FIGS. 17A and 17B respectively, except the shape and size of the chambers, channels, and assay site region are different. Similarly, FIGS. 17H and 17I show similar arrangements as shown in FIGS. 17A/17E and 17B/17F respectively, except the shape and size of the chambers, channels, and assay site region are different. FIG. 17G shows a similar arrangements as shown in FIG. 17E, except fluid reservoir 616 is differently configured.

FIGS. 17J-17N show disc shaped assay consumables having various distribution of chambers 600 thereon, similar to as the assay consumable shown in FIG. 17B. In particular, FIGS. 17J and 17K illustrate that a variable number of chambers may be present on the disc (e.g., FIG. 17J illustrates a disc with a fewer number of chambers as compared to FIG. 17K). FIGS. 17J/17K, 17L, 17M, and 17N illustrate the different shapes and sizes of chambers on a disc (e.g., FIGS. 17J/17K illustrate narrower chambers as compared to FIG. 17L or 17M), different locations of inlets and/or outlets (e.g., FIG. 17L illustrates inlet 602 closer to the center of the disc and FIG. 17M illustrates inlet 602 closer to the outer edge of the disc), and/or the presence of a fluid reservoir (e.g., see FIG. 17N).

The discs illustrated in FIGS. 17L-17N also comprise a computer readable identifier tag 613 thereon. Non-limiting examples of suitable identifier tags may bar codes or radio frequency identification (RFID) chips. The identifier tag may be used for a variety of purposes, such as to authentication and/or verification of identity, type, lot number, expiration date, etc. of the assay consumable and/or its contents. Verification can be achieved, for example, via an optical scanner or RFID proximity reader (depending on the type of identifier tag(s) employed) that provided in suitable locations on an assay consumable handler and/or imaging system for use with assay consumable 600. In certain embodiments, the information from an identifier can be stored for future reference and record-keeping purposes. Any suitable identifier such as a radio frequency identification (RFID) tag, a bar code, a serial number, a color tag, a fluorescent or optical tag (e.g., using quantum dots), chemical compounds, a radio tag, or a magnetic tag can be used. Detection of identifiers can be accomplished by a variety of methods known to those of ordinary skill in the art. The detection method depends in part on the particular identifier and can include, for example, imaging, fluorescence detection, spectroscopy, microscopy, etc. In one embodiment, a RFID tag is used as an identifier. The RFID tag can include an integrated circuit (e.g., for storing and processing information, modulating and demodulating a radio frequency (RF) signal) and an antenna for receiving and transmitting the signal. The RFID tag may be passive, semi-passive (e.g., battery-assisted), or active. It should be understood that RFID tags are known in the art and that any suitable RFID tag can be incorporated into components of an assay consumable described herein.

Figure 2C:
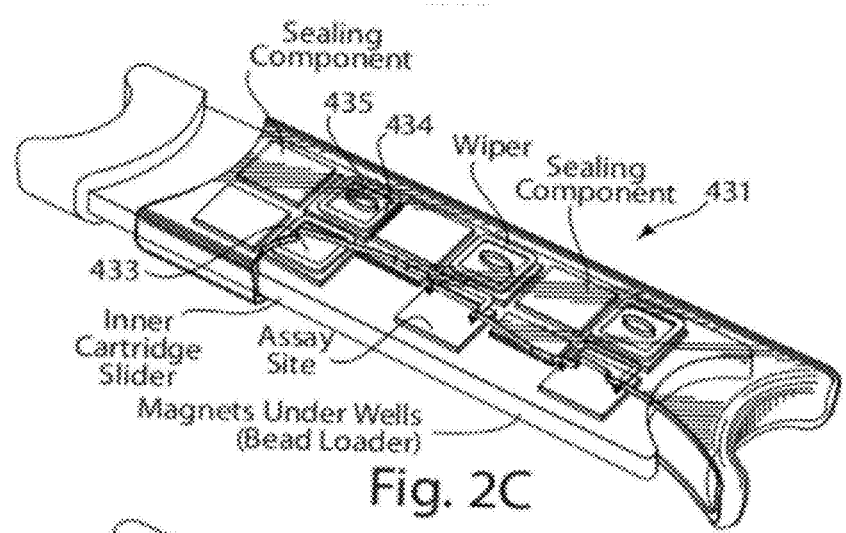
Figure 2D:
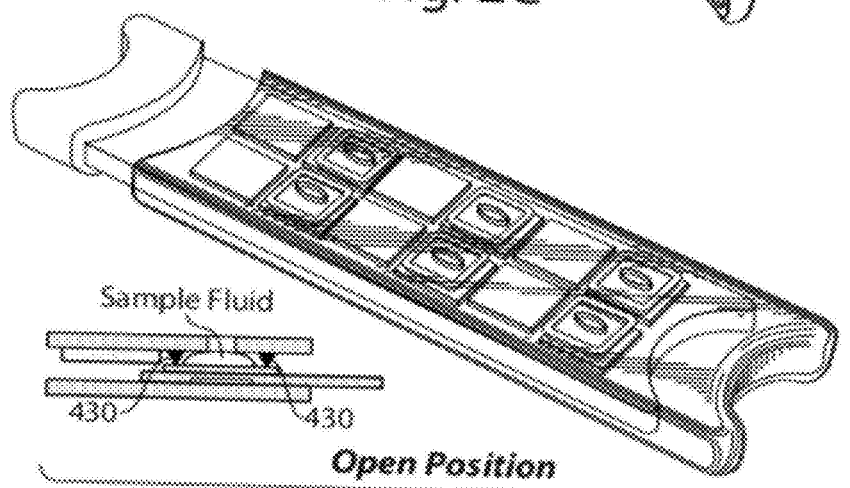
Figure 2E:
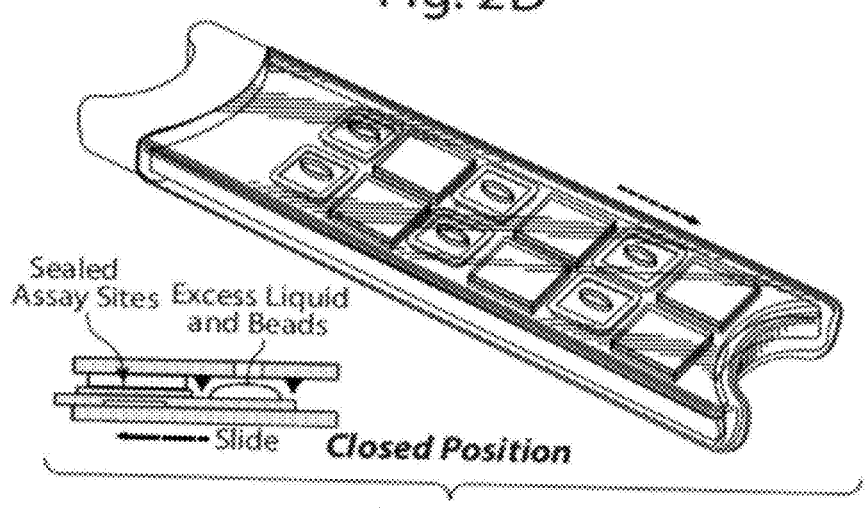

FIG. 2C shows yet another non-limiting example of an assay consumable. In this figure, assay consumable 431 comprises a plurality of spatially separated chambers which are fluidically isolatable from the other spatially separated chambers. A group of assay sites is located in each spatially separated chamber 434, which comprises a channel having first opening 433 and second opening 435. Various fluids and other component may be provided through the openings. In this embodiment, the lid is configured to slide onto the body of the assay component. In addition, the lid carries sealing component(s) that move relative to the spatially separated chambers upon moving the lid between an open position (e.g., as shown in FIG. 2D) and a closed position (e.g., as shown in FIG. 2E). In the open position, there is at least one opening to access each of the fluidically isolated chambers, while with the lid in the closed position, the sealing components fluidically seal the chambers. In this example, each fluidically isolated chamber also comprises at least one wiper 430, wherein the wiper is constructed and positioned so that upon movement of the lid an open to a closed position, each wiper moves in sliding contact with the surface comprising a plurality of assay sites contained in each of the spatially separated chambers (e.g., thereby removing any beads present on the surface of the assay consumable comprising a plurality of reaction vessels and not substantially contained in an assay site).

Figure 2F:
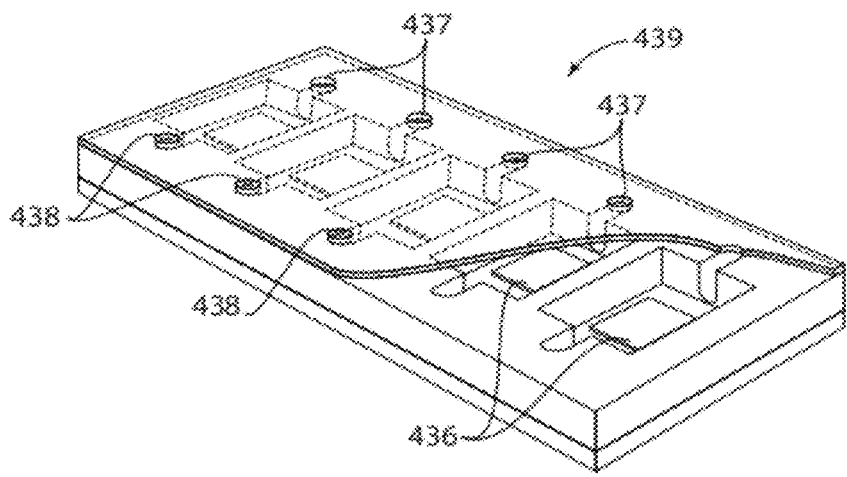
Figure 2G:
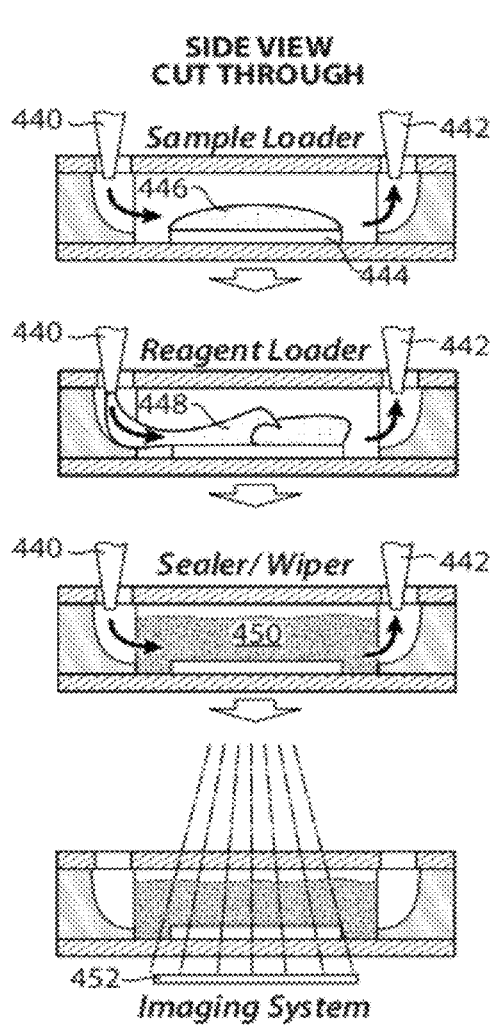
Figure 2H:
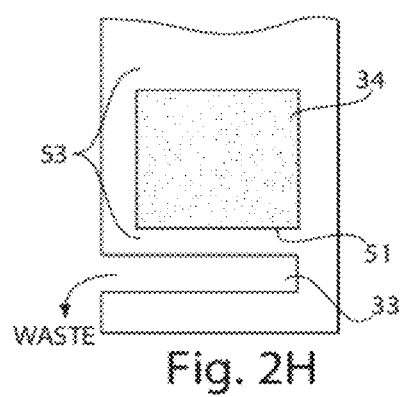
FIGS. 2H-2K are schematic diagrams showing non-limiting examples of assay consumable configuration comprising channels and/or moat surrounding the assay sites.
Figure 2I:
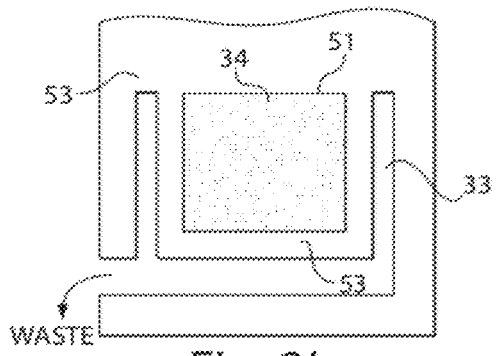
Figure 2J:
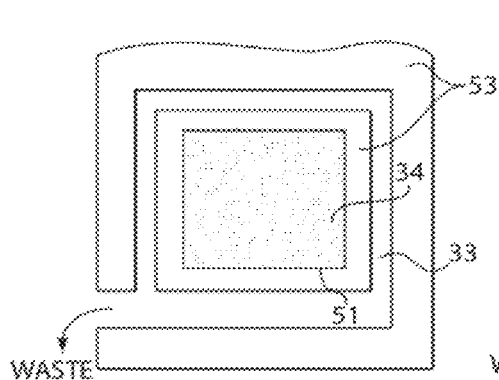
Figure 2K:
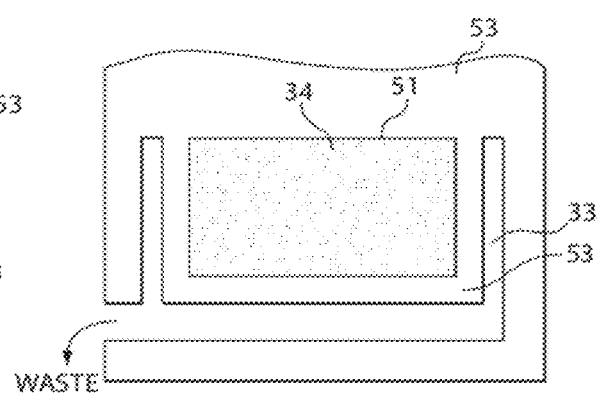

Yet another exemplary embodiment is shown in FIG. 2F. In this figure, assay consumable 439 comprises a plurality of spatially separated chambers 436 which are fluidically isolated from the other spatially separated chambers. A group of assay sites 444 is located in each spatially separated chamber 436, which comprises a channel having first opening 437 and second opening 438. FIG. 2G depicts function of the channel, including use of a sample loader, a reagent loader, a sealer/wiper, and an imaging system. The use and function of the channel may be similar to t that of the embodiment in FIGS. 8A-8G. In FIG. 2G, inlet tip 440, outlet tip 442, comprise at least a portion of the sample loader, reagent loader, sealer and wiper of the illustrated by sequentially injecting at different times during the course of an assay sample fluid 446 (left), reagent fluid 448 (second from left), and an sealing/wiping fluid 450 (second from right) over assay sites 444, and then interrogating the assay sites with imaging system 452 (right).

In some embodiments, systems employing an assay consumable comprising a fluid channel (e.g., comprising a plurality of assay sites) may include an air bubble detector system configured to determine the presence and/or absence of air in fluid channel(s) of the assay consumable (e.g., an air bubble in the channel above the plurality of assay sites). It may be important to detect the presence of an air bubble as an air bubble positioned above the plurality of assay sites may affect the ability to determine and accurate signal from all or a portion of the assay sites, and thus may, for example, skew or alter the results of the determination of a concentration an analyte molecule or particle in an assay sample.

For example, if the imaging system is configured to process a signal accounting for the presence of a certain thickness of fluid above the assay sites, the presence of air may alter the signal such that determination of the signal provides incorrect and/or inaccurate results. Those of ordinary skill in the art will be aware of suitable methods and systems for determining the presence of an air bubble in a channel.

Figure 18:
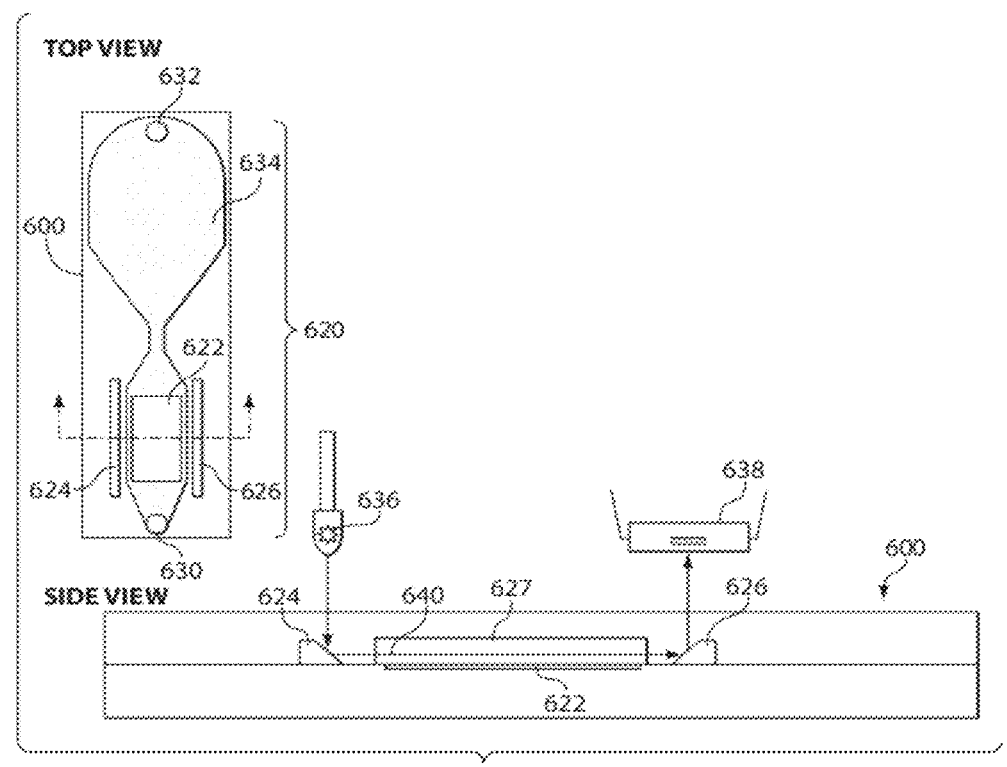
FIG. 18 is a schematic diagram of a system for determining the presence or absence of an air bubble in a fluid channel of an assay consumable.

FIG. 18 depicts a non-limiting example of an air bubble detector system. Chamber 620 of an assay consumable comprises inlet 630, fluid reservoir 634, air vent 632, and an array 622 of assay sites contained in channel 627. Air bubble detector system comprises first reflector 624 and second reflector 626 on assay consumable 600, that interacts with a light source 636 (e.g., LED) and detector 638 of the assay system. Light emitted by light source 636 is reflected by first reflector 624 such that light (e.g., as indicated by line 640) passes through channel 622 above the array 622 of assay sites and impinges upon second reflector 626, which redirects it to a detector 638. The presence of an air bubble in channel 627 may be determined based on the signal detected by detector 638. For example, the presence of an air bubble in channel 627 may reduce the intensity and/or quantity of the light transmitted from light source 636 to detector 638.

Exemplary Beads

As described above, certain of the systems provided by the invention are particularly suited for assays using beads for analyte capture (e.g., systems including bead loaders and/or wipers). Beads which may be used for analyte capture may be of any suitable size or shape. Non-limiting examples of suitable shapes include spheres (i.e. essentially spherical), cubes (i.e. essentially cubic), ellipsoids (i.e. essentially ellipsoidal), tubes, sheets, irregular shapes, etc. In certain embodiments, the average diameter (if substantially spherical) or average maximum cross-sectional dimension (for other shapes) of a bead may be greater than about 0.1 um (micrometer), greater than about 1 um, greater than about 10 um, greater than about 100 um, greater than about 1 mm, or the like. In other embodiments, the average diameter of a bead or the maximum dimension of a bead in one dimension may be between about 0.1 um and about 100 um, between about 1 um and about 100 um, between about 10 um and about 100 um, between about 0.1 um and about 1 mm, between about 1 um and about 10 mm, between about 0.1 um and about 10 um, or the like. The "average diameter" or "average maximum cross-sectional dimension" of a plurality of beads, as used herein, is the arithmetic average of the diameters/maximum cross-sectional dimensions of the beads. Those of ordinary skill in the art will be able to determine the average diameter/maximum cross-sectional dimension of a population of bead, for example, using laser light scattering, microscopy, sieve analysis, or other known techniques. For example, in some cases, a Coulter counter may be used to determine the average diameter of a plurality of beads.

The beads used for analyte capture may be fabricated from one or more suitable materials, for example, plastics or synthetic polymers (e.g., polyethylene, polypropylene, polystyrene, polyamide, polyurethane, phenolic polymers, or nitrocellulose etc.), naturally derived polymers (latex rubber, polysaccharides, polypeptides, etc), composite materials, ceramics, silica or silica-based materials, carbon, metals or metal compounds (e.g., comprising gold, silver, steel, aluminum, copper, etc.), inorganic glasses, silica, and a variety of other suitable materials.

In some embodiments, more than one type of bead for analyte capture may be employed. In some cases, each type of bead may include a surface with differing binding specificity. In addition, each type of bead may have a unique optical (or other detectable) signal, such that each type of bead is distinguishable for each of the other types of beads, for example to facilitate multiplexed assays. In these embodiments, more than one type of analyte molecule may be quantified and/or detected in a single, multiplexed assay method. Of course, as discussed previously, in certain embodiments, the beads are magnetic beads.

Exemplary Methods

The systems and devices of the invention may be employed for use in practicing a wide variety of methods, such as assay methods, as would be apparent to those skilled in the art. In some cases, use of the inventive systems or other systems permit the methods of the invention to be automated. That is, the methods may be conducted using systems which are configured to carry out the steps (or at least one step) with little or no human intervention once the method has begun.

In some embodiments, the present invention provides an automated method for forming a plurality of sealed assay sites which can be used for performing an assay. In some cases, the method comprises the steps of operatively associating an assay consumable having a surface comprising a plurality of assay sites with a sealer apparatus comprising a sealer (e.g., as described above) and a controller (e.g., configured to operate the sealer automatically) and applying a sealing component (e.g., as described herein and including, but not limited to, a sealing fluid, a pressure-adhesive layer, a film, etc.) to the plurality of assay sites with the sealer apparatus. Following application of the sealing component, a plurality of sealed assay sites may be formed, wherein the contents of each sealed assay site is substantially isolated from the contents of each of the other plurality of sealed assay sites. In some cases, a plurality of beads is provided to the plurality of assay sites such that at least some of the assay sites contain at least one bead. The beads may be provide and/or contained in the assay sites using a bead loader (e.g., as described herein). The beads may or may not be associated with an analyte molecule or particle. In some cases, substantially all of the beads which are on the surface of the assay consumable containing the plurality of assay sites which are not substantially contained in an assay site may be removed (e.g., using a wiper, as described herein).

In another embodiment, a method for inserting beads into reaction vessels on an assay consumable is provided. The method may comprise generating a magnetic field in proximity to a surface of the assay consumable comprising a plurality of the reaction, wherein the magnetic field vector of the magnetic field is directed from the surface towards a bottom of the reaction vessels and/or towards the perimeter of the surface. A plurality of magnetic beads may be delivered proximate the surface. The beads may be inserted into the reaction vessels by causing relative motion between the magnetic beads and the reaction vessels (e.g., using a bead loader, as described herein). Creation of relative motion is described herein and may be caused by moving a magnetic field relative to the surface of the assay consumable containing the plurality of assay sites or moving the assay consumable relative to the magnetic field, by causing motion of a fluid substantially surrounding the beads, or the like. In some cases, following the creating step, a first portion of the magnetic beads are contained in the reaction vessels and a second portion of the magnetic beads are positioned on the surface of the assay consumable, but not contained within an reaction vessel. The second portion of beads may be removed (e.g., using a wiper, as described herein).

In yet another embodiment, a method for forming a plurality of sealed reaction vessels for performing an assay is provided. The method may first comprise associating an assay consumable having a surface comprising a plurality of assay sites with a sealing component (e.g., liquid, film, etc.) by applying the sealing component to the surface (e.g., using a sealer, as described herein). Upon application of the sealing component, the contents of each assay site may be substantially isolated from the contents of each of the other plurality of assay sites without maintaining any pressure applied to the sealing component.

In still yet another embodiment, a method for forming a plurality of sealed reaction vessels for performing an assay is provided. Initially, an assay consumable having a surface comprising a plurality of assay sites may be associated with a sealing component by applying the sealing component to the surface of the assay consumable and applying pressure to the sealing component. Following application of the sealing component, the contents of each assay site may be substantially isolated from the contents of each of the other plurality of assay sites. In this method, the sealing component comprises a pressure-sensitive adhesive wherein the pressure-sensitive adhesive is activated upon application of the pressure to the sealing component and the adhesive forms an adhesive bond between the sealing component and the surface of the assay consumable.

Certain methods of the present invention may be useful for characterizing analyte molecules (or particles) in a sample. In some cases, the methods and/or systems may be useful for detecting and/or quantifying analyte molecules in a fluid sample which is suspected of containing at least one type of analyte molecule. In some cases, the methods and/or system may be designed such that the number (or equivalently fraction) of interrogated assay sites (e.g., reaction vessels) which contain an analyte molecule or an analyte molecule associated with a bead can be correlated to the concentration of analyte molecules in the fluid sample. Certain embodiments thus can provide a measure of the concentration of analyte molecules in a fluid sample based at least in part on the number or fraction of assay sites which contain an analyte molecule (or analyte molecule associated with a capture component). In embodiments where beads are employed, this number/fraction may be related to the total number of assay sites comprising a bead (e.g., with or without an associated analyte molecule or labeling agent) and/or to the total number of assay sites interrogated.

In certain embodiments, a method for detection and/or quantifying analyte molecules (or particles) in a sample fluid comprises immobilizing a plurality of analyte molecules with respect to a plurality of beads that each include a binding surface having affinity for at least one type of analyte molecule (or particle) is performed by the systems described herein. For example, the beads may comprise a plurality of capture components (e.g., an antibody having specific affinity for an analyte molecule of interest, etc.). At least some of the beads (e.g., at least some associated with at least one analyte molecule) may be spatially separated/segregated into a plurality of assay sites (e.g., on an assay consumable), and at least some of the assay sites may be addressed/interrogated (e.g., using an imaging system). A measure of the concentration of analyte molecules in the sample fluid may be determined based on the information received when addressing the assay sites (e.g., using the information received from the imaging system and/or processed using a computer implemented control system). In some cases, a measure of the concentration of analyte molecules in the sample fluid may be based at least in part on the number of assay sites determined to contain a bead that is or was associated with at least one analyte molecule. In other cases and/or under differing conditions, a measure of the concentration may be based at least in part on an intensity level of at least one signal indicative of the presence of a plurality of analyte molecules and/or beads associated with an analyte molecule at one or more of the assay sites.

In embodiments where beads are employed, the partitioning of the beads can be performed, for example in certain embodiments by the sample loader and/or bead loader, such that at least some (e.g., a statistically significant fraction) of the assay sites comprise at least one or, in certain cases, only one bead associated with at least one analyte molecule and at least some (e.g., a statistically significant fraction) of the assay sites comprise a bead not associated with any analyte molecules. The beads associated with at least one analyte molecule may be quantified in certain embodiments, thereby allowing for the detection and/or quantification of analyte molecules in the sample fluid using techniques known to those of ordinary skill in the art.

An exemplary assay method is as follows. A sample fluid containing or suspected of containing analyte molecules or particles are provided. An assay consumable comprising a plurality of assay sites is exposed to the sample fluid. In some cases, the analyte molecules are provided in a manner (e.g., at a concentration) such that a statistically significant fraction of the assay sites contain a single analyte molecule and a statistically significant fraction of the assay sites do not contain any analyte molecules (e.g., using a sample loader). The assay sites may optionally be exposed to a variety of reagents (e.g., using a reagent loader) and or rinsed (e.g., using a rinser). The assay sites are then sealed (e.g., using a sealer) and imaged (e.g., using an imaging system). The images are then analyzed (e.g., by the computer implemented control system) such that a measure of the concentration of the analyte molecules in the fluid sample may be obtained, based at least in part, by determination of the number of assay sites which contain an analyte molecule and/or the number of sites which do not contain any analyte molecules. In some cases, the analyte molecules are provided in a manner (e.g., at a concentration) such that at least some assay sites comprise more than one analyte molecule. In such embodiments, a measure of the concentration of analyte molecules or particles in the fluid sample may be obtained at least in part on an intensity level of at least one signal indicative of the presence of a plurality of analyte molecules at one or more of the assay sites In some cases, the methods optionally comprise exposing the fluid sample to a plurality of beads. At least some of the analyte molecules are immobilized with respect to a bead. In some cases, the analyte molecules are provided in a manner (e.g., at a concentration) such that a statistically significant fraction of the beads associate with a single analyte molecule and a statistically significant fraction of the beads do not associate with any analyte molecules. At least some of the plurality of beads (e.g., those associated with a single analyte molecule or not associated with any analyte molecules) may then be spatially separated/segregated into a plurality of assay sites of the assay consumable. The assay sites may optionally be exposed to a variety of reagents (e.g., using a reagent loader) and or rinsed (e.g., using a rinser). At least some of the assay sites may then be addressed (e.g., using an imaging system) to determine the number of assay sites containing an analyte molecule. In some cases, the number of assay sites containing a bead not associated with an analyte molecule, the number of assay sites not containing a bead and/or the total number of assay sites addressed may also be determined. Such determination(s) may then be used to determine a measure of the concentration of analyte molecules in the fluid sample. In some cases, more than one analyte molecule may associate with a bead and/or more than one bead may be present in an assay site.

In some embodiments, the analyte molecules (e.g., optionally associated with a bead) may be exposed to at least one reagent. In some cases, the reagent may comprise a plurality of binding ligands which have an affinity for at least one type of analyte molecule (or particle). A "binding ligand," is any molecule, particle, or the like which specifically binds to or otherwise specifically associates with an analyte molecule to aid in the detection of the analyte molecule. Certain binding ligands can comprise an entity that is able to facilitate detection, either directly (e.g., via a detectable moiety) or indirectly. A component of a binding ligand may be adapted to be directly detected in embodiments where the component comprises a measurable property (e.g., a fluorescence emission, a color, etc.). A component of a binding ligand may facilitate indirect detection, for example, by converting a precursor labeling agent into a labeling agent (e.g., an agent that is detected in an assay). Accordingly, another exemplary reagent is a precursor labeling agent. A "precursor labeling agent" is any molecule, particle, or the like, that can be converted to a labeling agent upon exposure to a suitable converting agent (e.g., an enzymatic component). A "labeling agent" is any molecule, particle, or the like, that facilitates detection, by acting as the detected entity, using a chosen detection technique. In some embodiments, the binding ligand may comprise an enzymatic component (e.g., horseradish peroxidase, beta-galactosidase, alkaline phosphatase, etc). A first type of binding ligand may or may not be used in conjunction with additional binding ligands (e.g., second type, etc.).

Those of ordinary skill in the art will be aware of additional components and information relating to methods of quantifying analyte molecules in a sample fluid, for example, those described in U.S. Patent Application Publication No. US-2007-0259448 (Ser. No. 11/707,385), filed Feb. 16, 2007, entitled "METHODS AND ARRAYS FOR TARGET ANALYTE DETECTION AND DETERMINATION OF TARGET ANALYTE CONCENTRATION IN SOLUTION," by Walt et al.; U.S. Patent Application Publication No. US-2007-0259385 (Ser. No. 11/707,383), filed Feb. 16, 2007, entitled "METHODS AND ARRAYS FOR DETECTING CELLS AND CELLULAR COMPONENTS IN SMALL DEFINED VOLUMES," by Walt et al.; U.S. Patent Application Publication No. US-2007-0259381 (Ser. No. 11/707,384), filed Feb. 16, 2007, entitled "METHODS AND ARRAYS FOR TARGET ANALYTE DETECTION AND DETERMINATION OF REACTION COMPONENTS THAT AFFECT A REACTION," by Walt et al.; International Patent Application No. PCT/US2007/019184, filed Aug. 30, 2007, entitled "METHODS OF DETERMINING THE CONCENTRATION OF AN ANALYTE IN SOLUTION," by Walt et al.; U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE," by Duffy et al.; U.S. Patent Application Publication No. US-2010-00754072 (Ser. No. 12/236,486), filed Sep. 23, 2008, entitled "ULTRA-SENSITIVE DETECTION OF MOLECULES ON SINGLE MOLECULE ARRAYS," by Duffy et al., U.S. Patent Application Publication No. US-2010-0075439 (Ser. No. 12/236,488), filed Sep. 23, 2008, entitled "ULTRA-SENSITIVE DETECTION OF MOLECULES BY CAPTURE-AND-RELEASE USING REDUCING AGENTS FOLLOWED BY QUANTIFICATION," by Duffy et al.; U.S. Patent Application Publication No. US-2010-0075355 (Ser. No. 12/236,490), filed Sep. 23, 2008, entitled "ULTRA-SENSITIVE DETECTION OF ENZYMES BY CAPTURE-AND-RELEASE FOLLOWED BY QUANTIFICATION," by Duffy et al.; U.S. patent application Ser. No. 12/731,130, filed Mar. 24, 2010, entitled "ULTRA-SENSITIVE DETECTION OF MOLECULES OR PARTICLES USING BEADS OR OTHER CAPTURE OBJECTS," by Duffy et al.; U.S. patent application Ser. No. 12/731,135, filed Mar. 24, 2010, entitled "ULTRA-SENSITIVE DETECTION OF MOLECULES USING DUAL DETECTION METHODS," by Duffy et al.; and U.S. patent application Ser. No. 12/731,136, filed Mar. 24, 2010, entitled "METHODS AND SYSTEMS FOR EXTENDING DYNAMIC RANGE IN ASSAYS FOR THE DETECTION OF MOLECULES OR PARTICLES," by Duffy et al.; each herein incorporated by reference.

Computer Implemented Control Systems

As described above, certain embodiments of the inventive systems include one or more controllers/computer implemented control systems for operating various components/subsystems of the system, performing data/image analysis, etc. (e.g., controller 2/computer implemented control system 12 shown in FIG. 1, controller 24/computer implemented control system 32 shown in FIG. 3A, and controller 92/computer implemented control system 88 shown in FIG. 6A). In general, any calculation methods, steps, simulations, algorithms, systems, and system elements described herein may be implemented and/or controlled using one or more computer implemented control system(s), such as the various embodiments of computer implemented systems described below. The methods, steps, control systems, and control system elements described herein are not limited in their implementation to any specific computer system described herein, as many other different machines may be used.

The computer implemented control system(s) can be part of or coupled in operative association with an image analysis system and/or other automated system components, and, in some embodiments, is configured and/or programmed to control and adjust operational parameters, as well as analyze and calculate values, for example analyte molecule or particle concentrations as described above. In some embodiments, the computer implemented control system(s) can send and receive reference signals to set and/or control operating parameters of system apparatus. In other embodiments, the computer implemented system(s) can be separate from and/or remotely located with respect to the other system components and may be configured to receive data from one or more remote assay systems of the invention via indirect and/or portable means, such as via portable electronic data storage devices, such as magnetic disks, or via communication over a computer network, such as the Internet or a local intranet.

The computer implemented control system(s) may include several known components and circuitry, including a processing unit (i.e., processor), a memory system, input and output devices and interfaces (e.g., an interconnection mechanism), as well as other components, such as transport circuitry (e.g., one or more busses), a video and audio data input/output (I/O) subsystem, special-purpose hardware, as well as other components and circuitry, as described below in more detail. Further, the computer system(s) may be a multi-processor computer system or may include multiple computers connected over a computer network.

The computer implemented control system(s) may include a processor, for example, a commercially available processor such as one of the series x86, Celeron and Pentium processors, available from Intel, similar devices from AMD and Cyrix, the 680X0 series microprocessors available from Motorola, and the PowerPC microprocessor from IBM. Many other processors are available, and the computer system is not limited to a particular processor.

A processor typically executes a program called an operating system, of which WindowsNT, Windows95 or 98, Windows XP, Windows Vista, Windows 7, UNIX, Linux, DOS, VMS, MacOS and OS8 are examples, which controls the execution of other computer programs and provides scheduling, debugging, input/output control, accounting, compilation, storage assignment, data management and memory management, communication control and related services. The processor and operating system together define a computer platform for which application programs in high-level programming languages are written. The computer implemented control system is not limited to a particular computer platform.

The computer implemented control system(s) may include a memory system, which typically includes a computer readable and writeable non-volatile recording medium, of which a magnetic disk, optical disk, a flash memory and tape are examples. Such a recording medium may be removable, for example, a floppy disk, read/write CD or memory stick, or may be permanent, for example, a hard drive.

Such a recording medium stores signals, typically in binary form (i.e., a form interpreted as a sequence of one and zeros). A disk (e.g., magnetic or optical) has a number of tracks, on which such signals may be stored, typically in binary form, i.e., a form interpreted as a sequence of ones and zeros. Such signals may define a software program, e.g., an application program, to be executed by the microprocessor, or information to be processed by the application program.

The memory system of the computer implemented control system(s) also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the computer implemented control system(s) that implements the methods, steps, systems control and system elements control described above is not limited thereto. The computer implemented control system(s) is not limited to a particular memory system.

At least part of such a memory system described above may be used to store one or more data structures (e.g., look-up tables) or equations such as calibration curve equations. For example, at least part of the non-volatile recording medium may store at least part of a database that includes one or more of such data structures. Such a database may be any of a variety of types of databases, for example, a file system including one or more flat-file data structures where data is organized into data units separated by delimiters, a relational database where data is organized into data units stored in tables, an object-oriented database where data is organized into data units stored as objects, another type of database, or any combination thereof.

The computer implemented control system(s) may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The computer implemented control system(s) may include one or more output devices. Example output devices include a cathode ray tube (CRT) display, liquid crystal displays (LCD) and other video output devices, printers, communication devices such as a modem or network interface, storage devices such as disk or tape, and audio output devices such as a speaker.

The computer implemented control system(s) also may include one or more input devices. Example input devices include a keyboard, keypad, track ball, mouse, pen and tablet, communication devices such as described above, and data input devices such as audio and video capture devices and sensors. The computer implemented control system(s) is not limited to the particular input or output devices described herein.

It should be appreciated that one or more of any type of computer implemented control system may be used to implement various embodiments described herein. Aspects of the invention may be implemented in software, hardware or firmware, or any combination thereof. The computer implemented control system(s) may include specially programmed, special purpose hardware, for example, an application-specific integrated circuit (ASIC). Such special-purpose hardware may be configured to implement one or more of the methods, steps, simulations, algorithms, systems control, and system elements control described above as part of the computer implemented control system(s) described above or as an independent component.

The computer implemented control system(s) and components thereof may be programmable using any of a variety of one or more suitable computer programming languages. Such languages may include procedural programming languages, for example, LabView, C, Pascal, Fortran and BASIC, object-oriented languages, for example, C++, Java and Eiffel and other languages, such as a scripting language or even assembly language.

The methods, steps, simulations, algorithms, systems control, and system elements control may be implemented using any of a variety of suitable programming languages, including procedural programming languages, object-oriented programming languages, other languages and combinations thereof, which may be executed by such a computer system. Such methods, steps, simulations, algorithms, systems control, and system elements control can be implemented as separate modules of a computer program, or can be implemented individually as separate computer programs. Such modules and programs can be executed on separate computers.

Such methods, steps, simulations, algorithms, systems control, and system elements control, either individually or in combination, may be implemented as a computer program product tangibly embodied as computer-readable signals on a computer-readable medium, for example, a non-volatile recording medium, an integrated circuit memory element, or a combination thereof. For each such method, step, simulation, algorithm, system control, or system element control, such a computer program product may comprise computer-readable signals tangibly embodied on the computer-readable medium that define instructions, for example, as part of one or more programs, that, as a result of being executed by a computer, instruct the computer to perform the method, step, simulation, algorithm, system control, or system element control.

These and other aspects of the present invention will be further appreciated upon consideration of the following Examples, which are intended to illustrate certain particular embodiments of the invention but are not intended to limit its scope, as defined by the claims.

Example 1

The following example describes quantitative measurement of enzyme molecules in an array consumable sealed with an elastomeric film using a sealer comprising a roller configuration The assay consumable used in this example was obtained from Edge Embossing (Medford, Mass.) and was a COC chip wherein the wells were made using self-embossing techniques. The assay consumable comprised an array of five hundred thousand 50-femtoliter wells. The array consumable was placed on as array consumable handler. 10 µl of an enzyme (SβG) at 8 pM were mixed with 10 µl aqueous fluorogenic substrate (RGP) on top of the array of wells, resulting in a final enzyme concentration of 4 pM. The mixture was allowed to fill the array of wells. An elastomeric film, namely a PDMS gasket, was placed on the surface of the array consumable. The sealer moved a roller assembly laterally across PDMS gasket in contact with the array consumable surface to seal the array of wells. During the sealing process, the excess fluid that was not contained within the wells was pushed to the side by the elastomeric film. Five fluorescence images (at 30-second intervals) were acquired (577 nm excitation; 620 nm emission) with an exposure time of 337 ms using a 10× objective to detect enzymatic activity in the wells. The images were then analyzed to determine the fraction of wells that had associated enzymatic activity and the corresponding enzymatic kinetics.

Figure 19A:
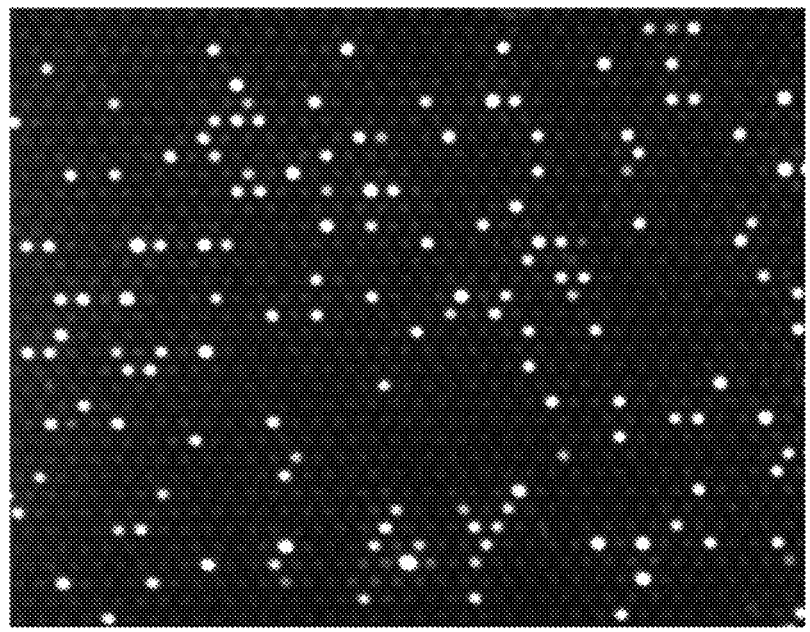
FIG. 19A is a photographic image of an array comprising a plurality of beads in reaction vessels in assay consumables sealed using a PDMS sealing component comprising roller sealing device, according to one embodiment.
Figure 19B:
FIG. 19B is a photographic image of an array comprising a plurality of beads in reaction vessels in assay consumables sealed using a PDMS sealing component using pressure, according to one embodiment.
Figure 19C:
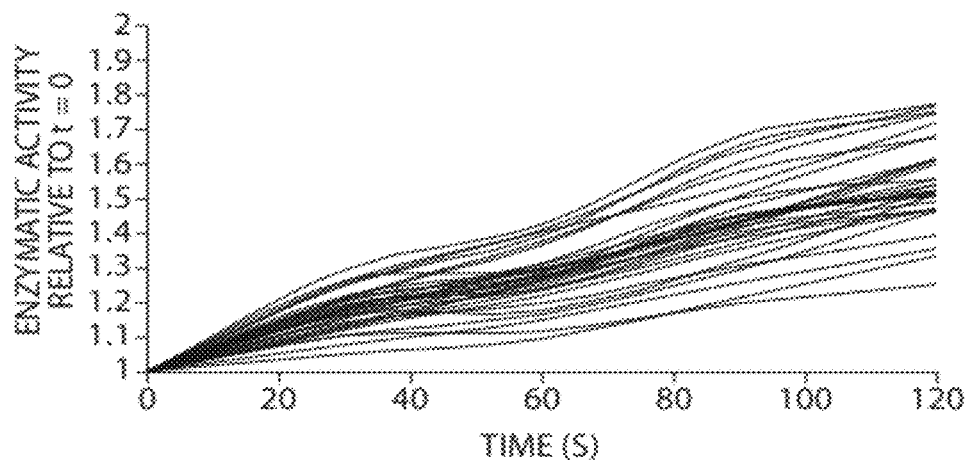
FIGS. 19C and 19D shows quantitative measurement of single enzyme kinetics of individual assay sites from FIGS. 19A and 19B, respectively.
Figure 19D:
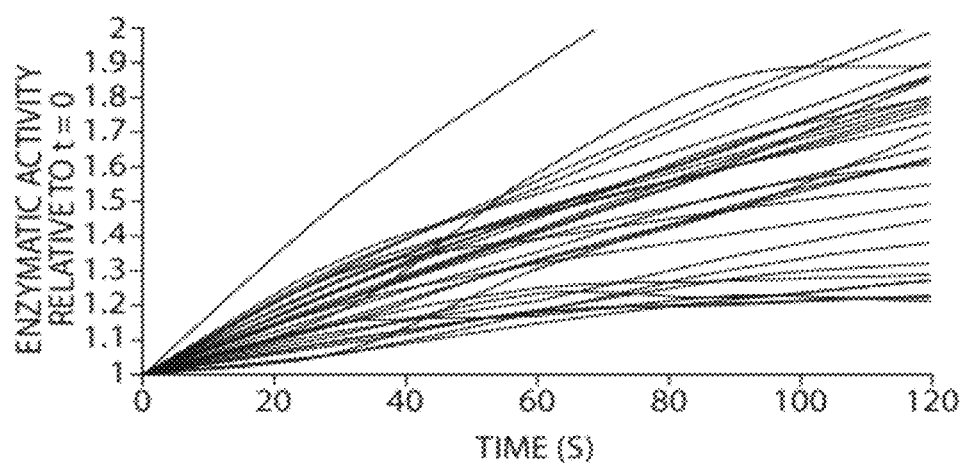

FIG. 19A shows an example of a fluorescence image of single enzymes associate with the array of wells, illustrating the sealability and enzymatic activity using the protocol and device described above. FIG. 19B shows a fluorescence image acquired using the current standard method (arrays made from glass fiber bundle arrays and sealed using a PDMS gasket). FIGS. 19C and 19D illustrate the quantitative measurement of enzyme kinetics using the protocol and device described above, compared to using the current standard method (arrays made from glass fiber bundle arrays and sealed using a PDMS gasket).

Example 2

The following example describes assay bead loading, bead removal, and sealing with a sealing liquid using an open channel assay consumable.

The assay consumable used in this example was obtained from Edge Embossing (Medford, Mass.) and was a COC chip wherein the wells were made using self-embossing techniques. The assay consumable comprised an array of five hundred thousand 50-femtoliter wells. The assay consumable was placed on an assay consumable holder in an orbital shaker with a magnet located directly underneath the array of wells. Assay beads were prepared by capturing prostate specific antigen (PSA) at 10 pg/ml followed by labeling with a biotinylated detection antibody and an enzyme (SβG). 50 µl of assay beads were applied on the surface of the array of wells using a liquid injector. The assay beads were allowed to fall into the wells when a relative motion was created following an orbital track between the assay consumable and the magnet at 100 rpm for 5 minutes. Excess beads were removed by a wiper comprising a rubber doctor blade, followed by the introduction of 50 µl aqueous fluorogenic substrate (RGP) on top of the loaded array of wells. The magnet was then removed, followed by removing the aqueous RGP using the wiper. A fluorocarbon sealing liquid was applied to the array along the trailing end of the doctor blade to seal the array of wells, as schematically illustrated in FIG. 10. In this example, the liquid sealing component 274 comprised a fluorocarbon immiscible with aqueous RGP. The motion of wiper 274 removed the excess RGP and created a seal to seal the wells on the assay consumable. In this example, however, both the optical component 278 of the imaging system and the assay consumable remained stationary. Five fluorescence images (at 30-second intervals) were acquired (577 nm excitation; 620 nm emission) with an exposure time of 337 ms using a 10× objective to detect enzymatic activity in the wells. A white light image was then acquired to identify which wells contained a bead.

Figure 20A:
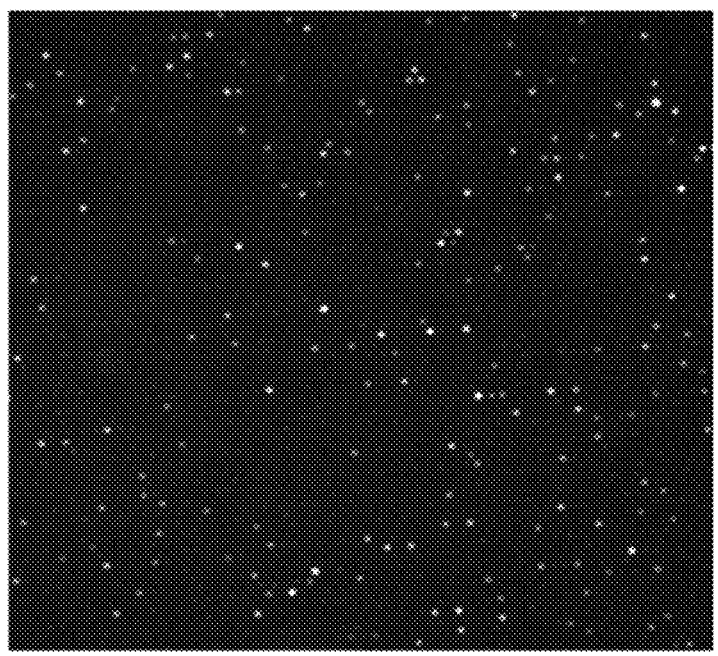
FIGS. 20A and 20B are photographic images of an array comprising a plurality of beads in reaction vessels sealed with a liquid sealing component in an open channel.
Figure 20B:
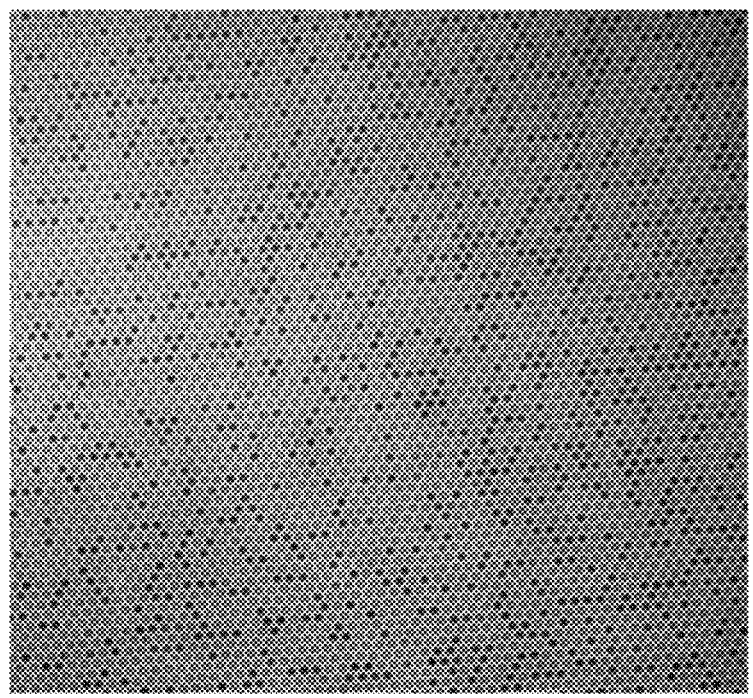

FIG. 20A shows an example of a fluorescence image of single enzymes associated with the beads, illustrating the sealability and enzymatic activity using the procedure described above; while the corresponding white light image indicating the locations of beads is presented in FIG. 20B.

Example 3

The following examples describes use of a system comprising a bead loader, a wiper, and a sealer using an assay consumable comprising a plurality assay sites in a closed channel.

In this example, a molded assay consumable was used having an array of five hundred thousand 50-femtoliter wells with a molded lid thermally bonded to the chip containing the array, together forming a 500-um (micrometer) deep closed channel having two access holes (e.g., an inlet and an outlet), (e.g., similar to the configuration shown in FIG. 8A). The assay consumable was placed on an assay consumable handler stage with a magnet located directly underneath the array of wells (e.g., part of the bead loader). Assay beads were prepared by capturing prostate specific antigen (PSA) at 0 pg/ml, 10 pg/ml and 20 pg/ml followed by labeling with a biotinylated detection antibody and an enzyme (SβG). 50 ul (microliters) of assay beads (in the sample fluid) were loaded into the microchannel through one of the access holes using a liquid injector. A bi-directional (back and forth) flow at a flow rate of approximately 3 ml/min was generated using the same liquid injector for one minute (e.g., through suction/release action of a pipette). This was followed by the introduction of 50 ul aqueous fluorogenic substrate (RGP) (e.g., reagent fluid) to replenish the assay beads medium. The magnet was then removed, followed by the injection of a fluorocarbon sealing liquid (which was substantially immiscible with the reagent fluid and sample fluid) into the microchannel to replace the aqueous medium, wipe the excess beads from the consumable surface, and to seal the wells. Five fluorescence images (at 30-second intervals) were acquired (577 nm excitation; 620 nm emission) with an exposure time of 337 ms using a 10× objective to detect enzymatic activity in the wells. A white light image was then acquired to identify which wells contained a bead. The images were then analyzed to determine the fraction of beads that had associated enzymatic activity.

Figure 21A:
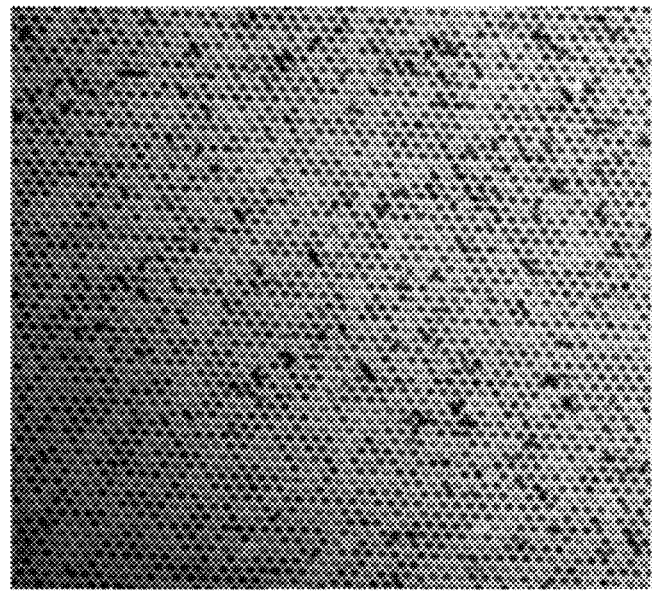
FIGS. 21A-21C are photographic images of an array comprising a plurality of beads in reaction vessels sealed with a liquid sealing component in a closed channel.
Figure 21B:
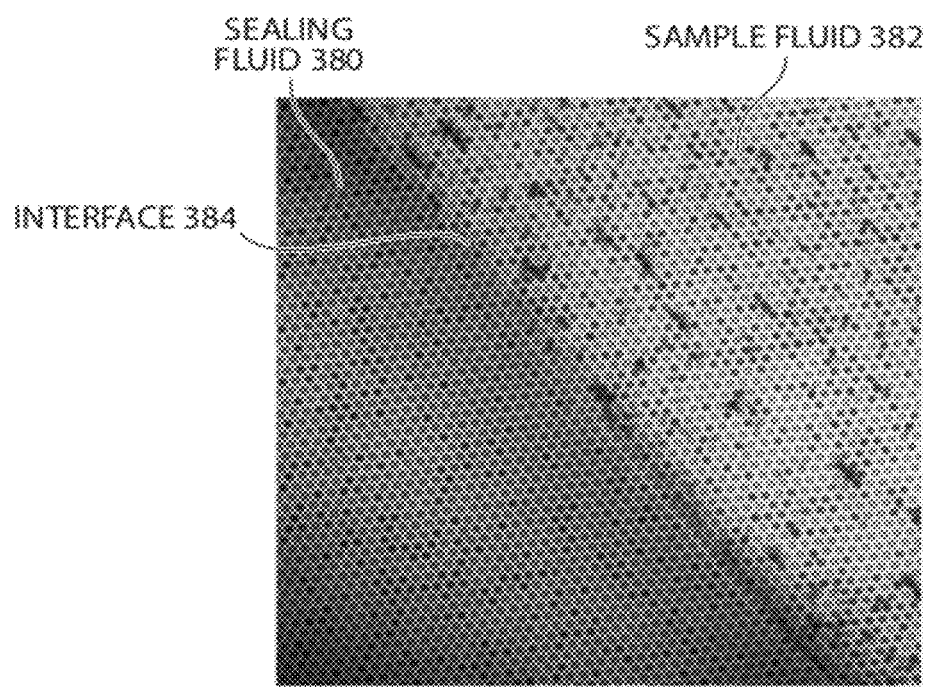
Figure 21C:
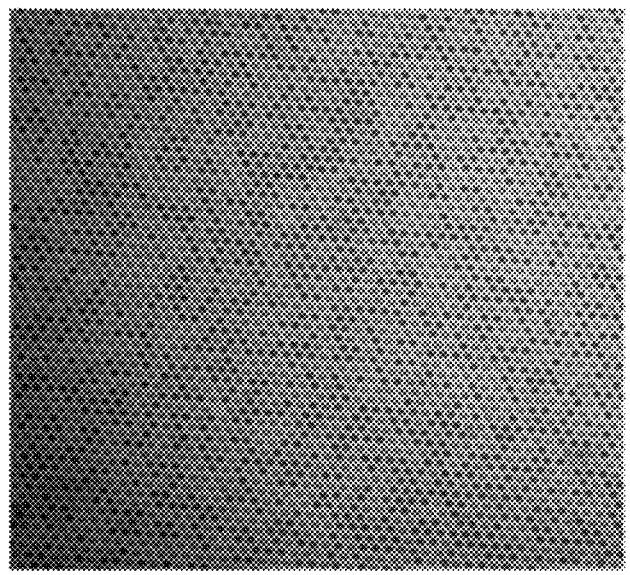
Figure 21D:
FIG. 21D shows a fluorescence photographic image of the array in FIG. 21C.
Figure 21E:
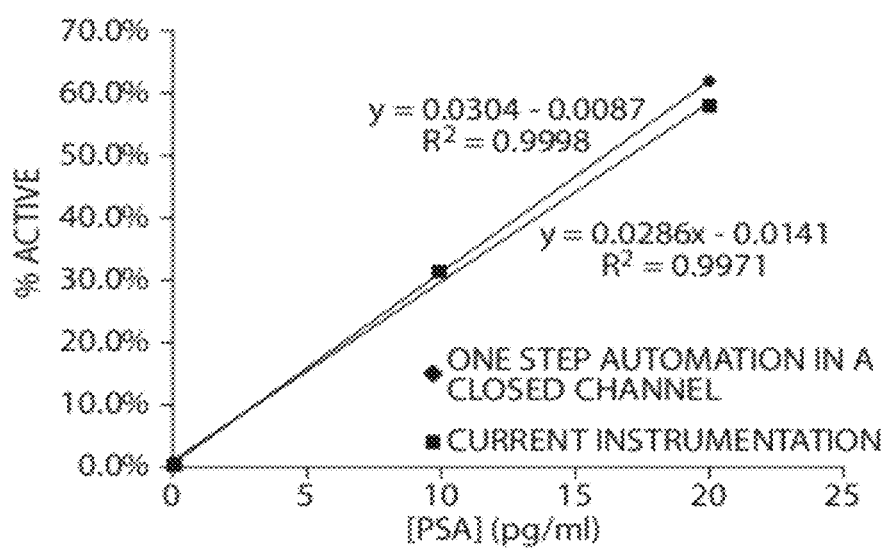
FIG. 21E shows a calibration curve for an assay using a sealing fluid.

FIGS. 21A, 21B, and 21C illustrate the results of bead loading into the wells of the array inside the microchannel and the effect of injecting the fluorocarbon sealing liquid into the closed channel filled with the aqueous bead solution. In FIG. 21A, the assay beads were loaded into the 50-femtoliter wells; excess beads were observed on the assay consumable surface. FIG. 21B shows the aqueous/organic interface 384 during injection of the sealing fluid 380, where the excess beads on the surface were being pushed towards the aqueous phase (e.g., sample fluid 382). FIG. 21C shows the assay sites after addition of fluorocarbon seal liquid, where excess beads were removed while assay beads that were loaded were retained in the 50-femoliter wells. FIG. 21D provides a fluorescence image of the assay sites illustrating the sealability and enzymatic activity as a result of assay bead loading, bead removal, and sealing in one automated step using the closed microchannel approach. FIG. 21E provides a 3-point calibration curve of a PSA (prostate specific antigen) assay using the protocol and device described in this example. In FIG. 21E: Plots of % active beads against [PSA] showing a 3-point calibration curve of a PSA assay using the protocol and device described. The diamonds represent data acquired using liquid sealing in a flow channel. The squares represent data acquired using the method described previously (e.g., arrays made from glass fiber bundle arrays and sealed using a PDMS gasket) on the same bead populations.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. An apparatus for performing an assay, comprising:
   an assay consumable handler configured to be operatively coupled to an assay consumable having a surface comprising a plurality of assay sites, wherein the assay sites have a volume between about 10 attoliter and about 100 picoliter;
   a sealer constructed and positioned to apply a sealing component to the surface of the assay consumable, wherein the sealing component is a sealing liquid;
   a sample loader configured to load an assay sample into at least a portion of the plurality of assay sites of the assay consumable;
   an imaging system configured to acquire an image of at least a portion of the assay sites of the assay consumable containing assay sample; and
   a computer implemented control system configured to automatically operate the sealer and receive information from the imaging system related to the image.

2. The apparatus of claim 1, further comprising the assay consumable operatively coupled to the assay consumable handler.

3. The apparatus of claim 2, wherein the assay consumable contains the assay sample and the assay sample comprises an unknown concentration of an analyte molecule.

4. The apparatus of claim 3, wherein the computer implemented control system is configured to determine a measure of the unknown concentration of the analyte molecule in the assay sample.

5. The apparatus of claim 2, wherein the assay sites comprise a plurality of reaction vessels formed in the surface of the assay consumable.

6. The apparatus of claim 1, wherein the computer implemented control system is configured to automatically operate the sample loader.

7. The apparatus of claim 2, wherein the assay consumable comprises a plurality of fluidically isolated areas, each isolated area comprising a plurality of assay sites.

8. The apparatus of claim 7, wherein the plurality of fluidically isolated areas are situated on a disc.

9. The apparatus of claim 1, wherein the sealing liquid is substantially immiscible with a liquid contained in each assay site.

10. The apparatus of claim 1, wherein the surface is formed of cyclic olefin copolymer or cyclic olefin polymer and the sealing liquid is a fluorinated oil.

11. An apparatus for sealing a plurality of assay sites, comprising:
    an assay consumable handler configured to be operatively coupled to an assay consumable having a surface comprising a plurality of assay sites, wherein the assay sites have a volume between about 10 attoliter and about 100 picoliter;
    a sealer constructed and positioned to apply a sealing component to the surface of the assay consumable to form a plurality of sealed assay sites, wherein the contents of each sealed assay site is substantially isolated from the contents of each of the other plurality of sealed assay sites, wherein the sealing component is a sealing liquid; and
    a controller configured to automatically operate the sealer to apply the sealing component to the plurality of assay sites.

12. The apparatus of claim 11, wherein the sealer, the sample loader, and the imaging system are positioned about the disc, and wherein the apparatus is capable of providing rotational relative motion between the disc and the sealer, the sample loader, and the imaging system.

13. The apparatus of claim 11, further comprising the assay consumable operatively coupled to the assay consumable handler.

14. The apparatus of claim 13, wherein the assay sites are sized and/or shaped to each contain only zero or one bead.

15. The apparatus of claim 11, wherein the plurality of assays sites are contained in a channel on the assay consumable.

16. The apparatus of claim 11, wherein the surface is formed of cyclic olefin copolymer or cyclic olefin polymer and the sealing liquid is a fluorinated oil.

17. An apparatus for inserting beads into assay sites on an assay consumable, comprising:
    an assay consumable handler configured to be operatively coupled to an assay consumable having a surface comprising a plurality of assay sites, wherein the assay sites have a volume between about 10 attoliter and about 100 picoliters;
    a bead loader configured to insert individual beads into individual assay sites, such that each assay site containing a bead will contain no more than one bead;
    a sealer constructed and positioned to apply a sealing component to the surface of the assay consumable handler, wherein the sealing component is a sealing liquid; and
    a controller configured to automatically operate the bead loader to insert individual beads into individual assay sites.

18. The apparatus of claim 17, further comprising the assay consumable operatively coupled to the assay consumable handler.

19. The apparatus of claim 17, wherein the apparatus is capable of fluidically isolating individual beads in individual assay sites.

20. The apparatus of claim 17, wherein the surface is formed of cyclic olefin copolymer or cyclic olefin polymer and the sealing liquid is a fluorinated oil.

21. An apparatus for performing an assay, comprising:
an assay consumable handler configured to be operatively coupled to an assay consumable having a surface comprising a plurality of assay sites, wherein the assay sites have a volume between about 10 attoliter and about 100 picoliter;
a sample loader configured to load an assay sample containing analyte molecules or particles having an unknown concentration to be measured into at least a portion of the plurality of assay sites, such that a plurality of assay sites into which assay sample is loaded contain either zero or a single analyte molecule or particle;
a sealer constructed and positioned to apply a sealing component to the surface of the assay consumable, wherein the sealing component is a sealing;
a detector configured to interrogate at least a portion of the assay sites containing assay sample and determine a fraction of the plurality of assay sites interrogated that contain an analyte molecule or particle; and
a computer implemented system configured receive information from the detector and from the information determine a measure of the unknown concentration of the analyte molecules or particles in the assay sample.

22. The apparatus of claim 21, further comprising the assay consumable operatively coupled to the assay consumable handler.

23. The apparatus of claim 21, wherein the computer implemented system is configured to determine the fraction of the at least a portion of the assay sites interrogated which contain zero or one analyte molecule or particle.

24. The apparatus of claim 23, wherein the measure of the unknown concentration of analyte molecules or particles in the assay sample is determined, at least in part, based on the fraction of the at least a portion of the assay sites interrogate which contain zero or one analyte molecule or particle.

25. The apparatus of claim 21, wherein the surface is formed of cyclic olefin copolymer or cyclic olefin polymer and the sealing liquid is a fluorinated oil.

* * * * *

UNITED STATES PATENT AND TRADEMARK OFFICE
CERTIFICATE OF CORRECTION

PATENT NO. : 9,952,237 B2
APPLICATION NO. : 13/035472
DATED : April 24, 2018
INVENTOR(S) : David Fournier et al.

Page 1 of 1

It is certified that error appears in the above-identified patent and that said Letters Patent is hereby corrected as shown below:

In the Specification

At Column 21, Line 25, the word "compilable" should read --compliable--

At Column 33, Line 62, the words "FIGS. 17H and 171" should read --FIGS. 17H and 17I--

Signed and Sealed this
Fifth Day of June, 2018

Andrei Iancu
*Director of the United States Patent and Trademark Office*